United States Patent
Pasternak et al.

(10) Patent No.: US 9,604,998 B2
(45) Date of Patent: Mar. 28, 2017

(54) INHIBITORS OF THE RENAL OUTER MEDULLARY POTASSIUM CHANNEL

(71) Applicant: MERCK SHARP & DOHME CORP., Rahway, NJ (US)

(72) Inventors: Alexander Pasternak, Princeton, NJ (US); Reynalda Keh DeJesus, East Brunswick, NJ (US); Fa-Xiang Ding, Staten Island, NY (US); Shuzhi Dong, Plainsboro, NJ (US); Jessica L. Frie, Harleysville, PA (US); Xin Gu, Scotch Plains, NJ (US); Jinlong Jiang, Scotch Plains, NJ (US); Aurash Shahripour, Iselin, NJ (US); Barbara Pio, West Orange, NJ (US); Haifeng Tang, Metuchen, NJ (US); Shawn Walsh, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 6 days.

(21) Appl. No.: 14/768,245

(22) PCT Filed: Feb. 12, 2014

(86) PCT No.: PCT/US2014/015901
§ 371 (c)(1),
(2) Date: Aug. 17, 2015

(87) PCT Pub. No.: WO2014/126944
PCT Pub. Date: Aug. 21, 2014

(65) Prior Publication Data
US 2016/0002259 A1 Jan. 7, 2016

Related U.S. Application Data

(60) Provisional application No. 61/765,913, filed on Feb. 18, 2013.

(51) Int. Cl.
| | |
|---|---|
| *A61K 31/401* | (2006.01) |
| *C07D 498/04* | (2006.01) |
| *A61K 31/5383* | (2006.01) |
| *C07D 487/04* | (2006.01) |
| *C07D 519/00* | (2006.01) |
| *A61K 31/403* | (2006.01) |
| *A61K 31/41* | (2006.01) |
| *A61K 31/4178* | (2006.01) |
| *A61K 31/4184* | (2006.01) |
| *A61K 31/4422* | (2006.01) |
| *A61K 31/4985* | (2006.01) |
| *A61K 31/55* | (2006.01) |
| *A61K 31/675* | (2006.01) |
| *A61K 45/06* | (2006.01) |

(52) U.S. Cl.
CPC ......... *C07D 498/04* (2013.01); *A61K 31/401* (2013.01); *A61K 31/403* (2013.01); *A61K 31/41* (2013.01); *A61K 31/4178* (2013.01); *A61K 31/4184* (2013.01); *A61K 31/4422* (2013.01); *A61K 31/4985* (2013.01); *A61K 31/5383* (2013.01); *A61K 31/55* (2013.01); *A61K 31/675* (2013.01); *A61K 45/06* (2013.01); *C07D 487/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 2,988,551 | A | 6/1961 | Morren |
| 3,435,002 | A | 3/1969 | Holub |
| 3,632,608 | A | 1/1972 | Holub |
| 3,749,722 | A | 7/1973 | Holub |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).

(Continued)

*Primary Examiner* — Craig Ricci
(74) *Attorney, Agent, or Firm* — Baerbel R. Brown; Catherine D. Fitch

(57) ABSTRACT

The present invention provides compounds of Formula I

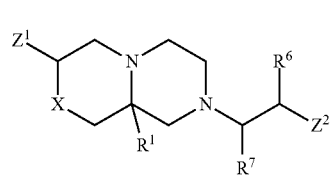

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure, kidney disease, edema, and conditions associated with excessive salt and water retention.

14 Claims, No Drawings

(56) References Cited

U.S. PATENT DOCUMENTS

| | | | |
|---|---|---|---|
| 4,579,863 | A | 4/1986 | Horwell et al. |
| 4,806,536 | A | 2/1989 | Cross et al. |
| 4,992,547 | A | 2/1991 | Berner et al. |
| 5,145,885 | A | 9/1992 | Berner et al. |
| 5,215,989 | A | 6/1993 | Baldwin et al. |
| 5,614,526 | A | 3/1997 | Godel et al. |
| 5,736,546 | A | 4/1998 | Kawashima et al. |
| 6,258,813 | B1 | 7/2001 | Arlt et al. |
| 6,787,543 | B2 * | 9/2004 | Take .............. C07C 45/71 514/239.2 |
| 8,673,920 | B2 | 3/2014 | Pasternak et al. |
| 8,952,166 | B2 | 2/2015 | Ding et al. |
| 9,206,199 | B2 * | 12/2015 | Pio .............. A61K 31/4178 |
| 2004/0110793 | A1 | 6/2004 | Lloyd et al. |
| 2004/0204404 | A1 | 10/2004 | Zelle et al. |
| 2005/0215526 | A1 | 9/2005 | Hulme et al. |
| 2005/0267121 | A1 | 12/2005 | Li et al. |
| 2006/0183739 | A1 | 8/2006 | Tsaklakidis et al. |
| 2006/0183742 | A1 | 8/2006 | Mederski et al. |
| 2006/0211692 | A1 | 9/2006 | Mederski et al. |
| 2007/0004750 | A1 | 1/2007 | Lorsbach et al. |
| 2007/0072865 | A1 | 3/2007 | Fukatsu et al. |
| 2007/0093472 | A1 | 4/2007 | Mederski et al. |
| 2008/0003214 | A1 | 1/2008 | Cezanne et al. |
| 2008/0090794 | A1 | 4/2008 | Dinsmore et al. |
| 2010/0286123 | A1 * | 11/2010 | Pasternak .......... C07D 295/135 514/215 |
| 2015/0329557 | A1 * | 11/2015 | Pasternak .......... A61K 31/5383 514/91 |

FOREIGN PATENT DOCUMENTS

| | | | |
|---|---|---|---|
| EP | 1094063 | A1 | 4/2001 |
| EP | 1939175 | A1 | 7/2009 |
| FR | 2673182 | | 8/1992 |
| FR | 2673182 | A1 | 8/1992 |
| GB | 949088 | A | 2/1964 |
| GB | 1575310 | A | 9/1980 |
| GB | 2116967 | | 7/1986 |
| JP | 10203986 | | 8/1998 |
| WO | 9744329 | | 11/1997 |
| WO | 0051611 | A1 | 9/2000 |
| WO | 0232874 | | 4/2002 |
| WO | 0204314 | A1 | 6/2002 |
| WO | 0250061 | A1 | 6/2002 |
| WO | 2004020422 | A1 | 3/2004 |
| WO | 2004037817 | A1 | 5/2004 |
| WO | 2004046110 | | 6/2004 |
| WO | 2005037843 | | 4/2005 |
| WO | 2005044797 | | 5/2005 |
| WO | 2006034341 | A2 | 3/2006 |
| WO | 2006034769 | A1 | 4/2006 |
| WO | 2006098342 | A1 | 9/2006 |
| WO | 2006129199 | A1 | 12/2006 |
| WO | 2007075629 | A2 | 7/2007 |
| WO | 2008147864 | | 12/2008 |
| WO | 2008147864 | A2 | 12/2008 |
| WO | 2009149508 | | 11/2009 |
| WO | 2010129379 | A1 | 11/2010 |
| WO | 2012058116 | A1 | 5/2012 |
| WO | 2012058134 | A1 | 5/2012 |
| WO | 2013028474 | A1 | 2/2013 |
| WO | 2013039802 | A1 | 3/2013 |
| WO | 2013062892 | A1 | 5/2013 |
| WO | 2013062900 | A1 | 5/2013 |
| WO | 2013066714 | A1 | 5/2013 |
| WO | 2013066717 | A1 | 5/2013 |
| WO | 2013066718 | A2 | 5/2013 |
| WO | 2013090271 | A1 | 6/2013 |
| WO | 2014018764 | A1 | 1/2014 |
| WO | W02014085210 | A1 | 6/2014 |
| WO | W02014099633 | A2 | 6/2014 |
| WO | W02014150132 | A1 | 9/2014 |
| WO | W02015017305 | A1 | 2/2015 |
| WO | W02015065866 | A1 | 5/2015 |

OTHER PUBLICATIONS

Bhave, G., Development of a selective small-molecule inhibitor Kir1.1, the renal outer medullary potassium channel, Mol. Pharmacol., 2011, 42-50, 79.
Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-Isobenzofurandione 5-[[4-[(5-chloro-2-methoxyphenyl) sulfonyl]-1-..."
Cheymol et al., Increase in the effects of epinephrine and acetylcholine..., Comptes Rendus des seances de la Societe de Biologie, 1951, 496-499 (English trans.), 145.
Dorwald, Side reactions in Organic Synthesis: A Guide to Successful Synthesis Design, 2005, Chapter 1.
Fallen, K., The Kir channel immunoglobuling domain is essential for Kir1.1 (ROMK) thermodynamic stability, trafficing and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.
International Search Report and Written Opinion for PCT/US2014/015901 mailed May 12, 2014, 7 pages.
International Search Report for PCT/US 13/74846, mailed Aug. 15, 2014, 8 pages.
Kulkarni, YD, Possible antifertility agents, part III. Synthesis of 4-(substituted aminomethyl)-5,6,7-trimethoxy phthalid ... (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman ..., Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US14/015901 filed Feb. 12, 2014, which claims priority from U.S. Provisional Application Ser. No. 61/765,913, filed Feb. 18, 2013.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

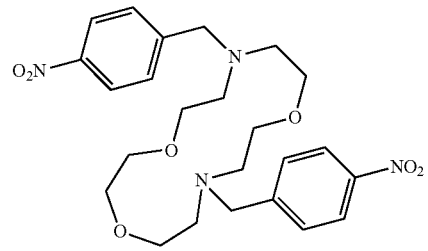

VU590

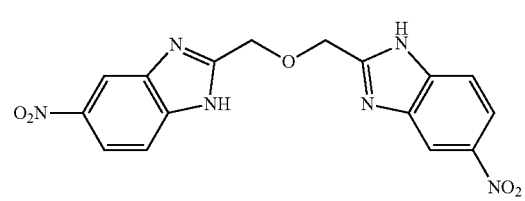

VU591

Patent application publication number WO2010/129379, published Nov. 11, 2010 having common representative Merck Sharp & Dohme Corp., (also published as US2010/0286123 on same date), describes ROMK inhibitors having the generic formula:

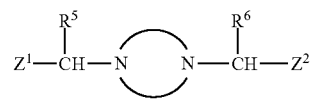

and, e.g., an embodiment

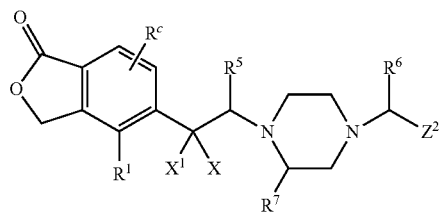

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

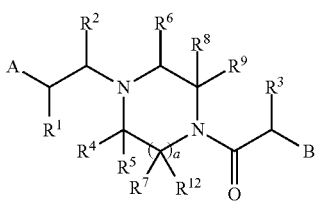

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

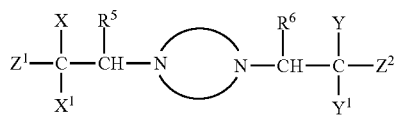

and, e.g., an embodiment

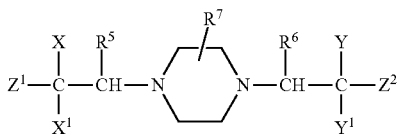

wherein $R^5$ and $R^6$ are independently —H, —$C_{1-6}$ alkyl or —$C(O)OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

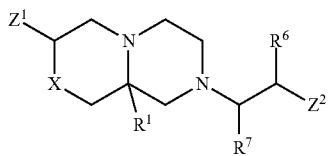

I and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

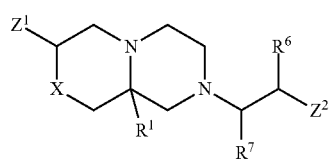

I and the pharmaceutically acceptable salts thereof wherein:
$R^1$ is —H or —$C_{1-4}$alkyl;
X is O, NH or S;
$Z^1$ is

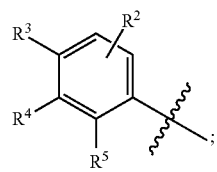

$R^2$ is —H, halo, —$C_{1-6}$alkyl, —$C_{3-6}$cycloalkyl or —$OC_{1-6}$ alkyl;

$R^3$ is —H, halo, —CN, —$C_{1-6}$alkyl, —$C_{3-6}$cycloalkyl, —$OC_{1-6}$alkyl or N-tetrazolyl optionally substituted with —$CH_3$;

$R^4$ is —H, halo, —CN, —$C_{1-6}$alkyl, —$C_{3-6}$cycloalkyl, —$OC_{1-6}$alkyl or N-tetrazolyl optionally substituted with —$CH_3$;

or $R^3$ and $R^4$ are joined together, and with the phenyl ring to which they are attached together represent:

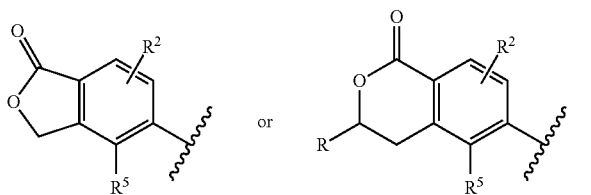 or 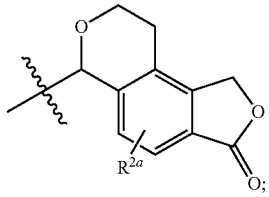

wherein R is —H or —$C_{1-4}$alkyl;

$R^5$ is —H, halo, —CN, —$C_{1-4}$alkyl, —$OC_{1-4}$alkyl or —$C_{3-6}$cycloalkyl;

provided that when $R^3$ and $R^4$ are not joined together, then
(a) one and only one of $R^3$, $R^4$ or $R^5$ is —CN, or
(b) one of $R^3$ or $R^4$ is N-tetrazolyl optionally substituted with —$CH_3$ and the other is not N-tetrazolyl optionally substituted with —$CH_3$;

$Z^2$ is

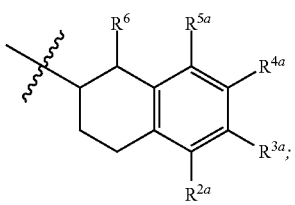

$R^{2a}$ is —H, halo, —$C_{1-6}$alkyl, —$C_{3-6}$cycloalkyl or —$OC_{1-6}$alkyl;

$R^{3a}$ is —H, halo, —CN, —$C_{1-6}$alkyl, —$C_{3-6}$cycloalkyl, —$OC_{1-6}$alkyl or N-tetrazolyl optionally substituted with —$CH_3$;

$R^{4a}$ is —H, halo, —CN, —$C_{1-6}$alkyl, —$C_{3-6}$cycloalkyl, —$OC_{1-6}$alkyl or N-tetrazolyl optionally substituted with —$CH_3$;

or $R^{3a}$ and $R^{4a}$ are joined together, and with the phenyl ring to which they are attached together represent:

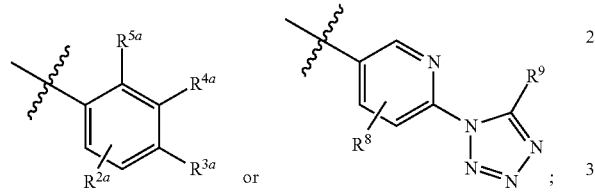

wherein $R^a$ is —H or —$C_{1-4}$alkyl;

$R^{5a}$ is —H, halo, —CN, —$C_{1-4}$alkyl, —$OC_{1-4}$alkyl or —$C_{3-6}$ cycloalkyl;

provided that when $R^{3a}$ and $R^{4a}$ are not joined together, then
(a) one of $R^{3a}$, $R^{4a}$ or $R^{5a}$ is —CN and the others are not —CN, or
(b) one of $R^{3a}$ or $R^{4a}$ is N-tetrazolyl optionally substituted with —$CH_3$ and the other is not N-tetrazolyl optionally substituted with —$CH_3$;

$R^6$ is —H, —OH or —$C_{1-3}$alkyl; or $R^6$ is —O— and is joined together with $Z^2$ to represent:

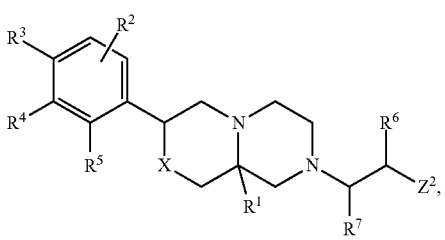

$R^7$ is —H; or $R^7$ together with —$CHR^6$— and $Z^2$ represents

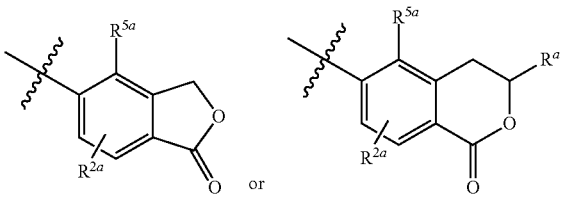

$R^8$ is —H or —$C_{1-3}$alkyl; and
$R^9$ is —H or —$CH_3$.

In another embodiment of this invention are compounds of Formula I having structural Formula II and the pharmaceutically acceptable salts thereof:

II wherein each of the variables $Z^2$, $R^1$, $R^2$, $R^3$, $R^4$, $R^5$, $R^6$, $R^7$, X and all other variables therein are as defined in Formula I.

In an embodiment of this invention are compounds of Formula I or II wherein:

$R^3$ and $R^4$ are not joined together (that is, $Z^1$ is the mono-ring phenyl substituted with $R^2$, $R^3$, $R^4$ and $R^5$), and:

$R^2$ is —H, halo, —$C_{1-3}$alkyl or —$OC_{1-3}$alkyl, and particularly —H, —Cl, —F, —Br, —$CH_3$ or —$OCH_3$;

$R^3$ is halo, —CN or —$OC_{1-3}$alkyl, and particularly —CN, —F or —$OCH_3$;

$R^4$ is —H, halo, —CN or —$OC_{1-3}$alkyl, and particularly —CN, —F or —$OCH_3$; and $R^5$ is —H, halo, —$C_{1-3}$alkyl, —$OC_{1-3}$alkyl or —$C_{3-4}$cycloalkyl, and particularly —H, —$CH_3$, —$OCH_3$, —Cl, —F, —Br or cyclopropyl;

provided that one of $R^3$ or $R^4$ is —CN and the other is not —CN.

In another embodiment of this invention are compounds of Formula I or II having structural Formula III and the pharmaceutically acceptable salts thereof:

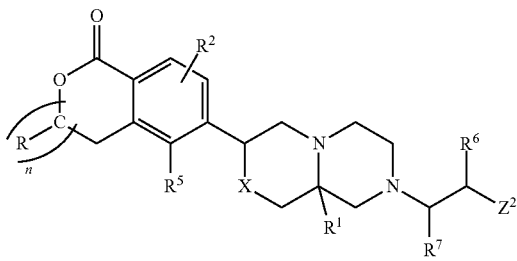

III wherein n is the integer zero or 1, and each of the variables $Z^2$, R, $R^1$, $R^2$, $R^5$, $R^6$, $R^7$, X and all other variables therein are as defined in Formula I.

In an embodiment of this invention are compounds of Formula I or III wherein:

$R^2$ is —H, halo, —$C_{1-3}$alkyl or —$OC_{1-3}$alkyl, and particularly —H, —Cl, —F, —Br, —$CH_3$ or —$OCH_3$; and $R^5$ is —H, halo, —$C_{1-3}$alkyl, —$OC_{1-3}$alkyl or —$C_{3-4}$cycloalkyl, and particularly —H, —$CH_3$, —$OCH_3$, —Cl, —F, —Br or cyclopropyl.

In an embodiment f this invention are compounds of Formula I, II or III wherein
(i) $Z^2$ is

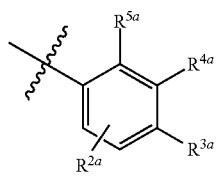

or
(ii) $R^7$ together with —$CHR^6$— and $Z^2$ represents:

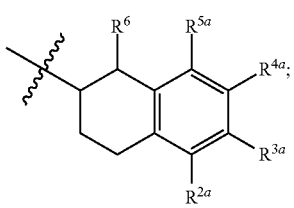

$R^{2a}$ is —H, halo, —$C_{1-3}$alkyl or —$OC_{1-3}$alkyl, and particularly —H, —Cl, —F, —Br, —$CH_3$ or —$OCH_3$;
$R^{3a}$ is halo, —CN, —$OC_{1-3}$alkyl or N-tetrazolyl, and particularly —CN, —F, —$OCH_3$ or N-tetrazolyl;
$R^{4a}$ is —H, halo, —CN, —$OC_{1-3}$alkyl or N-tetrazolyl, and particularly —CN, —F, —$OCH_3$ or N-tetrazolyl; and
$R^{5a}$ is —H, halo, —$C_{1-3}$alkyl, —$OC_{1-3}$alkyl or —$C_{3-4}$cycloalkyl, and particularly —H, —$CH_3$, —$OCH_3$, —Cl, —F, —Br or cyclopropyl; provided that:
(a) one of $R^{3a}$ or $R^{4a}$ is —CN and the other is not —CN, or
(b) one of $R^{3a}$ or $R^{4a}$ is N-tetrazolyl and the other is not N-tetrazolyl.

In another embodiment of this invention are compounds of Formula I, II or III wherein $Z^2$ is

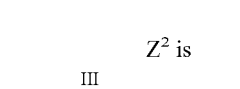

and
$R^8$ is —H or —$C_{1-3}$alkyl, and particularly it is —H or —$CH_3$; and
$R^9$ is —H or —$CH_3$, and particularly it is —H In another embodiment of this invention are compounds of Formula I, II or III wherein
$Z^2$ is

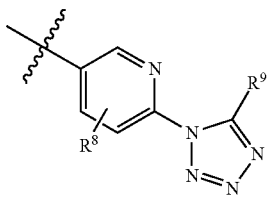

wherein $R^{2a}$ is —H, halo, —$C_{1-3}$alkyl or —$OC_{1-3}$alkyl, and particularly —H, —Cl, —F, —Br, —$CH_3$ or —$OCH_3$; and $R^{5a}$ is —H, halo, —$C_{1-3}$alkyl, —$OC_{1-3}$alkyl or —$C_{3-4}$cycloalkyl, and particularly —H, —$CH_3$, —$OCH_3$, —Cl, —F, —Br or cyclopropyl.

In another embodiment of this invention are compounds of Formula I, II or III wherein $R^6$ is —O— and is joined together with $Z^2$ to represent:

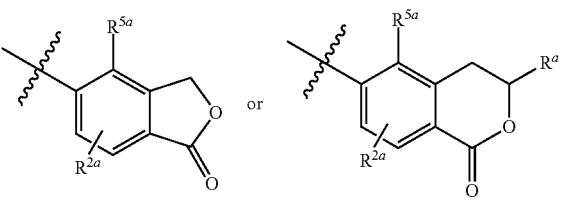

and $R^{2a}$ is —H, halo, —$C_{1-3}$alkyl or —$OC_{1-3}$alkyl, and particularly —H, —Cl, —F, —Br, —$CH_3$ or —$OCH_3$.

In an embodiment of this invention are compounds of Formula I, II or III, and each of the other embodiments described herein, wherein X is O. In an alternate embodiment are compounds of Formula I, II or III, and each of the other embodiments described herein, wherein X is N. In another alternate embodiment are compounds of Formula I, II or III, and each of the other embodiments described herein, wherein X is S.

In an embodiment of this invention are compounds Formula I, II or III, and each of the other embodiments described herein, wherein R is —H or —$CH_3$, and more particularly it is —H.

In an embodiment of this invention are compounds of Formula I, II or III, and each of the other embodiments described herein, wherein $R^1$ is —H or —$CH_3$, and more particularly it is —H.

In an embodiment of this invention are compounds of Formula I, II or III, and each of the other embodiments described herein, wherein $R^6$ is —H, —OH or —CH$_3$.

All structural Formulas and embodiments thereof described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). "Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I. Preferred halo are —F, —Cl and —Br, and more preferably —F and —Cl.

Unless expressly depicted or described otherwise, variables depicted in a structural formula with a "floating" bond, such as $R^2$, are permitted on any available carbon atom in the ring to which the variable is attached.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formulas I, II or III and all embodiments thereof. Reference to the compounds of this invention as those of a specific formula or embodiment, e.g., Formula I, II or III or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay and/or Electrophysiology Assay described below. Moreover, this invention also relates to the use of the compounds of Formula I or salts thereof to validate in vitro assays, for example but not limited to the Thallium Flux and Electrophysiology Assays described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 μM or less, preferably 1 μM or less, and more preferably 0.25 μM or less, in at least one of the following assays: 1) Thallium Flux Assay, 2) Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or *acacia*, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the examples. Starting materials and intermediates are commercially available, or made from known procedures or as illustrated. Modifications of the procedures disclosed in the examples as may be known in the art may also be used to prepare the compounds. Some frequently applied routes to the compounds of Formula I are also described by the Schemes as follows. In some cases the order of carrying out the steps of reaction schemes may be varied to facilitate the reaction or to avoid unwanted reaction products. The variable substituents in the structures of the Schemes correspond to the substituents defined in Formula I at the same positions on the structures.

Compounds of this invention may be prepared as shown in Scheme 1 by coupling of piperazines 1 with epoxides 2 by heating in a solvent such as ethanol, DMSO, or toluene to afford alcohols of the formula Ia (Nomura, Y. et al. Chemical & Pharmaceutical Bulletin, 1995, 43(2), 241-6). Heating can be by conventional thermal bath or by microwave irradiation. When epoxides are racemic mixtures, compounds Ia are produced as mixtures of diastereomers which may be separated to individual alcohol isomers Ia-1 and Ia-2 by chiral HPLC, reversed phase HPLC, or by TLC.

Scheme 1

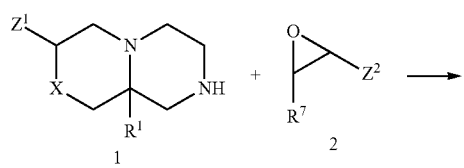

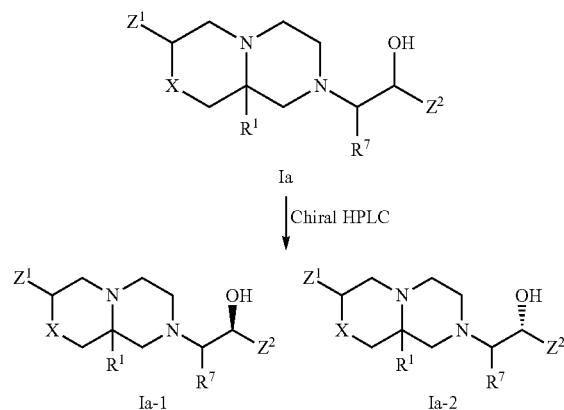

Alternatively, individual alcohol diastereomers Ia-1 and Ia-2 may be prepared in a similar fashion as described in Scheme 1, except where the epoxide is enantiomerically enriched (single enantiomers, either 2-1 or 2-2). In this fashion (Scheme 2), the single alcohol diastereomers Ia-1 and Ia-2 are directly produced on epoxide opening without necessity for subsequent separation of diastereomer mixtures.

Scheme 2

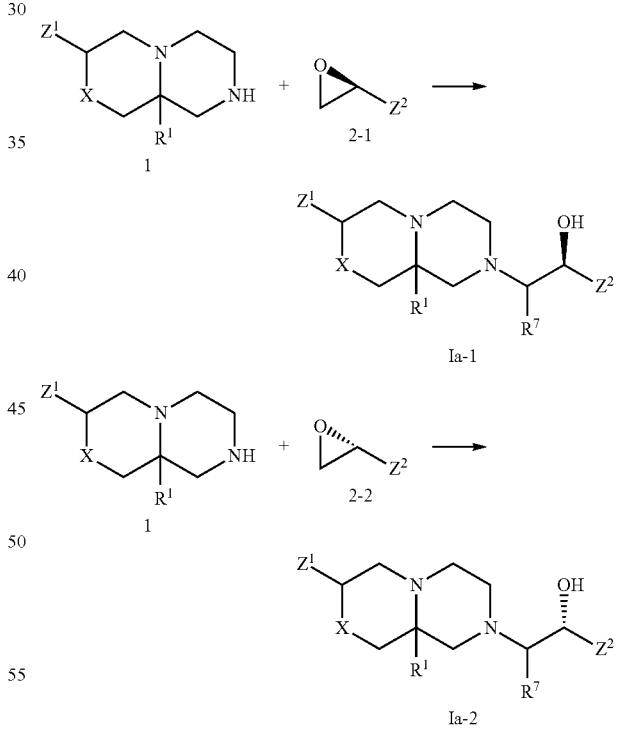

Compounds of the current invention may also be prepared according to Scheme 3, where piperazines 1 undergo reductive alkylation with aldehydes or ketones 3. This can be accomplished using a number of methods well-known to the chemist, for example, with sodium triacetoxyborohydride in 1,2-dichloroethane solvent, with sodium cyanoborohydride in a solvent such as methanol, or by treatment with titanium tetra-isopropoxide, followed by sodium borohydride.

Scheme 3

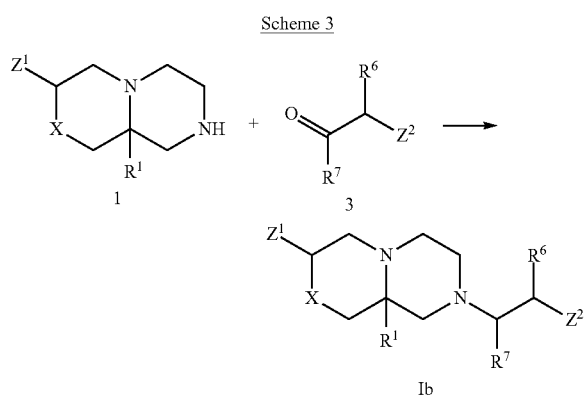

When "X" represents a protected nitrogen atom (Greene, T.; Wuts, P. G. M. *protective Groups in Organic Synthesis*, John Wiley and Sons, Inc., New York, N.Y. 1991), the protective group may be removed to afford the corresponding secondary amines of the formula Id. For example, in Scheme 4 where "X" represents a tert-butoxycarbonyl protected nitrogen (Ic), deprotection is readily accomplished in a number of ways, such as by treatment with TFA in a solvent such as dichloromethane, or by treatment with HCl in ether, dioxane, or ethyl acetate.

Scheme 4

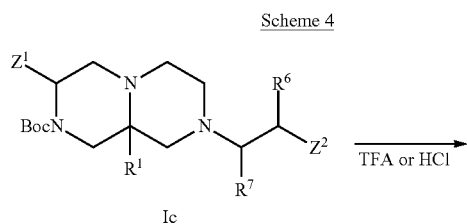

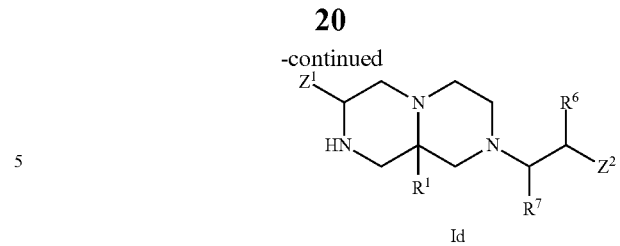

Piperazines 1 can be prepared according to Scheme 5. Epoxides 2-3 can be coupled with appropriately protected hydroxyalkylpiperazines 4 by heating in a solvent such as ethanol, DMSO, or toluene to afford the diols 5 (Nomura, Y. et al. Chemical & Pharmaceutical Bulletin, 1995, 43(2), 241-6). Heating can be by conventional thermal bath or by microwave irradiation. The diols 5 can be cyclized to afford 6-membered rings 6 in a variety of ways, including by heating with the reagent cyanomethylene tri-n-butylphosphorane in a suitable solvent such as benzene or toluene. Heating can be by conventional thermal bath or by microwave irradiation. The resulting compounds 6 are generally mixtures of cis and trans isomers. The protective group (Greene, T.; Wuts, P. G. M. *protective Groups in Organic Synthesis*, John Wiley and Sons, Inc., New York, N.Y. 1991) can then be removed. For example, when the protective group is Boc as shown in Scheme 5, removal can be achieved by treatment with an acid such as TFA or HCl to afford piperazines 1A. Alternatively, cis-trans isomer mixtures 6 can be separated by means of silica chromatography or preparative high pressure liquid chromatography employing a chiral column to afford the separated cis 6 (cis) and trans 6 (trans) isomers. The protective group on these separated isomers can then be removed by treatment with an acid such as TFA or HCl (in the case of a Boc group) to afford piperazines 1A as pure cis and trans isomers 1A (cis) and 1A (trans). If a single enantiomer of the hydroxyalkylpiperazines 4 is employed, then single enantiomer cis and trans isomers 1A (cis), and 1A (trans) can be obtained.

Scheme 5

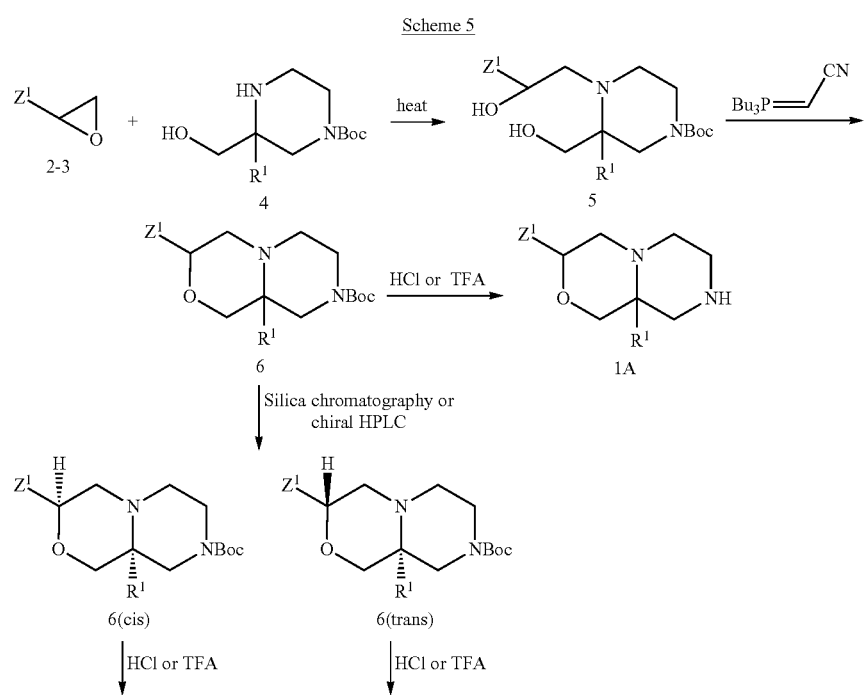

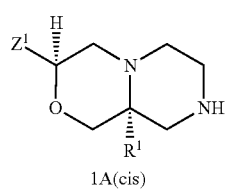

1A(cis)

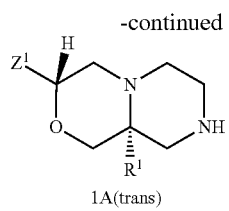

1A(trans)

Protected piperazines 6 can also be prepared according to Scheme 6 by initially coupling suitably protected hydroxyalkylpiperazines 4 with bromomethylketones (or chloromethyl ketones) 7 to afford hemiketals 8. This is typically accomplished in the presence of a base such as triethylamine or diethylisopropylamine. The resulting hemiketals 8 can be converted directly to piperazines 1A by reduction using, for example, triethylsilane in the presence of an acid catalyst such as trifluoroacetic acid. If separation of the cis and trans isomers is desired, a protective group such as Boc may be installed using, for example, Boc₂O, to give intermediates 6 which can be separated into cis and trans isomers as described in Scheme 5. Alternatively, the hemiketals 8 may be reduced by a three step sequence involving formation of a mesylate with mesyl chloride and a base such as triethylamine, followed by elimination in the presence of base to give enol ethers 9. Enol ethers 9 can then be reduced by hydrogenation in the presence of a catalyst such as palladium on carbon to afford protected piperazines 6 which can be separated into cis and trans isomers as described in Scheme 5. These may then be converted to piperazine intermediates 1A (cis) and 1A (trans) as described in Scheme 5.

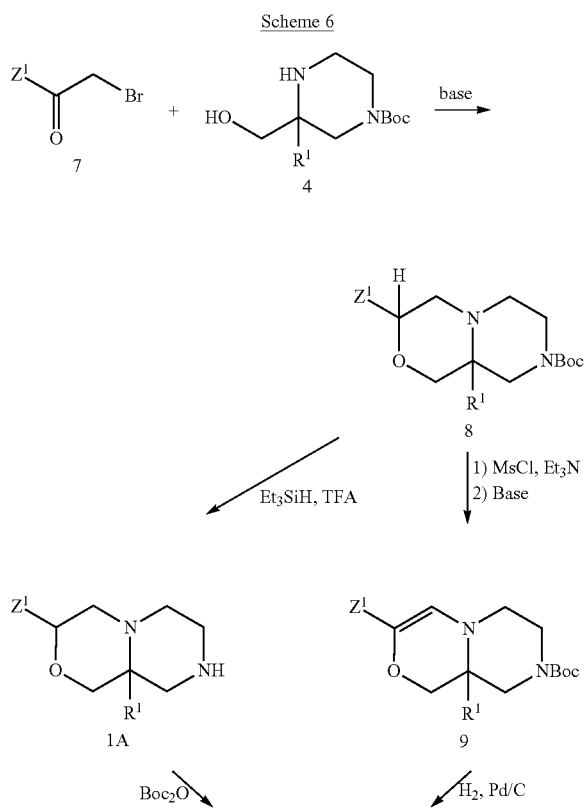

Alternatively, a subclass of intermediates 1, piperazines 1B, can be prepared as described in Scheme 7. The Boc protective group of intermediates 5 (prepared as described in Scheme 5) is switched to benzyl carbamate (Cbz) groups by initial treatment with an acid such as TFA or HCl, followed by coupling with benzyl chloroformate in the presence of a base such as triethylamine. The resulting Cbz-piperazine diols 5A are converted to the corresponding dichloro intermediates by heating with thionyl chloride; then, the dichlorides are heated with allylamine in the presence of sodium iodide to afford the allyl substituted fused piperazines 10. The allyl groups may be removed in several ways, including by warming with 1,3-dimethylpyrimidine-2,4,6(1H,3H,5H)-trione in the presence of a catalyst such as palladium tetrakis triphenylphosphine. The revealed amines are then re-protected with tert-butoxycarbamate groups by treatment with Boc₂O to provide intermediates 6B, generally as mixtures of cis and trans isomers. The cis and trans isomers can be separated as described in Scheme 5 by silica chromatography or by chiral preparative HPLC. If intermediates 5 are prepared from single enantiomers of 4 (as described in Scheme 5), then the resulting intermediates 6B (cis) and 6B (trans) are also single isomers. Alternatively, separation of the cis and trans isomers can be performed at an earlier stage by separation of the cis/trans isomers of intermediates 10. The Cbz protective groups of intermediates 6B (cis) and 6B (trans) can be removed, for example, by hydrogenolysis in the presence of a catalyst such as palladium on carbon to afford intermediates 1B (cis) and 1B (trans).

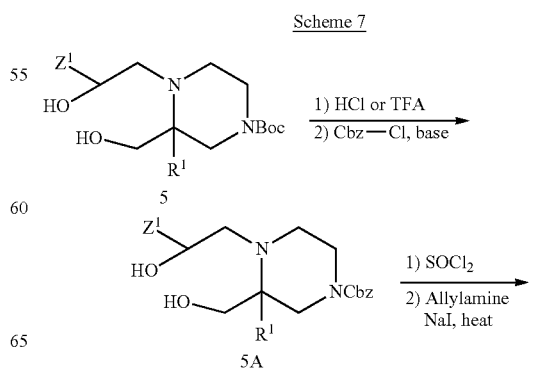

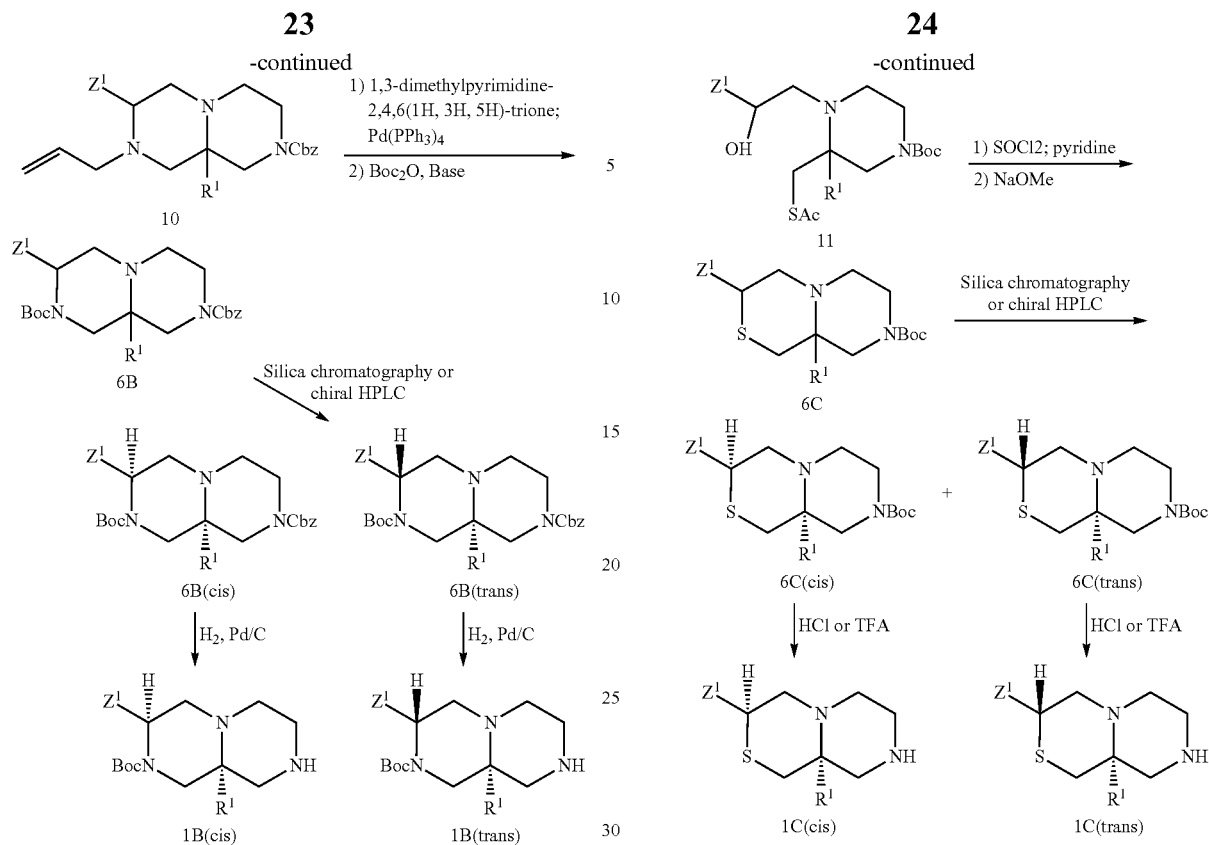

Alternatively, a sub-class of intermediates 1 (IC) may be prepared according to Scheme 8. Diols 5 are initially converted to their corresponding mono-mesylates by treatment with mathanesulfonyl chloride, a base such as triethyl amine, and a catalyst such as 4-dimethylaminopyridine. Subsequent reaction with potassium thioacetate in a solvent such as dimethyl sulfoxide (DMSO) provides intermediates 11. The remaining hydroxyl group of 11 is then converted to the corresponding chloro intermediate by treatment with, for example, thionyl chloride, followed by addition of a base such as pyridine. The resulting chloro intermediate is then treated with sodium methoxide to afford the cyclized sulfides 6C. When the starting diols 5 used are single isomers (starting from enantiomerically pure epoxides 3 and enantiomerically pure hydroxyalkylpiperazines 4 (Scheme 2), the resulting intermediates 6C may be obtained as single isomers. Alternatively, when racemic epoxides 3, and single enantiomer hydroxyalkylpiperazines 4 are employed, the resulting intermediates 6C are obtained as a mixture of two isomers (cis and trans), which can then be separated to single isomers 6C (cis) and 6C (trans) by silica chromatography or by chiral preparative HPLC. Removal of the tert-butyl carbamate protective group can then be achieved by treatment with an acid such as TFA or HCl to provide the piperazines 1C (cis) and 1C (trans).

Scheme 8

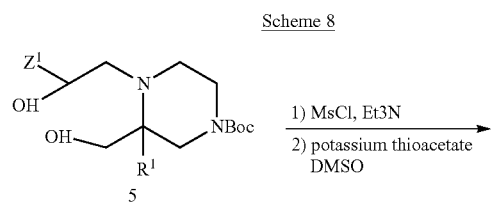

Epoxides 2 and 2-3 may be prepared by a variety of methods. One approach is described in Scheme 9. Aryl halides or triflates (bromides 12 and 12a shown) may be coupled to form alkene products 13 and 13a in a number of ways, for example by Heck reaction or by reaction with vinyl tetrafluoroborate (Molander, G.; Luciana, A. Journal of Organic Chemistry, 2005, 70(10), 3950-3956) under palladium catalyzed coupling conditions with an appropriate phosphine ligand (Molander, G.; Brown, A. Journal of Organic Chemistry, 2006, 71(26), 9681-9686). The alkenes 13 and 13a can then be converted to the corresponding epoxides 2-3 and 2 in several ways, including by treatment with meta-chloroperoxybenzoic acid (Fringuelli, F. et al. Organic Preparations and Procedures International, 1989, 21(6), 757-761). Epoxides 2, can be separated into single enantiomers 2-2 and 2-1 by HPLC employing a chiral column.

Scheme 9

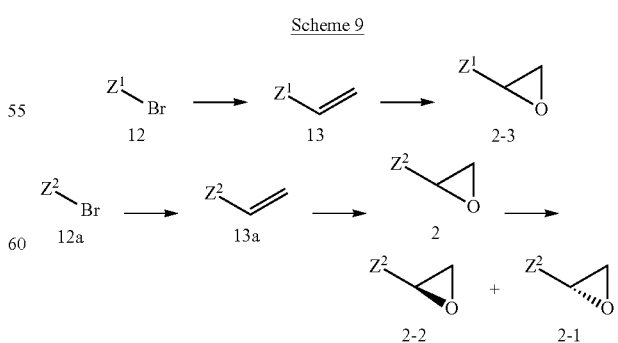

Bromomethylketones 7 may be prepared in a variety of ways; one route is depicted in Scheme 10. According to the Scheme, aryl halides or triflates (bromide 12 shown) can be reacted with tributyl(1-ethoxyvinyl)tin in the presence of a metal catalyst such as $PdCl_2(PPh_3)_2$ to provide an intermediate ethylenolether. This is subsequently treated in the same reaction vessel with N-bromosuccinimide (NBS) with added tetrahydrofuran and water to provide bromomethylketones 7. Chloromethyl ketones can similarly be prepared by employing N-chlorosuccinimide in place of N-bromosuccinimide.

Scheme 10

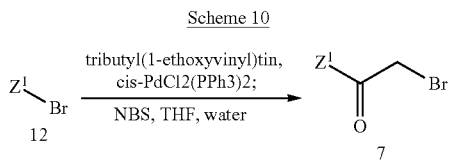

Aldehydes or ketones 3 may be prepared in a wide variety of ways, with a number of options depicted in the intermediate examples herein. Scheme 11 describes one method that makes use of epoxides 2-4 (prepared in a similar fashion as described in Scheme 9). According to Scheme 11, epoxides 2-4 are subjected to hydrogenolysis, using for example, hydrogen gas and a catalyst such as Pd on carbon, to afford hydroxymethyl intermediates 14. Subsequent oxidation to aldehydes or ketones 3 can be accomplished in many ways as known to the chemist. For example, oxidation can be achieved by treatment with Dess-Martin periodinane or by Swern oxidation.

Scheme 11

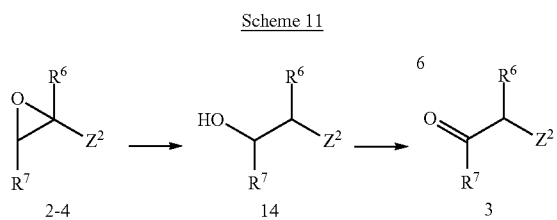

Scheme 12 shows several alternative routes for making aldehydes (sub-family 3-1). Aryl halides or triflates (bromide shown, 12a) may be reacted with allyltributylstananes in the presence of a catalyst (such as palladium tetrakis triphenylphosphine) to afford allyl intermediates 15. These may be subjected to oxidative cleavage to afford aldehydes 3-1 using one of several methods, such as treatment with osmium tetroxide and sodium periodate, or by reaction with ozone followed by dimethylsulfide. Alternatively, 12a may be reacted with bromo(1,3-dioxolan-2-ylmethyl)zinc reagents 16 in the presence of palladium(II) acetate and tri-t-butylphosphine-$BF_4$ complex to afford intermediates 17. These, in turn, may be hydrolyzed using for example HCl in a water dioxane mixture to afford aldehydes 3-1.

Scheme 12

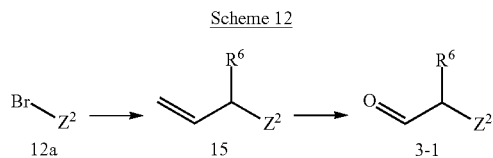

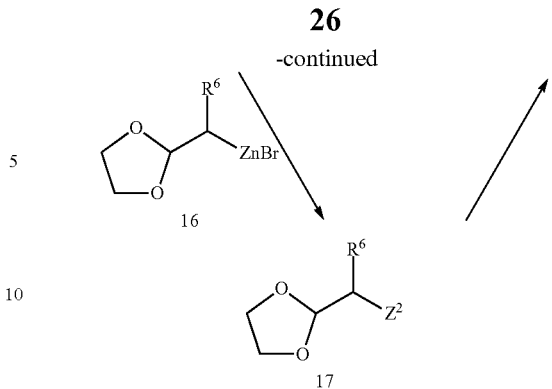

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry.

The following examples are provided for the purpose of further illustration only and are not intended to be limitations on the disclosed invention.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure.

Flash chromatography was usually performed using a Biotage Flash Chromatography apparatus (Dyax Corp.) on silica gel (32-63 mM, 60 Å pore size) in pre-packed cartridges of the size noted.

Chiral analytical chromatography was usually performed on one of Chiralpak AS, Chiralpak AD, Chiralpak IC, Chiralcel OD, Chiralcel IA, or Chiralcel OJ columns (250× 4.6 mm) (Daicel Chemical Industries, Ltd.) with noted percentage of either ethanol in hexane (% Et/Hex) or isopropanol in heptane (% IPA/Hep) as isocratic solvent systems.

Chiral preparative chromatography was sometimes conducted on one of Chiralpak AS, Chiralpak AD, Chiralpak IC, Chiralcel OD, Chiralcel IA, or Chiralcel OJ columns (20× 250 mm) (Daicel Chemical Industries, Ltd.) with desired isocratic solvent systems identified on chiral analytical chromatography or by supercritical fluid (SFC) conditions.

$^1$H NMR spectra were acquired at 500 MHz spectrometers in CDCl$_3$ solutions unless otherwise noted. Chemical shifts were reported in parts per million (ppm). TMS was used as internal reference in CD$_3$Cl solutions, and residual CH$_3$OH peak or TMS was used as internal reference in CD$_3$OD solutions. Coupling constants (J) were reported in hertz (Hz).

Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Abbreviations and acronyms which may be used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); t-butyloxycarbonyl (Boc or BOC); di-t-butyl dicarbonate ((BOC)$_2$O, Boc$_2$O); benzyloxycarbonyl (Cbz); Cyclopentyl methyl ether (CPME); Carbonyldiimidazole (CDI); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); dimethoxyethane (DME); Diisobutylaluminium hydride (DIBAL-H); N,N-diisopropylethylamine (DIEA, DIPEA, Hunig's base); di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3(1H)-one); dimethylsulfide (DMS); dimethylsulfoxide (DMSO); N;N-dimethylformamide (DMF); 4-dimethylaminopyridine (DMAP); dimethylacetamide (DMA; DMAC); 1,3-Bis(diphenylphosphino)propane (DPPP); ethyl acetate (EtOAc); diethyl ether (ether or Et$_2$O); 1-ethyl-3-(3-dimethylaminopropyl)carbodiimide (EDC, EDAC or EDCI); 2-(7-Aza-1H-benzotriazole-1-yl)-1,1,3,3-tetramethyluronium hexafluorophosphate (HATU); hexane (Hex); hexamethylphosphoramide (HMPA); 1-Hydroxybenzotriazole hydrate (HOBt); isopropanol (IPA); isopropyl acetate (IPAc); Potassium bis(trimethylsilyl)amide (KHMDS); lithium aluminum hydride (LAH); lithium diisopropylamide (LDA); 3-chloroperoxybenzoic acid (mCPBA); methanol (MeOH); CH$_3$SO$_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hexamethyldisilazide (NaHMDS); sodium triacetoxyborohydride (NaBH(OAc)$_3$); Pyridinium chlorochromate (PCC); phenyl (Ph); petroleum ether (PE or petrol ether); tetrakis(triphenylphosphine)palladium (Pd(PPh$_3$)$_4$); tris(dibenzylidineacetone)dipalladium (Pd$_2$(dba)$_3$); Pd(dppf)Cl$_2$ or PdCl$_2$(dppf) is 1,1'-Bis(diphenylphosphino)ferrocene]dichloropalladium(II) which may be complexed with CH$_2$Cl$_2$; tetra-n-butylammonium fluoride (TBAF); tert-butyldimethylsilyl chloride (TBS-Cl); triethylamine (TEA); trifluoroacetic acid (TFA); —SO$_2$CF$_3$ (Tf); trifluoromethanesulfonic acid (triflic acid, TfOH); trifluoromethanesulfonic anhydride (triflic anhydride, (Tf)$_2$O); 2-tetrahydrofuran (THF); N,N,N',N'-Tetramethylethylenediamine (TMEDA); tetramethylsilane (TMS); p-toluenesulfonic acid (TsOH); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t. or RT); hour(s) (h or hr); minute(s) (min); retention time (R$_t$); gram(s) (g); milligram(s) (mg); milliliter(s) (mL); microliter(s) (L); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention. It is understood that a chiral center in a compound may exist in the "S" or "R" stereoconfigurations, or as a mixture of both. In some examples, compounds having a chiral center were separated into single stereoisomers (for example, referred to as Isomer A and Isomer B, or faster/slower eluting isomers), or each was derived synthetically from a single isomer intermediate. Except for a defined chiral center in the parent mixture, absolute stereochemistry (R or S) of each of the separated isomers was not determined, unless specifically noted otherwise.

Intermediates described below may be referred to herein by their number preceded by "I-". For example, Intermediate 2 is shortened to I-2.

INTERMEDIATE 1

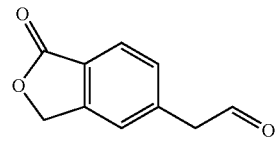

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo (1,3-dioxolan-2-ylmethyl)zinc solution (1.03 L, 516 mmol) was added via cannula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methylTHF (2 L) and brine were added, and the mixture was stirred for 5 min. The layers were separated and the aqueous layer was extracted again with 2-methylTHF. The organic layers were combined, washed three times with brine (4 L each), dried over MgSO₄, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one. LC-MS (IE, m/z): 221 [M+1]⁺.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. LC-MS (IE, m/z): 177 (M+1)⁺.

INTERMEDIATE 2

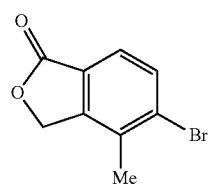

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. ¹H NMR (500 MHz, CDCl₃) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of thallium trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE® pad, washed with EtOAc, adsorbed onto silica and purified by silica gel chromatography to afford title compound. ¹H-NMR (500 MHz, CDCl₃) δ ppm 7.71 (d, J=8.0 Hz, 1H), 7.58 (d, L=8.0 Hz, 1H), 5.25 (s, 2H), 237 (s 3H).

INTERMEDIATE 3

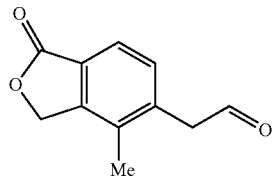

(4-Methyl-1-oxo-1,3-dihydro-2-benzofuran-5-yl)acetaldehyde

Step A: 4-Methyl-5-prop-2-en-1-yl-2-benzofuran-1(3H)-one

To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh₃)₄ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step B: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford the title compound. ¹H-NMR (500 MHz, CDCl₃) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

INTERMEDIATE 4

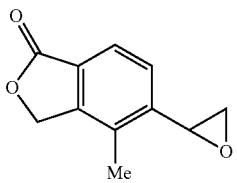

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmol), PdCl$_2$(dppf)-CH$_2$Cl$_2$Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% EtOAc/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-MS: M+1=191.

INTERMEDIATES 4A AND 4B (Method 1)

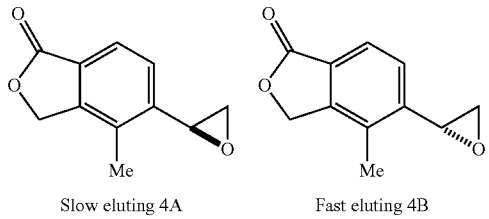

Slow eluting 4A     Fast eluting 4B

4A: 4-methyl-5-[(2S)-oxiran-2-yl]-2-benzofuran-1(3H)-one

4B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 4B) eluted first, and the slow epoxide (4-methyl-5-[(2S)-oxiran-2-yl]-2-benzofuran-1(3H)-one, 4A) eluted second.

Alternatively, the resolution could also be achieved using a mobile phase of 8% MeOH/98% CO$_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 4B and by Mosher ester and Trost ester HNMR analysis of esters made starting from 4B. Both epoxide isomers find utility in the present invention.

INTERMEDIATE 4B (Method 2)

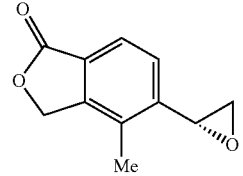

4-methyl-5-[(2R)-oxiran-2-yl]-2-benzofuran-1(3H)-one

Step A: 3-hydroxymethyl-2-methyl phenol

To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-d$_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL)

and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C:
5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through solka flok and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one. $^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D:
4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over SOLKA FLOC®, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one. $^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzo-furan-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The crystalline solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

INTERMEDIATE 5

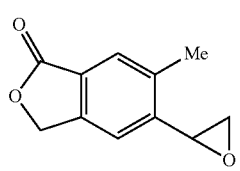

6-methyl-5-oxiran-2-yl-2-benzofuran-1(3H)-one

Step A: 5-prop-2-en 1-yl-2-benzofuran-1(3H)-one: A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and Pd(PPh$_3$)$_4$ (1.2 g, 1.0 mmol) in 100 mL toluene was heated under N$_2$ at 90-100° C. overnight. After cooling to r.t., the mixture was diluted with 250 mL EtOAc and filtered. The filtrate was washed with water and brine, dried over anhydrous Na$_2$SO$_4$ and concentrated to dryness. The residue was purified via column (DCM/Petrol Ether=1:5) to give the title compound.

Step B: 5-(2-hydroxyethyl)-2-benzofuran-1(3H)-one

To a solution of 5-prop-2-en-1-yl-2-benzofuran-1(3H)-one (13.5 g, 45.2 mmol) in 200 mL DCM/MeOH (V/V=1:1) was bubbled O$_3$ at −78° C. for 30 min, and N$_2$ was bubbled for another 15 min at −78° C. Then 20 mL of Me$_2$S were added, and the mixture was stirred at r.t. overnight before concentrating to dryness. The residue was dissolved in MeOH (100 mL) and then cooled to 0° C. NaBH$_4$ (5.90 g, 155 mmol) was added in portions. The resulting mixture was stirred at 0° C. for 1 h, then quenched with citric acid (aq.) and extracted three times with EtOAc. The combined organic layers were washed with NaHCO$_3$ (aq.) and brine, dried over anhydrous Na$_2$SO$_4$ and concentrated to dryness. The residue was purified via column chromatography (EtOAc/Petrol Ether=1:5) to give the title compound. $^1$H-NMR (400 MHz, CDCl$_3$) δ ppm 7.86 (d, J=7.8 Hz, 1H), 7.41 (d, J=7.8 Hz, 1H), 7.38 (s, 1H), 5.29 (s, 2H), 3.92-3.98 (m, 2H), 3.01 (t, J=6.4 Hz, 2H).

Step C: 5-(2-hydroxyethyl)-6-iodo-2-benzofuran-1(3H)-one

To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted three times with 500 mL of EtOAc and the combined organic layers were washed with saturated NaHCO$_3$ and brine, dried over anhydrous sodium sulfate, filtered and concentrated. The residue was purified by column chromatography (EtOAc/Petrol Ether=1:5) to give the desired 5-(2-hydroxyethyl)-6-iodo-2-benzofuran-1(3H)-one and regioisomer by-product 5-(2-hydroxyethyl)-4-iodo-2-benzofuran-1(3H)-one. $^1$H-NMR (400 MHz, CDCl$_3$) δ ppm 7.84 (d, J=7.8 Hz, 1H), 7.46 (d, J=7.8 Hz, 1H), 5.09 (s, 2H), 3.93 (q, J=6.3 Hz, 2H), 3.16 (t, J=6.3 Hz, 2H), 1.45 (t, J=5.5 Hz, 1H).

Step D: 5-(2-hydroxyethyl)-6-methyl-2-benzofuran-1(3H)-one

To a flask charged with 5-(2-hydroxyethyl)-6-iodo-2-benzofuran-1(3H)-one (6.00 g, 19.7 mmol) and a stir bar was added Pd$_2$(dba)$_3$ (452 mg, 0.493 mmol), PPh$_3$ (1 g, 4 mmol) and NMP (50 mL). The mixture was purged with N$_2$ and heated to 50° C. for 10 min, followed by addition of CuI (375 mg, 1.97 mmol). After the mixture was heated for another 10 min, Sn(CH$_3$)$_4$ (5.30 g, 29.6 mmol) was added into the reaction, and it was heated to 120° C. for 2 h. After cooling to room temperature, the mixture was diluted with saturated NH$_4$Cl (200 mL) and extracted with EtOAc (3 times 200 mL). The combined organic layers were washed with water and brine, dried over anhydrous sodium sulfate, filtered and concentrated. The residue was purified by prep-HPLC to give the title compound. $^1$H-NMR (400 MHz, CDCl$_3$) δ ppm 7.72 (s, 1H), 7.33 (s, 1H), 5.27 (s, 2H), 3.93 (t, J=6.3 Hz, 2H), 3.01 (t, J=6.3 Hz, 2H), 2.44 (s, 3H).

Step E: 2-(6-methyl-1-oxo-1,3-dihydro-2-benzofuran-5-yl)ethyl methanesulfonate

To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness. The collected title compound was used for the next step without any purification.

Step F: 5-ethenyl-6-methyl-2-benzofuran-1(3H)-one

To a mixture of 2-(6-methyl-1-oxo-1,3-dihydro-2-benzofuran-5-yl)ethyl methanesulfonate (2.00 g, 7.41 mmol) and TEA (5 mL) in DCM (50 mL) was added DBU (5 mL) slowly at 0° C. The mixture was stirred at r.t. overnight, and then was diluted with 50 mL of DCM, washed with 2 N HCl in three times and brine. The organic layer was dried and concentrated to dryness. The residue was purified by prep-TLC to give 5-ethenyl-6-methyl-2-benzofuran-1(3H)-one.

Step G: 6-methyl-5-oxiran-2-yl-2-benzofuran-1(3H)-one

To a solution of 5-ethenyl-6-methyl-2-benzofuran-1(3H)-one (1.00 g, 5.75 mmol) in 50 mL of DCM was slowly added mCPBA (3.50 g, 17.4 mmol) in 50 mL of DCM at 0° C. The mixture was warmed to room temperature, and stirred for 2 days. The mixture was washed with aqueous $Na_2SO_3$ until KI indicator paper didn't change color. The organic layer was washed with brine and then concentrated. The residue was purified via silica column to give the title compound. LC-MS M+1 (calc. 191. found 191).

INTERMEDIATE 6

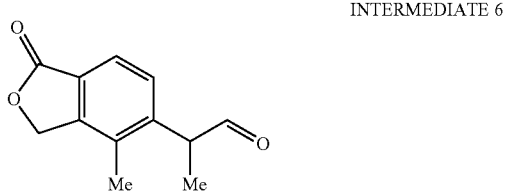 [SMILES: Cc1c(C(C)C=O)ccc2c1COC2=O]

2-(4-Methyl-1-oxo-1,3-dihydro-2-benzofuran-5-yl)propanal

Step A: 4-Methyl-5-prop-2-en-1-yl-2-benzofuran-1(3)-one

A mixture of 5-bromo-4-methyl-2-benzofuran-1(3H)-one (980 mg, 4.3 mmol), allyl-tributyl-stannane (1.7 g, 5.2 mmol), LiCl (550 mg, 12.9 mmol) and $Pd(PPh_3)_4$ (0.1 g) in anhydrous toluene was stirred at reflux under $N_2$ overnight. The solvent was removed under reduced pressure, and the residue was purified with silica gel column chromatography to give the product 4-methyl-5-prop-2-en-1-yl-2-benzofuran-1(3H)-one.

Step B: (4-Methyl-1-oxo-1,3-dihydro-2-benzofuran-5-yl)acetic acid

To a stirred solution of 4-methyl-5-prop-2-en-1-yl-2-benzofuran-1(3H)-one (2.10 g, 11.2 mmol) in $CCl_4$ (50 mL), acetonitrile (50 mL) and water (75 mL) was added sodium periodate (12 g, 55.8 mmol) and ruthenium oxide hydrate (210 mg) and the resulting mixture was stirred at ambient temperature overnight. The mixture was diluted with 100 mL DCM and 100 mL of water. The organic layer was dried over anhydrous sodium sulfate and concentrated. The residue was purified with silica gel column chromatography to afford the title compound.

Step C: 1,1-Dimethylethyl (4-methyl-1-oxo-1,3-dihydro-2-benzofuran-5-yl)acetate

To a solution of (4-methyl-1-oxo-1,3-dihydro-2-benzofuran-5-yl)acetic acid (100 mg, 0.48 mmol) in anhydrous DCM (10 mL) was added 1,1-dimethylethyl-N,N-bis(1-methylethyl)imidocarbamate (485 mg, 2.50 mmol) dropwise at 0° C. under $N_2$. Then the mixture was stirred at r.t. over night. The mixture was filtered and the filtrate was washed with 2N HCl and brine, dried over anhydrous sodium sulfate and concentrated. The residue was purified by preparative TLC to give 1,1-dimethylethyl (4-methyl-1-oxo-1,3-dihydro-2-benzofuran-5-yl)acetate. $^1$H-NMR (400 MHz, $CDCl_3$) δ ppm 7.70 (d, J=7.8 Hz, 1H), 7.38 (d, J=7.0 Hz, 1H), 5.25 (s, 2H), 3.67 (s, 3H), 2.27 (s, 3H), 1.44 (s, 9H).

Step D: 1,1-Dimethylethyl-2-(4-methyl-1-oxo-1,3-dihydro-2-benzofuran-5-yl)propanoate A solution of 1,1-dimethylethyl (4-methyl-1-oxo-1,3-dihydro-2-benzofuran-5-yl)acetate (770 mg, 3.1 mmol) in 30 mL of anhydrous THF was cooled to −78° C. NaHMDS (4.0 mmol) was added to the reaction dropwise at −78° C. After the addition, the mixture was stirred at −78° C. for 1 h and then $CH_3I$ (462 mg, 3.20 mmol) was added dropwise at −78° C. The reaction was warmed to room temperature slowly and stirred at ambient temperature over night. The reaction was quenched with $NH_4Cl$ solution, and extracted with EtOAc. The organic layer was washed with brine, dried over anhydrous sodium sulfate and concentrated. The residue was purified via preparative TLC to afford 1,1-dimethylethyl-2-(4-methyl-1-oxo-1,3-dihydro-2-benzofuran-5-yl)propanoate. $^1$H-NMR (400 MHz, $CDCl_3$) δ ppm 7.67 (d, J=7.8 Hz, 1H), 7.37 (d, J=7.8 Hz, 1H), 5.19 (s, 2H), 3.80 (dd, J=7.0 Hz, 1H), 2.24 (s, 3H), 1.40 (d, J=7.0 Hz, 1H), 1.32 (s, 9H).

Step E: 2-(4-Methyl-1-oxo-1,3-dihydro-2-benzofuran-5-yl)propanoic acid

To a solution of 1,1-dimethylethyl-2-(4-methyl-1-oxo-1,3-dihydro-2-benzofuran-5-yl)propanoate (400 mg, 1.4 mmol) in 10 mL of anhydrous DCM was added TFA (2.5 mL) dropwise at r.t. Then the mixture was stirred for 1 hour. The solvent was removed under vacuum to give the crude title compound, which was used for next step without purification.

Step F: 5-(2-Hydroxy-1-methylethyl)-4-methyl-2-benzofuran-1(3H)-one

To a solution of 2-(4-methyl-1-oxo-1,3-dihydro-2-benzofuran-5-yl)propanoic acid (300 mg, 1.4 mmol) in 18 mL of anhydrous THF was added $BH_3$-THF (2 mL, 2 mmol) dropwise at 0° C. Then the mixture was warmed to room temperature slowly and then stirred for 3 hours. Then the mixture was quenched with MeOH and the solvent was removed under vacuum. The residue was the purified via prep-TLC to give 5-(2-hydroxy-1-methylethyl)-4-methyl-2-benzofuran-1(3H)-one. $^1$H-NMR (400 MHz, $CDCl_3$) δ ppm 7.73 (d, J=7.8 Hz, 1H), 7.40 (d, J=7.8 Hz, 1H), 5.23 (s, 2H), 3.77 (d, J=7.0 Hz, 2H), 3.36-3.42 (m, 1H), 2.30 (s, 3H), 1.27 (d, J=7.0 Hz, 3H).

Step G: 2-(4-Methyl-1-oxo-1,3-dihydro-2-benzofuran-5-yl)propanal 5-(2-Hydroxy-1-methylethyl)-4-methyl-2-benzofuran-1(3H)-one (161 mg, 0.781 mmol, 1.0 eq) was dissolved in DCM (6 ml). To above solution was added Dess-Martin Periodinane (397 mg, 0.937 mmol, 1.2 eq). The mixture was stirred at rt for 2 hr. To the reaction was added DCM (10 mL), Na$_2$S$_2$O$_3$ (6 mL) and H$_2$O (6 mL). The mixture was stirred at r.t. for 30 minutes and formed two layers. The bottom layer was separated and washed with aqueous NaHCO$_3$, brine and water, dried over Na$_2$SO$_4$, filtered, and concentrated to dryness. The crude product was used to next step without purification. $^1$H NMR (500 MHz, CDCl$_3$, δ in ppm): 9.70 (1H, s, CHO), 7.79 (1H, d, J=7.8 Hz), 7.28 (1H, d, J=7.8 Hz), 5.28 (2H, s), 3.27 (1H, m), 2.32 (3H, s), 1.50 (3H, d, J=7.2 Hz).

INTERMEDIATE 7

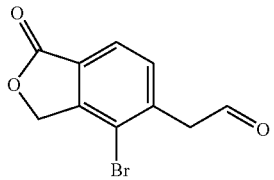

(4-bromo-1-oxo-1,3-dihydro-2-benzofuran-5-yl)acetaldehyde

Step A: 4,5-dibromo-2-benzofuran-1(3H)-one

To a flask containing a stir bar was added 5-bromo-2-benzofuran-1(3H)-one (12.0 g, 56.3 mmol) and NBS (15 g, 84 mmol). Triflic acid (50 mL) was then added at 0° C. and the resulting mixture was allowed to warm to rt and stir for 2 days. TLC analysis of the reaction mixture showed complete reaction. The reaction mixture was poured into ice and the organic layer was separated, washed with brine, water, dried over Na$_2$SO$_4$, filtered, and concentrated. The residue was then absorbed into silica gel and subjected for purification by MPLC column to give title compound. LC-MS (IE, m/z): 291 [M+1]$^+$.

Step B: 5-allyl-4-bromo-2-benzofuran-1(3H)-one

To a flask charged with 4,5-dibromo-2-benzofuran-1(3H)-one (170 mg, 0.59 mmol) and a stir bar was added allyl tri-n-butyltin (0.18 mL, 0.59 mmol), palladium tetrakis (68 mg, 0.059 mmol), lithium chloride (50 mg, 1.2 mmol), and toluene (5 mL). The mixture was sealed with a condenser, purged three times with nitrogen, and heated to reflux for 16 hours. The reaction was diluted with EtOAc (50 mL), adsorbed onto silica gel, and purified by silica gel flash chromatography to afford title compound. LC-MS (IE, m/z): 253 [M+1]$^+$;

Step C: (4-bromo-1-oxo-1,3-dihydro-2-benzofuran-5-yl)acetaldehyde

To a solution of 5-allyl-4-bromo-2-benzofuran-1(3H)-one (120 mg, 0.47 mmol) in methanol (20 mL) was bubbled ozone at −78° C. until the solution turned light blue. Excess ozone was removed by bubbling nitrogen through, which was followed by addition of dimethyl sulfide (0.35 mL, 4.7 mmol). The reaction was allowed to warm to RT, diluted with EtOAc, washed with brine, adsorbed onto silica gel, and purified by MPLC. Removal of solvent provided the title compound.

INTERMEDIATE 8

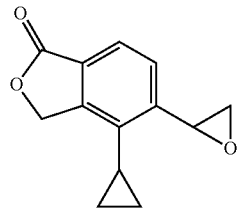

4-cyclopropyl-5-oxiran-2-yl-2-benzofuran-1(3H)-one

Step A: 5-bromo-4-iodo-2-benzofuran-1(3H)-one

To a cooled (0° C.) solution of 5-bromo-2-benzofuran-1(3H)-one (50 g, 0.235 mol) in trifluoromethanesulfonic acid (400 mL) was added N-iodosuccinimide (55.5 g, 0.247 mol). The resulting mixture was stirred at room temperature overnight, then poured slowly into ice water (2 L), filtered and the filtrate extracted with EtOAc. The combined organic layers were washed with water and brine, dried and concentrated to give 5-bromo-4-iodo-2-benzofuran-1(3H)-one.

Step B: 5-bromo-4-vinyl-2-benzofuran-1(3H)-one

A mixture of 5-bromo-4-iodo-2-benzofuran-1(3H)-one (1 g, 2.95 mmol), potassium vinyltrifluoroborate (474 mg, 3.54 mmol) and Pd(dppf)Cl$_2$ (200 mg) in 20 mL of TEA and 20 mL of EtOH was heated to reflux under N$_2$ for 2 hours. Most of the solvent was removed, and the residue was dissolved in EtOAc (100 mL). The solution was washed with 0.1 N HCl, sodium bicarbonate, and brine, dried over sodium sulfate, filtered and concentrated to provide the title compound.

Step C: 5-bromo-4-cyclopropyl-2-benzofuran-1(3H)-one

To a cooled (0° C.) mixture of 5-bromo-4-vinyl-2-benzofuran-1(3H)-one (2.2 g, 9.21 mol) and Pd(OAc)$_2$ (100 mg) in EtOAc (50 mL) was added a solution of CH$_2$N$_2$ in ether (100 mL) slowly. The resulting mixture was stirred at room temperature overnight, then quenched with acetic acid, filtered and the filtrate washed with water and brine, dried and concentrated to provide the title compound.

Step D: 4-cyclopropyl-5-vinyl-2-benzofuran-1(3H)-one

A mixture of 5-bromo-4-cyclopropyl-2-benzofuran-1(3H)-one (760 mg, 3.004 mmol), potassium vinyltrifluoroborate (805 mg, 6.008 mmol) and Pd(dppf)Cl$_2$ (100 mg) in 20 mL of TEA and 20 mL of EtOH was heated to reflux under N$_2$ for 8 hours. When TLC showed complete reaction most of the solvent was removed, and the residue was dissolved in EtOAc (100 mL). The solution was washed with 0.1 N HCl, sodium bicarbonate, and brine, dried over sodium sulfate, filtered and concentrated. The resulting oil was purified by column chromatography to give 4-cyclopropyl-5-vinyl-2-benzofuran-1(3H)-one.

Step E: 4-cyclopropyl-5-oxiran-2-yl-2-benzofuran-1(3H)-one

To a solution of 4-cyclopropyl-5-vinyl-2-benzofuran-1(3H)-one (440 mg, 2.2 mmol) in 50 mL of DCM was slowly added mCPBA (1.14 g, 6.6 mmol) in 50 mL of DCM at 0° C. After warming to room temperature, the mixture was stirred for 12 hours. The mixture was washed with aqueous Na$_2$SO$_3$ until potassium iodide (KI) indicator paper did not change color. The organic layers were combined, washed with brine and then concentrated. The residue was purified via prep-TLC to give the title compound: $^1$H-NMR (400 MHz, CDCl$_3$) δ ppm 7.77 (d, J=8.6 Hz, 1H), 7.39 (d, J=7.8 Hz, 1H), 5.39 (s, 2H), 4.43-4.45 (m, 1H), 3.26-3.28 (m, 1H), 2.68-2.70 (m, 1H), 1.94-2.01 (m, 1H), 1.08-1.12 (m, 2H), 0.65-0.75 (m, 2H)

INTERMEDIATE 9

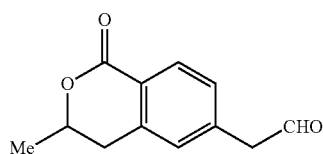

(3-methyl-1-oxo-3,4-dihydro-1H-isochromen-6-yl) acetaldehyde

Step A: 6-Bromo-3-methyl-3,4-dihydro-1H-isochromen-1-one

A solution of diisopropylamine (13 ml, 93 mmol)) in THF (155 ml) at −78° C. was treated with n-BuLi (1.6M in Hexanes; 58 ml, 93 mmol) over a period of 15 minutes using a syringe pump. In a separate flask, a solution of 2-methyl-4-bromo benzoic acid (10 g, 46 mmol) and HMPA (8.3 ml, 46 mmol) in THF (155 ml) was cooled to −78° C. Methyl lithium (29 ml, 46 mmol) was added slowly via syringe to the cooled solution in order to make the lithio carboxylate. The resulting solution was stirred for 10 minutes and then transferred via cannula to the LDA solution at −78° C. The resulting solution was stirred at −78° C. for an additional 1 hour before being quenched with anhydrous acetaldehyde (7.9 ml, 140 mmol) and the reaction was then taken out of the dry ice acetone bath and allowed to stir for an additional 1 hour. The flask containing the reaction mixture was then resubmerged in the dry ice acetone bath before it was quenched with 4M HCl in dioxane (50 mL) followed by 25 mL of MeOH. The reaction was stirred at room temp for an additional 1 hour. The crude reaction was partitioned between 200 mL EtOAc and 200 mL water. The organic layer was washed with water, brine, dried with magnesium sulfate, filtered and concentrated. Purification via MPLC (30-70% DCM/Hexanes) afforded 6-bromo-3-methyl-3,4-dihydro-1H-isochromen-1-one. LC-MS (IE, m/z): 241 [M+1]$^+$.

Step B: 6-(1,3-Dioxolan-2-ylmethyl)-3-methyl-3,4-dihydro-1H-isochromen-1-one

A sealed tube was charged with aryl bromide, palladium (II) acetate (0.028 g, 0.12 mmol) and tri-t-butylphosphine-BF$_4$ complex (0.072 g, 0.249 mmol) and sealed. The tube was evacuated and refilled with nitrogen before DMF (12 ml) and 6-bromo-3-methyl-3,4-dihydro-1H-isochromen-1-one (0.75 g, 3.1 mmol) were added followed by bromo(1,3-dioxolan-2-ylmethyl)zinc (6.2 ml, 3.1 mmol). The tube was heated to 110° C. in the microwave for 75 minutes, after which it was cooled, diluted with EtOAc, filtered, concentrated and purified via MPLC (20-50% EtOAc/Hexanes) to afford the title compound. LC-MS (IE, m/z): 249 [M+1]$^+$.

Step C: (3-methyl-1-oxo-3,4-dihydro-1H-isochromen-6-yl)acetaldehyde

A 1:1 solution of dioxane:3N HCl was added to a flask containing of 780 mg (3.2 mmol) of 6-(1,3-dioxolan-2-ylmethyl)-3-methyl-3,4-dihydro-1H-isochromen-1-one. The reaction was then stirred at RT overnight. The crude reaction mixture was then partitioned between water and DCM. The organic layer was washed with saturated sodium bicarbonate solution, followed by brine. The organic layer was then dried with magnesium sulfate, filtered and concentrated to afford the title compound.

INTERMEDIATE 9A

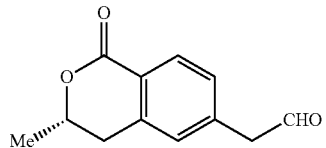

(3S)-3-methyl-1-oxo-3,4-dihydro-1H-isochromen-6-yl]acetaldehyde

Step A: (3S)-6-Bromo-3-methyl-3,4-dihydro-1H-isochromen-1-one

Chiral SFC-HPLC separation of racemic 6-bromo-3-methyl-3,4-dihydro-1H-isochromen-1-one was achieved using ChiralPak AS 4.6×250 mm 10 u column, eluting with 60% IPA/Heptane. The faster eluting isomer was identified as the S-isomer. LC-MS (IE, m/z): 241 [M+1]$^+$.

Step B: (3S)-6-(1,3-Dioxolan-2-ylmethyl)-3-methyl-3,4-dihydro-1H-isochromen-1-one The title compound was obtained using the procedure described for the synthesis of 6-(1,3-dioxolan-2-ylmethyl)-3-methyl-3,4-dihydro-1H-isochromen-1-one utilizing (3S)-6-bromo-3-methyl-3,4-dihydro-1H-isochromen-1-one as the starting material. LC-MS (IE, m/z): 249 [M+1]$^+$.

Step C: (3S)-3-methyl-1-oxo-3,4-dihydro-1H-isochromen-6-yl]acetaldehyde

The title compound was obtained using the procedure described for the synthesis of (3-methyl-1-oxo-3,4-dihydro-1H-isochromen-6-yl)acetaldehyde utilizing (3S)-6-(1,3-dioxolan-2-ylmethyl)-3-methyl-3,4-dihydro-1H-isochromen-1-one.

(3R)-3-methyl-1-oxo-3,4-dihydro-1H-isochromen-6-yl]acetaldehyde (Intermediate 9B) can be prepared following the procedure for making I-9A, except using (3R)-6-bromo-3-methyl-3,4-dihydro-1H-isochromen-1-one in place of (3S)-6-bromo-3-methyl-3,4-dihydro-1H-isochromen-1-one.

INTERMEDIATE 9B

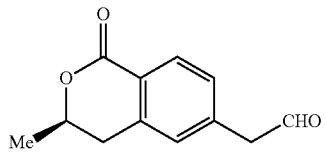

[(3R)-3-methyl-1-oxo-3,4-dihydro-1H-isochromen-6-yl]acetaldehyde

Step A: 4-bromo-N,N-diethyl-2-methylbenzamide

A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide. LC/MS: (M+H)$^+$ 270.

Step B: 4-bromo-N,N-diethyl-2-(2-oxopropyl)benzamide

A 2M solution of LDA (35.2 ml, 70.3 mmol) in THF (176 ml) cooled to −78° C. was treated with slow addition of 4-bromo-N,N-diethyl-2-methylbenzamide (19.0 g, 70.3 mmol) in dry THF (176 ml). The reaction was allowed to stir at −78° C. for 1 hour before it was quenched with N-methoxy-N-methylacetamide (22.43 ml, 211 mmol) and allowed to slowly warm to room temp. The reaction was stirred overnight and then partitioned between 1N HCl (200 mL) and EtOAc (400 mL). The aqueous layer was further extracted with EtOAc (2×150 mL). The combined organic layers were washed with brine (150 mL), dried over magnesium sulfate, filtered and concentrated. The crude material was an orange/brown oil out of which the product crystallizes. The oil was decanted off and the solid was washed with hexanes and dried using a buchner funnel to afford 4-bromo-N,N-diethyl-2-(2-oxopropyl)benzamide. LC/MS (M+H)$^+$ 312.

Step C: 4-bromo-N,N-diethyl-2-[(2R)-2-hydroxypropyl]benzamide

A flask equipped with an overhead stirrer was charge with pH=8 Phosphate Buffer (156 ml, 31.2 mmol) followed by D-glucose (1.298 g, 7.21 mmol) and then warmed to 30° C. Next, 135 mg glucose dehydrogenase and 270 mg NADP+ disodium was added to the glucose/buffer solution at once, a homogeneous solution was obtained after 1 min agitating. Next, 577 mg Codexis ketoreductase KRED P1B2 was added to the reaction vessel and stirred at 500 rpm at 30° C. until enzyme was wetted (about 40 min). Lastly, a solution of 4-bromo-N,N-diethyl-2-(2-oxopropyl)benzamide (1.5 g, 4.80 mmol) dissolved in DMSO (14.56 ml) (pre-warmed on stir plate to 30° C.) was added to the reaction over ~3 min and agitated at 30° C. (400 rpm) overnight. After 48 hours the reaction was cooled to room temperature and then 75 g of potassium carbonate was added to the reaction in portions and stirred for 15 minutes until enzyme clumped together when stirring was stopped. Next, acetonitrile (50 mL) was poured into the reaction flask and the layers were thoroughly mixed. Stirring was stopped after 15-20 minutes, the layers were allowed to separate and the upper layer decanted off. This was repeated two more times with additional 50 mL of acetonitrile. The combined organic layers were then filtered through a medium porosity funnel, concentrated and then 50 ml MTBE was added to the concentrate and stirred for 5 min and then transferred to a separatory funnel and the layers separated. The aqueous layer was extracted further another 50 ml MTBE. The combined organic extracts were dried over magnesium sulfate, filtered and concentrated. Purification via MPLC (30-70% EtOAc/Hex) afforded the title compound.

Step D: (3R)-6-bromo-3-methyl-3,4-dihydro-1H-isochromen-1-one

A solution of 4-bromo-N,N-diethyl-2-[(2R)-2-hydroxypropyl]benzamide (12.2 g, 38.8 mmol) dissolved in 4N HCl in dioxane (200 mL) was stirred at room temperature and monitored by TLC. After 3 days the reaction was partitioned between EtOAc (300 mL) and water (300 mL). The aqueous phase was further extracted with EtOAc (2×250 mL). The combined organic layers were then washed with water (200 mL), brine (200 mL), dried over magnesium sulfate, filtered and concentrated. The crude material was then purified via MPLC (15-30% EtOAc/Hexane) to afford (3R)-6-bromo-3-methyl-3,4-dihydro-1H-isochromen-1-one. LC/MS: (M+1)$^+$ 241.

Step E: (3R)-6-(1,3-dioxolan-2-ylmethyl)-3-methyl-3,4-dihydro-1H-isochromen-1-one A sealed tube was charged with aryl bromide, palladium (II) acetate (0.028 g, 0.124 mmol) and tri-t-butylphosphine-BF$_4$ complex (0.072 g, 0.249 mmol) and sealed. The tube was evacuated and refilled with nitrogen before DMF (12.44 ml) and (3R)-6-bromo-3-methyl-3,4-dihydro-1H-isochromen-1-one (0.75 g, 3.11 mmol) were added followed by bromo(1,3-dioxolan-2-ylmethyl)zinc (6.22 ml, 3.11 mmol). The tube was heated to 110° C. in the microwave for 75 minutes, after which it was cooled, diluted with EtOAc, filtered, concentrated and purified via MPLC (20-50% E/H) to afford the title compound. $^1$H NMR (500 MHz; CDCl$_3$): 8.04 (d, J=7.8 Hz, 1H), 7.32 (d, J=8.0 Hz, 1H), 7.17 (s, 1H), 5.11 (t, J=4.7 Hz, 1H), 4.68 (m, 1H), 3.96 (m, 2H), 3.88 (m, 2H), 3.03 (d, J=4.9 Hz, 2H), 2.93 (m, 2H), 1.54 (d, J=6.4 Hz, 3H); LC-MS (IE, m/z): 249 [M+1]$^+$.

Step F: [(3R)-3-methyl-1-oxo-3,4-dihydro-1H-isochromen-6-yl]acetaldehyde

A 1:1 solution of dioxane:3N HCl was added to a flask containing (3R)-6-(1,3-dioxolan-2-ylmethyl)-3-methyl-3,4-dihydro-1H-isochromen-1-one (782 mg, 3.15 mmol). The reaction was then stirred at room temp overnight. The crude reaction mixture was then partitioned between water and DCM. The organic layer was washed with saturated sodium bicarbonate solution, followed by brine. The organic layer was then dried with magnesium sulfate, filtered and concentrated to afford [(3R)-3-methyl-1-oxo-3,4-dihydro-1H-isochromen-6-yl]acetaldehyde.

INTERMEDIATE 10A

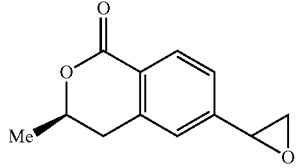

(3R)-3-methyl-6-(oxiran-2-yl)-3,4-dihydro-1H-isochromen-1-one

Step A: (3R)-6-ethenyl-3-methyl-3,4-dihydro-1H-isochromen-1-one

A solution of (3R)-6-bromo-3-methyl-3,4-dihydro-1H-isochromen-1-one (2.4 g, 9.96 mmol) and triethylamine (2.78 ml, 19.91 mmol) in EtOH (39.8 ml) was added to a microwave vial containing $Cl_2Pd(dppf)_2$-DCM (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave title compound. LC/MS (M+H)$^+$ 189;

Step B: (3R)-3-methyl-6-(oxiran-2-yl)-3,4-dihydro-1H-isochromen-1-one

A solution of 6-ethenyl-3-methyl-3,4-dihydro-1H-isochromen-1-one (1.69 g, 8.98 mmol) in DCM (60 mL) was treated with mCPBA (3.10 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give title compound. $^1$H NMR (500 MHz; CDCl$_3$): 8.10 (d, J=8.0 Hz, 1H), 7.33 (m, 1H), 7.16 (d, J=4.4 Hz, 1H), 4.71 (m, 1H), 3.92 (dt, J=1.6, 2.5 Hz, 1H), 3.22 (dt, J=1.4, 4.1 Hz, 1H), 2.96 (m, 2H), 2.80 (dd, J=2.3, 3.5 Hz, 1H), 1.55 (d, J=7.6 Hz, 3H); LC/MS (M+H)$^+$ 205.

INTERMEDIATE 10B

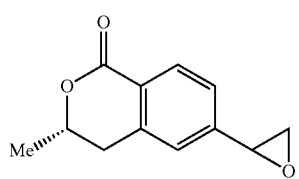

(3S)-3-methyl-6-(oxiran-2-yl)-3,4-dihydro-1H-isochromen-1-one

The title compound was prepared in an analogous fashion to that described for the synthesis of (3R)-3-methyl-6-(oxiran-2-yl)-3,4-dihydro-1H-isochromen-1-one except starting from (3S)-6-bromo-3-methyl-3,4-dihydro-1H-isochromen-1-one.

INTERMEDIATE 11

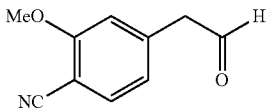

2-(Methyloxy)-4-(2-oxoethyl)benzonitrile

Step A: 2-(Methyloxy)-4-prop-2-en-1-ylbenzonitrile

To a 50 mL flask containing a stir bar were added 2-methoxy-4-bromobenzonitrile (0.30 g, 1.4 mmol), tetrakis (triphenylphosphine)palladium (82 mg, 0.071 mmol), allyltri-n-butyltin (0.88 mL, 2.8 mmol), and lithium chloride (0.120 g, 2.83 mmol). The resulting mixture was then dissolved in anhydrous toluene (16 mL); the flask was placed in an oil bath and heated at 130° C. until LC as well as TLC (hexanes/EtOAc=1/0.3) indicated that reaction had gone to completion. The flask was taken out of the oil bath and cooled to room temperature. To the flask was poured EtOAc (40 mL) and the mixture was transferred into a separatory funnel and washed with aqueous NaCl. The organic phase was dried over Na$_2$SO$_4$, filtered and concentrated to dryness. It was then dissolved in DCM and absorbed onto silica gel. The silica gel was then loaded onto a silica column for separation with the solvent systems of hexanes/EtOAc (1/0.3); this gave 2-(methyloxy)-4-prop-2-en-1-ylbenzonitrile. LC-MS (IE, m/z): 174 [M+1]$^+$.

Step B: 2-(Methyloxy)-4-(2-oxoethyl)benzonitrile

To a 25 mL flask containing a stir bar was added 2-(methyloxy)-4-prop-2-en-1-ylbenzonitrile (0.15 g, 0.87 mmol) and MeOH (8 mL). The flask was placed in a cold bath of −78° C. Ozone was bubbled through the flask for about 10 min. followed by addition of dimethyl sulfide (1.5 mL, 24 mmol). The flask was taken out of the cold bath and stirred at room temperature for 1 h. The reaction mixture was concentrated to dryness to give title compound. LC-MS (IE, m/z): 176 [M+1]$^+$.

INTERMEDIATE 12

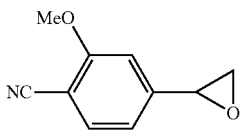

2-(methyloxy)-4-oxiran-2-ylbenzonitrile

Step A: 4-Formyl-2-methoxyphenyl trifluoromethanesulfonate

To a solution of vanillin (20.0 g, 131 mmol) in DMF (200 mL) at room temperature was added potassium carbonate (36 g, 263 mmol) and 4-nitrophenyl trifluoromethanesulfonate (54.0 g, 197 mmol) and the reaction mixture was stirred for 8 h. EtOAc (600 mL) was added to the reaction mixture and the organic layer was washed three times with water, dried, filtered, and concentrated. The crude compound was then purified by flash chromatography (ethylacetate/hexanes 1:9→3:7) to provide 4-formyl-2-methoxyphenyl trifluoromethanesulfonate._LC/MS (IE, m/z) 284.98 [M+1]$^+$;

Step B: 4-Formyl-2-methoxybenzonitrile

A mixture of 4-formyl-2-methoxyphenyl trifluoromethanesulfonate (37.0 g, 130 mmol), zinc cyanide (61.0 g, 521 mmol) and tetrakis triphenylphosphine palladium (0) (22.6 g, 19.5 mmol) in DMF (300 mL) were stirred at 110° C. for 8 h. EtOAc was added to the reaction mixture and the organic layer was washed two times with water, dried, filtered and concentrated. The crude product was then purified by column chromatography (silica gel, ethylacetate/hexanes 3:7) which afforded 4-formyl-2-methoxybenzonitrile._LC/MS (IE, m/z) 162.07 [M+1]$^+$.

Step C: 2-Methoxy-4-(oxiran-2-yl)benzonitrile

To a cool solution of NaH (0.16 g, 3.9 mmol) in THF (40 ml) was added dropwise a solution of trimethylsulfonium iodide (0.91 g, 4.5 mmol) in DMSO (20 ml). The resulting mixture was stirred at 0° C. under $N_2$ for 20 min. The solution of 4-formyl-2-methoxybenzonitrile (0.60 g, 3.7 mmol) in THF (20 ml) was added. The resulting reaction mixture was stirred at 0° C. under $N_2$ for 1 hr, and then it was warmed gradually to room temperature and stirred at that temperature for 12 hr. The starting material was consumed as indicated by TLC (25% ethyl acetate/hexanes). The reaction mixture was cooled to 0° C. and quenched by drop-wise addition of water. The mixture was extracted with ethyl acetate (2×70 mL). The combined organic layers were washed with water, brine, then dried (MgSO$_4$) and filtered. The filtrate was concentrated in vacuo. The residue was purified via column chromatography (silica gel, 10-30% EtOAc-hexanes) to afford 2-methoxy-4-(oxiran-2-yl)benzonitrile. $^1$H NMR (CDCl$_3$, 500 MHz) δ 7.57 (d, J=8 Hz, 1H), 6.99 (dd, J=1.1 Hz, J=1.2 Hz, 1H), 6.89 (s, 1H), 3.97 (s, 3H), 3.94-3.92 (m, 1H), 3.22 (dd, J=5.2, Hz, J=4.1 Hz, 1H), 2.77 (J=2.5 Hz, 1H); LC/MS (IE, m/z) 176.33 [M+1]

INTERMEDIATE 13

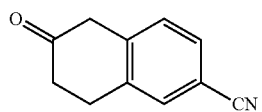

6-Oxo-5,6,7,8-tetrahydronaphthalene-2-carbonitrile

The 5-bromo-2 tetralone (2.0 g, 8.9 mmol), tetrakis(triphenylphosphine)palladium (0.62 g, 0.53 mmol) and zinc cyanide (0.73 g, 6.2 mmol) were added to 4 ml DMF in a 20 ml microwave tube. The mixture was degassed and microwaved at 80° C. for 30 mins. TLC showed no starting material left and the mixture was diluted with ethyl acetate and washed with ammonium hydroxide (2M, ×4 ml). The organic layer was separated and dried over Na$_2$SO$_4$ then filtered. The solvent was evaporated under reduced pressure. The residue was chromatographed through 40 gm Isco Redi-sep column and eluted with 0-30% ethyl acetate-hexane to yield 6-oxo-5,6,7,8-tetrahydronaphthalene-2-carbonitrile.

$^1$H-NMR (500 MHz, CDCl$_3$) δ ppm 7.57 (s, 1H), 7.54 (d, J=8 .Hz, 1H), 7.26 (d, J=8 .Hz, 1H), 3.67 (s, 2H), 3.14 (t, J=6.7 .Hz, 2H), 2.63 (t, J=6.7 .Hz, 2H).

INTERMEDIATE 14

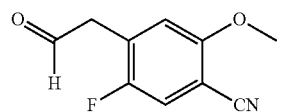

5-Fluoro-2-methoxy-4-(2-oxoethyl)benzonitrile

Step A: di-tert-Butyl (4-cyano-2-fluoro-5-methoxyphenyl)propanedioate

A suspension of NaH (60% in mineral oil, 0.33 g, 8.3 mmol) in dry DMF (20 mL) was stirred and cooled to 0° C., and di-tert-butyl malonate (1.5 g, 7.1 mmol) was added. The mixture was allowed to warm to RT before addition of 4,5-difluoro-2-methoxybenzonitrile (1.0 g, 5.9 mmol). The mixture was heated at 80° C. for 4 h with stirring, then the reaction mixture was cooled to RT and poured into a mixture of ice-water (100 mL) and AcOEt (100 mL). The layers were separated, and the organic layer was washed successively with water, and brine, then dried over Na$_2$SO$_4$ and concentrated. The residue was purified by flash chromatography (silica gel, EtOAc/hexanes, 0→10%) to give the title compound._LCMS: [(M+1)-t-Bu,CO2-t-Bu]$^+$=210.1;

Step B: (4-cyano-2-fluoro-5-methoxyphenyl) acetic acid

TFA (5 mL) was added to a solution of di-tert-butyl (4-cyano-5-fluoro-2-methoxyphenyl) propanedioate (1.3 g, 28.3 mmol) in of dichloromethane (5 mL) at room temperature. The reaction mixture was stirred over night, then concentrated under reduced pressure, and the residue was treated with Et$_2$O (10 mL) to induce crystallization. The crystals were collected by filtration to give title compound. LC/MS: [(M+1)]$^+$=210.1.

Step C: methyl (4-cyano-2-fluoro-5-methoxyphenyl)acetate

Can be prepared by esterification of (4-cyano-2-fluoro-5-methoxyphenyl) acetic acid by, for example, treatment with anhydrous methanolic HCl solution.

Step D: 5-fluoro-4-(2-hydroxyethyl)-2-methoxybenzonitrile

To a solution of methyl (4-cyano-2-fluoro-5-methoxyphenyl)acetate (212 mg, 0.95 mmol) in tetrahydrofuran (4 mL) at 0° C. was added lithium borohydride (2.0 M solution in tetrahydrofuran, 0.62 mL). The mixture warmed slowly to room temperature and was quenched with saturated sodium bicarbonate and diluted with ethyl acetate. The layers were separated and the aqueous extracted with ethyl acetate (2×). The combined organics were washed with water and brine, then dried (Na$_2$SO$_4$), filtered and concentrated. The residue was purified by column chromatography (MPLC, 5-60%

Ethyl Acetate:Hexanes) to provide 5-fluoro-4-(2-hydroxyethyl)-2-methoxybenzonitrile.

Step E:
5-Fluoro-2-methoxy-4-(2-oxoethyl)benzonitrile

To a solution of 5-fluoro-4-(2-hydroxyethyl)-2-methoxybenzonitrile (175 mg, 0.90 mmol) in dichloromethane (4 mL) was added Dess-Martin periodinane (530 mg, 1.3 mmol) at RT. The mixture stirred at room temperature for 2 h, then was diluted with saturated sodium bicarbonate and saturated sodium thiosulfate and stirred 30 min. The mixture was extracted with dichloromethane (3×) and the combined organics dried (MgSO$_4$), filtered and concentrated to provide title compound which was used without further purification. LC-MS (IE, m/z): 194.2 [M+1]$^+$.

INTERMEDIATE 15

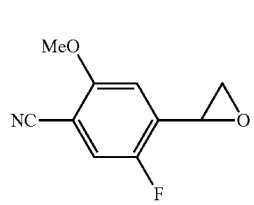

5-Fluoro-2-methoxy-4-oxiran-2-ylbenzonitrile

To a solution of 5-fluoro-4-(2-hydroxyethyl)-2-methoxybenzonitrile (0.68 g, 3.5 mmol) and Et$_3$N (0.82 mL, 5.9 mmol) in dichloromethane (5 mL) was added methanesulfonyl chloride (0.33 mL, 4.2 mmol) at 0° C. After 15 min. the reaction mixture was poured into saturated ammonium chloride and extracted with dichloromethane. The combined organics were washed with 1 N HCl, saturated sodium bicarbonate solution, and brine, then dried (MgSO$_4$) and concentrated in vacuo. The residue was re-dissolved in dichloromethane (5 mL), treated with DBU (0.79 mL, 5.2 mmol) and stirred for 2 h. TLC monitoring showed conversion to the olefin. The reaction mixture was diluted with water and extracted with dichloromethane. The combined organics were washed with 1 N HCl, saturated sodium bicarbonate solution, and brine, then dried (MgSO$_4$) and concentrated in vacuo. The resulting olefin was dissolved in dichloromethane (5 mL) and treated with meta-chloro perbenzoic acid (0.72 g, 4.2 mmol) at 0° C. After 3 h, the mixture was diluted with saturated sodium bicarbonate solution and extracted with dichloromethane (twice). The combined organic extracts were washed with brine, dried (MgSO$_4$), filtered and concentrated in vacuo. The crude epoxide was purified by silica gel column chromatography (5→80% EtOAc:hexane) to provide 5-fluoro-2-methoxy-4-oxiran-2-ylbenzonitrile. $^1$H NMR (500 MHz, CD$_3$OD) δ 7.32 (d, J=5.3 Hz, 1H), 6.82 (d, J=5.4 Hz, 1H), 4.19 (m, 1H), 3.96 (s, 3H), 3.27 (m, 1H), 2.76 (m, 1H);
LC/MS: [(M+1)]$^+$=194.1.

INTERMEDIATE 16

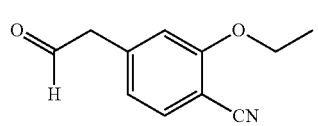

2-Ethoxy-4-(2-oxoethyl)benzonitrile

Step A: 2-(Ethoxy)-4-(2-hydroxyethyl)benzonitrile

A suspension of (4-cyano-3-ethoxyphenyl)acetic acid (100 mg, 0.49 mmol) in THF (5 mL) was treated with borane dimethyl sulfide complex (2M, 0.49 mL, 0.98 mmol) and the reaction was stirred 1 hour at room temperature. The reaction was not complete, so an additional aliquot of borane dimethyl sulfide complex (2M, 0.49 mL, 0.98 mmol) was added. After stirring for another 1 h at RT, the reaction was quenched with methanol and the mixture was partitioned with ethyl acetate and 2N HCl/water. The aqueous was extracted again with ethyl acetate and the organic layers were washed with brine, dried over sodium sulfate and evaporated. The residue was purified on a silica gel column (gradient 20-50% ethyl acetate in hexanes) to afford the title alcohol.

Step B: 2-(Ethoxy)4-(2-oxoethyl)benzonitrile

A solution of 2-(ethoxy)-4-(2-hydroxyethyl)benzonitrile (56 mg, 0.29 mmol) in DCM (5 mL) was treated with Dess-Martin periodinane (250 mg, 0.59 mmol) and was stirred at room temperature for 2.5 hours. The reaction was quenched by partitioning with DCM and water containing sodium bicarbonate and sodium thiosulfate (3×). The organic layer was then washed with brine, dried over sodium sulfate and evaporated to give the title aldehyde which was used directly.

INTERMEDIATE 17

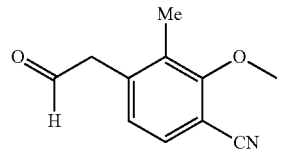

(2-Methoxy-3-methyl-4-(2-oxoethyl)benzonitrile

Step A: t-Butyl methyl (4-cyano-3-fluoro-2-methylphenyl)malonate tert-Butyl methyl malonate (0.71 g, 4.1 mmol) in anhydrous DMF (20 mL) under nitrogen was cooled in an ice bath. Sodium hydride (60% in mineral oil, 176 mg, 7.4 mmol) was added portionwise over 5 minutes. The reaction was allowed to warm to room temperature for 30 minutes at which time all was in solution and hydrogen gas had ceased. To the solution was then added 2,4-difluoro-3-methylbenzonitrile (0.500 g, 3.3 mmol) as a solid in one portion. The reaction was heated in a 95° C. oil bath for 5 hours and then stirred at room temperature for 16 hours. The reaction was quenched by addition of 2N HCl in water. The mixture was portioned with ether (2×), and the organic layers were washed with brine, dried over sodium sulfate and evaporated in vacuo. TLC (10% ethyl acetate/hexanes) indicated a small amount of di-fluoro starting material, major desired product plus some minor isomer (slightly higher Rf) and excess malonate. The crude residue was purified by FC (5-7% to elute excess malonate, starting material and minor isomer, then 10-15% ethyl acetate/hexanes to elute the product) to afford title compound.

Step B: Methyl (4-cyano-3-fluoro-2-methylphenyl)acetate

To a solution of tert-Butyl methyl (4-cyano-3-fluoro-2-methylphenyl)malonate (0.75 g, 2.4 mmol) in DCM (10 mL) was added TFA (10 mL) at room temperature and the mixture was aged for 3 hours. LC-MS and TLC (15% ethyl acetate/hexanes) indicated the lack of starting diester, but still some mono-acid/mono-ester intermediate. The volatiles were removed in vacuo and the residue was taken up in dioxane with a few drops of acetic acid and heated to reflux for 1 hour. The volatiles were again removed in vacuo and the residue was purified by flash chromatography (5-15% ethyl acetate/hexanes) to give title ester product.

Step C: Methyl (4-cyano-3-methoxy-2-methylphenyl)acetate

A solution of methyl (4-cyano-3-fluoro-2-methylphenyl) acetate (0.38 g, 1.8 mmol) was taken up in methanol (6 mL) and potassium carbonate (0.51 g, 3.7 mmol) was added. The reaction was heated at 135° C. for 2.5 hours. The reaction mixture was concentrated, the residue was diluted with water and extracted 2× with ethyl acetate, and the organic layers were washed with brine, dried over sodium sulfate and evaporated in vacuo. Flash chromatography (5-10% ethyl acetate/hexanes) still gave a mixture so repeated chromatography (25-100% DCM in hexanes) gave title ester.

Step D: 4-(2-Hydroxyethyl)-2-methoxy-3-methylbenzonitrile

A suspension of methyl (4-cyano-3-methoxy-2-methylphenyl)acetate (175 mg, 0.80 mmol) in THF (5 mL) was treated with lithium borohydride solution in THF (2M, 0.79 mL, 1.6 mmol) and the reaction was stirred overnight at room temperature. The reaction was quenched with 2N HCl and the mixture was partitioned with ethyl acetate and water. The aqueous layer was extracted again with ethyl acetate and the organic layers were washed with brine, dried over sodium sulfate and evaporated. The residue was purified on a silica gel column (gradient 10-15% ethyl acetate in hexanes to elute some remaining starting material, then 15-25% to elute the product) to afford the title alcohol.

Step E: 2-Methoxy-3-methyl-4-(2-oxoethyl)benzonitrile

A solution of 2-methoxy-3-methyl-4-(2-hydroxyethyl) benzonitrile (60 mg, 0.31 mmol) in DCM (5 mL) was treated with Dess-Martin periodinane (266 mg, 0.63 mmol) and was stirred at room temperature for 2 hours. MS/LC showed an aldehyde peak by UV (no M+1 detected in the MS) and no alcohol. The reaction was quenched by partitioning with DCM and water containing sodium bicarbonate and sodium thiosulfate. The organic layer was then washed with brine, dried over sodium sulfate and evaporated to give crude title aldehyde which was used directly. LC-MS of the crude mixture indicated a mixture of aldehyde and a trace of periodinane by-product.

INTERMEDIATE 18

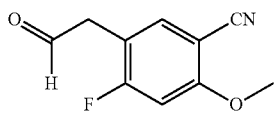

4-Fluoro-2-methoxy-5-(2-oxoethyl)benzonitrile

Step A: 4-Fluoro-5-iodo-2-methoxybenzonitrile

To 4-fluoro-2-methoxybenzonitrile (3.00 g, 20 mmol) and N-iodosuccinimide (4.7 g, 21 mmol) under nitrogen was added TFA (35 mL) and the reaction was stirred at room temperature for 20 hours. The volatiles were removed in vacuo and the residue was taken up in 1:1 ethyl acetate: ether and was washed with aqueous sodium bicarbonate and then brine containing enough sodium sulfite to remove the iodine color. The aqueous layers were back extracted with more 1:1 ethyl acetate:ether and the combined organic layers were dried over sodium sulfate and evaporated. The residue was triturated with ether/hexanes to afford title product.

Step B: 4-Fluoro-2-methoxy-5-(prop-2-en-1-yl)benzonitrile

To a mixture of 4-fluoro-5-iodo-2-methoxybenzonitrile (2.5 g, 9.0 mmol), Pd(Ph$_3$P)$_4$ (1.0 g, 0.90 mmol) and lithium chloride (0.96 g, 23 mmol) under nitrogen was added anhydrous toluene (50 mL) and the mixture was flushed (3×) with nitrogen. Allyltributyltin (4.15 mL, 14 mmol) was added and the mixture was flushed again with nitrogen. The reaction was heated under nitrogen at 115° C. for 2.5 hours and then let cool to room temperature. TLC (10% ethyl acetate/Hexanes) showed several spots with a strongly charring product spot right above the starting material. The reaction was diluted with hexanes and filtered to remove insoluble material. The mother liquor was concentrated and the residue was purified on a Biotage 65+M column with a gradient elution from 0 to 40% ethyl acetate in hexanes to afford the title product which had some residual tributylstanane by-product contaminant by NMR.

Step C: 4-Fluoro-5-(2-hydroxyethyl)-2-methoxybenzonitrile

A solution of 4-fluoro-2-methoxy-5-(prop-2-en-1-yl)benzonitrile (1.2 g, 6.0 mmol) in methanol (50 mL) was cooled in a dry ice acetone bath and treated with ozone. Since the starting material was contaminated with some tributylstanane residue from the previous reaction, the reaction turned brown at first. The mixture was flushed with nitrogen and quenched with dimethylsulfide (4 mL). The solution was allow to warm to about 0° C. which resulted in a clear yellow solution and then sodium borohydride (0.27 g, 7.2 mmol) was added under nitrogen and the reaction was stirred for 30 minutes at room temperature. TLC of an aliquot in ether/water (30% ethyl acetate in hexanes) indicated a product band without evidence of starting material. After a total of 1 hour, the reaction was quenched with 18% aqueous citric acid and concentrated in vacuo to remove the methanol. The residue was partitioned between ethyl acetate and 18% citric acid, washed with brine, dried over sodium sulfate and evaporated. Purification of the residue with a Biotage 40+M column (10 to 60% ethyl acetate in hexanes) gave the title alcohol.

Step D: 4-Fluoro-2-methoxy-5-(2-oxoethyl)benzonitrile

A solution of 4-fluoro-5-(2-hydroxyethyl)-2-methoxybenzonitrile (72 mg, 0.37 mmol) in DCM (5 mL) was treated with Dess-Martin periodinane (313 mg, 0.74 mmol) and was stirred at room temperature for 3 hours. The reaction was quenched by partitioning with DCM and water containing sodium bicarbonate and sodium thiosulfate for 30 minutes. The organic layer was then washed with brine, dried over sodium sulfate and evaporated to give crude title aldehyde as an oil which was used directly in subsequent reductive amination reactions. NMR of the crude mixture indicated an apparent mixture of aldehyde and acid (2:1 ratio) and some periodinane by-product. $^1$H-NMR (500 MHz, CDCl$_3$) δ ppm 3.726 and 3.741 (2 s, 2H, 2:1 ratio), 3.933 (s, 3H), 6.745 (d, J=11.0 Hz, 1H), 7.419 and 7.490 (2 d, J=8.0 Hz, 1H, 2:1 ratio).

INTERMEDIATE 19

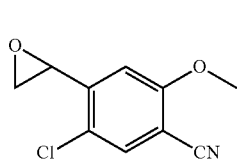

(2-Chloro-4-cyano-5-methoxyphenyl)ethylene oxide

Step A: Di-t-Butyl 2-(2-chloro-4-cyano-5-fluorophenyl)malonate

To sodium hydride (60% in mineral oil, 3.75 g, 94 mmol) under nitrogen was added dry DMF (150 mL) and the suspension was cooled in an ice bath. Di-t-butyl malonate (8.1 g, 37.5 mmol) was added dropwise over 15 minutes via syringe with hydrogen evolution. The suspension was stirred for 30 minutes after which time 5-chloro-2,4-difluorobenzonitrile (5.0 g, 28.8 mmol) in DMF (10 mL) was added dropwise over 15 minutes and the reaction was heated to 80° C. for 12 hours when TLC (15% ethyl acetate/hexanes) indicated mostly product. The reaction was diluted with ether and quenched into water containing aq. ammonium chloride. The mixture was extracted twice with ethyl acetate and the organic layers were washed with brine, dried over sodium sulfate and concentrated in vacuo. The residue was purified on silica gel (2-10% ethyl acetate/hexanes) to give the title product. NMR indicated about a 6:1 mixture of product and the isomeric di-t-butyl, 2-(4-chloro-2-cyano-5-fluorophenyl)malonate.

Step B: Methyl (2-chloro-4-cyano-5-fluorophenyl)acetate

A solution of di-t-butyl 2-(2-chloro-4-cyano-5-fluorophenyl)malonate (9.10 g, 24.6 mmol) in 1:2 TFA:dichloromethane (25:50 mL) was stirred at RT for 3 hours and then concentrated in vacuo to give a solid (5.05 g) after twice evaporating toluene. An aliquot of 4 g of solid was taken up in 1:1 methanol:dichloromethane (50 mL) and 2M trimethylsilyldiazomethane in ether was added until the yellow color persisted. Excess diazomethane was quenched with acetic acid and the mixture was concentrated. The residue was purified by flash chromatography (5-15% ethyl acetate/hexanes containing 5% DCM for solubility) to give separation from the higher R$_f$ 4-chloro-2-cyano-5-fluorophenyl isomer and still impure title product isomer. Flash chromatography was repeated (50-100% DCM/hexanes) to afford title product.

Step C: Methyl (2-chloro-4-cyano-5-methoxyphenyl)acetate

A solution of methyl (2-chloro-4-cyano-5-fluorophenyl)acetate (1.40 g, 6.15 mmol) in methanol (30 mL) was divided into two 20 mL microwave vials. Potassium carbonate (2×850 mg) was added to each vial. Each was heated in a microwave at 130° C. for 60 minutes at which time HPLC/MS indicated no starting material was left and the product was all hydrolyzed to the acid. Most of the methanol was removed in vacuo and the residue was diluted with water, acidified with 2M HCl and the mixture was extracted twice with ethyl acetate. The organic layers were washed with brine, dried over sodium sulfate and concentrated in vacuo. The crude product was taken up in 1:1 methanol: dichloromethane (50 mL) and 2M trimethylsilyldiazomethane in ether was added until the yellow color persisted to re-esterify the acid. The excess diazomethane was quenched with acetic acid and the mixture was concentrated. Flash chromatography (40% DCM/hexanes to 100% DCM) gave the methyl (2-chloro-4-cyano-5-methoxyphenyl)acetate.

Step D: 2-(2-chloro-4-cyano-5-methoxyphenyl)ethanol

To a solution of methyl (2-chloro-4-cyano-5-methoxyphenyl)acetate (200 mg, 0.835 mmol) in THF (5 mL) was added 2M lithium borohydride (0.835 mL, 1.67 mmol) and the reaction was stirred at RT for 16 hours. The reaction was diluted with ether and quenched into water containing 2N HCl. The mixture was extracted twice with ethyl acetate and the organic layers were washed with brine, dried over sodium sulfate and concentrated in vacuo. The product mixture was separated by MPLC (40+S; 20-60% ethyl acetate/hexanes) to afford the title product.

Step E: 2-(2-Chloro-4-cyano-5-methoxyphenyl)ethyl methanesulfonate

A solution of 2-(2-chloro-4-cyano-5-methoxyphenyl) ethanol (205 mg, 0.969 mmol), DIPEA (0.846 mL, 4.84 mmol) and pyridine (0.0780 mL, 0.969 mmol) in DCM (3 mL) was treated dropwise with mesyl chloride (0.110 mL, 1.42 mmol). The reaction was stirred for 2 hours and was then diluted with DCM and washed twice with aq. citric acid, then washed with brine, and dried over sodium sulfate. Purification of the residue by flash chromatography (20-50% ethyl acetate/hexanes) afforded the title intermediate.

Step F: (2-Chloro-4-cyano-5-methoxyphenyl)ethylene

A solution of 2-(2-chloro-4-cyano-5-methoxyphenyl) ethyl methanesulfonate (274 mg, 0.945 mmol) in DCM (4 mL) was treated with DBU (0.712 mL, 4.73 mmol) and stirred for 3 hours at 50° C., then at RT for 12 hours. TLC (50% ethyl acetate/hexanes) showed complete conversion to a faster intense UV band for the product. The reaction was then diluted with DCM and aq. citric acid and the mixture was extracted twice with DCM. The organic layers were washed with brine, dried over sodium sulfate and concentrated in vacuo. Purification of the residue by flash chromatography (10-20% ethyl acetate/hexanes) afforded the title intermediate.

Step G: (2-Chloro-4-cyano-5-methoxyphenyl)ethylene oxide

A solution of (2-chloro-4-cyano-5-methoxyphenyl)ethylene (130 mg, 0.671 mmol) in DCM (6 mL) was treated with 85% mCPBA (226 mg, 1.10 mmol) and stirred for 5 hours at RT when another portion of mCPBA (115 mg) was added. The reaction stirred at room temperature for another 16 hours and was then diluted with DCM and stirred with sat'd sodium bicarbonate containing some sodium bisulfite. The mixture was then extracted twice with DCM and the organic layers were washed with another portion of sodium bicarbonate and brine, dried over sodium sulfate and concentrated in vacuo to afford the crude title epoxide. $^1$H-NMR (500 MHz, CDCl$_3$) δ ppm 2.67 (dd, J=2.6, 5.8 Hz, 1H), 3.28 (dd, J=4.1, 5.5 Hz, 1H), 3.95 (s, 3H), 4.22 (dd, J=2.5, 3.9 Hz, 1H), 6.91 (s, 1H), 7.564 (s, 1H).

INTERMEDIATE 20

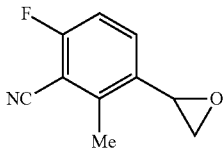

6-fluoro-2-methyl-3-oxiran-2-ylbenzonitrile

Step A: 3-bromo-6-fluoro-2-methylbenzonitrile

To a cooled (0° C.) solution of 2-fluoro-6-methylbenzonitrile (5.0 g, 37 mmol) in 100 mL of concentrated H$_2$SO$_4$ was added NBS (6.93 g, 38.9 mmol). Then the mixture was stirred at 0° C. for 3 hrs and poured into ice-water (1 L). The solution was extracted three times with EtOAc (200 mL) and the combined organic layers were washed with water and brine, dried over anhydrous sodium sulfate, filtered and concentrated. The residue was purified by silica gel flash chromatography to give title compound.

Step B: 3-ethenyl-6-fluoro-2-methylbenzonitrile

A mixture of 3-bromo-6-fluoro-2-methylbenzonitrile (8.8 g, 41 mmol), tributyl(vinyl)tin (14.3 g, 45.2 mmol), LiCl (5.20 g, 123 mmol) and Pd(PPh$_3$)$_4$ (2.3 g, 2.0 mmol) in toluene (200 mL) was heated at 100-110° C. under N$_2$ overnight. The mixture was concentrated and the residue was purified by column chromatography to obtain 3-ethenyl-6-fluoro-2-methylbenzonitrile.

Step C: 6-fluoro-2-methyl-3-oxiran-2-ylbenzonitrile

To a cooled (0° C.) solution of 3-ethenyl-6-fluoro-2-methylbenzonitrile (6.05 g, 37.6 mmol) in 200 mL of DCM was added mCPBA (15.30 g, 85% purity, 75.16 mmol). Then the mixture was stirred at r.t. for 12 hrs and diluted with DCM (300 mL), washed with saturated Na$_2$SO$_3$ (4×300 mL) and brine, dried over anhydrous sodium sulfate, filtered and concentrated. The residue was purified by column chromatography to obtain title compound. $^1$H-NMR (400 MHz, CDCl$_3$) δ ppm 7.41~7.44 (m, 1H), 7.02 (t, J=8.6 Hz, 1H), 3.95 (t, J=3.1 Hz, 1H), 3.16~3.19 (m, 1H, 2.60~2.62 (m, 4H).

INTERMEDIATE 21

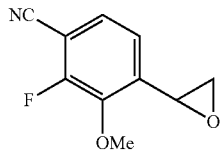

2-fluoro-3-methoxy-4-(oxiran-2-yl)benzonitrile

Step A: 2-fluoro-6-nitrophenol

Concentrated HNO$_3$ (95%, 44 g, 0.62 mol) was added dropwise at 0-5° C. to the solution of 2-fluorophenol (64.6 g, 0.58 mol) in 1 L of DCM. The mixture was stirred at 0° C. for 1 hour before filtration. The filtrate was washed with water and brine, dried over anhydrous Na$_2$SO$_4$ and concentrated. The residue was purified by column chromatography (DCM:PE=1:2) to afford 2-fluoro-6-nitrophenol.

Step B: 1-fluoro-2-methoxy-3-nitrobenzene

MeI (27.1 g, 191 mmol) was added dropwise to the suspension of 2-fluoro-6-nitrophenol (25.0 g, 159 mmol) and K$_2$CO$_3$ (44.0 g, 318 mmol) in 200 mL of DMF. The mixture was stirred overnight at 25° C. then warmed to 60° C. and stirred for 3 hours. The mixture was diluted with 1 L of EtOAc and washed with water (3×100 mL) and brine (100 mL), dried over anhydrous Na$_2$SO$_4$ and concentrated to afford the title compound.

Step C: 3-fluoro-2-methoxyaniline

A mixture of 1-fluoro-2-methoxy-3-nitrobenzene (25.0 g, 146 mmol) and Pd/C (10%, 7.5 g) in 500 mL of MeOH was stirred at room temperature under 55 psi of H$_2$ for 4 hours before filtration. The filtrate was concentrated to give the title compound.

Step D: 1-bromo-3-fluoro-2-methoxybenzene

NaNO$_2$ (12.0 g, 173 mmol, in 40 mL of water) solution was added dropwise to the mixture of 3-fluoro-2-methoxyaniline (20.0 g, 158 mmol) in 200 mL of hydrobromic acid (47%) and 100 mL of water at −5~0° C. and stirred for 1 hour. This solution was then added slowly to the suspension of CuBr (45.2 g, 315 mmol) in 50 mL of hydrobromic acid (47%) at 0° C. The resulting mixture was stirred at 0° C. for 1 hour then warmed to 50° C. and stirred for 1 hour. The reaction mixture was poured into ice water and extracted with ether (2×500 mL). The combined organic layer was washed with brine, dried over anhydrous Na$_2$SO$_4$ and concentrated to give 1-bromo-3-fluoro-2-methoxybenzene.

Step E: 4-bromo-2-fluoro-3-methoxybenzoic acid n-BuLi (17.0 mL, 42.5 mmol) was added dropwise to the solution of NH(i-Pr)$_2$ (4.50 g, 44.5 mmol) in 70 mL of THF at −70° C. The mixture was stirred at 0° C. for 15 minutes and then cooled to −70° C. again. The solution of 1-bromo-3-fluoro-2-methoxybenzene (8.30 g, 40.5 mmol, in 30 mL of THF) was added dropwise. The resulting mixture was stirred at −70° C. for 1 hour then poured into fresh dry ice and stirred overnight. The mixture was diluted with 1 L of ether and washed with water twice. The combined water layer was washed with ether then acidified to pH=2 with hydrochloric acid and extracted with EtOAc twice. The combined EtOAc layer was washed with brine, dried over anhydrous Na$_2$SO$_4$ and concentrated to give 4-bromo-2-fluoro-3-methoxybenzoic acid.

Step F: 4-bromo-2-fluoro-3-methoxybenzonitrile

Oxalyl chloride (20 mL) was added dropwise at 0° C. to a suspension of 4-bromo-2-fluoro-3-methoxybenzoic acid (8.30 g, 33.3 mmol) in 100 mL of DCM with 0.5 mL of DMF. The mixture was stirred at 25° C. for 2 hours and the clear solution was concentrated to dryness under reduced pressure. The residue dissolved in 60 mL of anhydrous acetonitrile was added to 600 mL of aqueous NH$_3$.H$_2$O at 0° C. and stirred for 2 hours then extracted with EtOAc twice. The combined EtOAc layer was washed with water and brine, dried over anhydrous Na$_2$SO$_4$ and concentrated. The residue (6.9 g) was dissolved in 60 mL of DMF and cooled to 0° C. with ice/water bath. Cyanuric chloride (7.70 g, 41.7 mmol) was added and stirred for 2 hours at 0° C. before poured to ice/water. The solid was collected by filtration and was washed with water, dissolved in DCM, dried over anhydrous Na$_2$SO$_4$ and concentrated to afford 4-bromo-2-fluoro-3-methoxybenzonitrile.

Step G: 2-fluoro-3-methoxy-4-vinylbenzonitrile

A mixture of 4-bromo-2-fluoro-3-methoxybenzonitrile (6.0 g, 26 mmol), potassium vinyltrifluoroborate (4.20 g, 31.3 mmol) and Pd(dppf)Cl$_2$ (0.8 g) in 60 mL of EtOH and 60 mL of TEA was refluxed under Ar for 4 hours. The resulting mixture was concentrated and the residue was purified by column chromatography (PE:EtOAc=20:1) to afford 2-fluoro-3-methoxy-4-vinylbenzonitrile.

Step H: 2-fluoro-3-methoxy-4-(oxiran-2-yl)benzonitrile mCPBA (85%, 9.9 g, 48.9 mmol) was added to the solution of 2-fluoro-3-methoxy-4-vinylbenzonitrile (3.4 g, 19.2 mmol) in 160 mL of DCM at 0° C. The mixture was stirred at room temperature for 60 hours before being diluted with 300 mL of DCM and cooled to 0° C. The mixture was washed subsequently with saturated NaHCO$_3$ (50 mL), aqueous Na$_2$SO$_3$ (2×50 mL), 5% NaOH (50 mL) and brine. The organic layer was concentrated, and the residue was purified by column chromatography (PE:EtOAc=5:1) to afford 2-fluoro-3-methoxy-4-(oxiran-2-yl)benzonitrile: $^1$H NMR (400 MHz, CDCl$_3$) δ 7.24 (d, J=7.6 Hz, 1H), 6.98 (d, J=7.6 Hz, 1H), 4.14-4.18 (m, 1H), 4.03 (s, 3H), 3.17-3.19 (m, 1H), 2.63-2.66 (m, 1H); MS m/z 194 (M+1)$^+$.

INTERMEDIATE 22

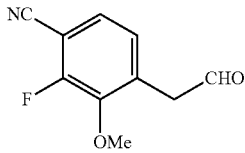

2-fluoro-3-methoxy-4-(2-oxoethyl)benzonitrile

Step A: 2-fluoro-4-(2-hydroxyethyl)-3-methoxybenzonitrile

To 2-fluoro-3-methoxy-4-(oxiran-2-yl)benzonitrile (100 mg, 0.518 mmol) in ethanol (2.6 mL) was added Pd/C (19.8 mg, 0.186 mmol) and ammonium formate (98.0 mg, 1.55 mmol). The reaction mixture was vigorously stirred for 3 h, and was filtered through CELITE® to give the crude product, which was purified by column chromatography (0-100% EtOAc/hexanes) to give target compound.

Step B: 2-fluoro-3-methoxy-4-(2-oxoethyl)benzonitrile

To 2-fluoro-4-(2-hydroxyethyl)-3-methoxybenzonitrile (80.0 mg, 0.437 mmol) in DCM (2.0 mL) was added Dess-Martin periodinane (243 mg, 0.574 mmol). The reaction mixture was vigorously stirred for 1.5 h, and was diluted with saturated aqueous NaHCO$_3$ (2 mL) and Na$_2$S$_2$O$_3$ (2 mL), and stirred for 20 min. The aqueous layer was extracted with DCM (2×5 mL), and the organic layer was washed with brine, dried, and concentrated to give title compound. $^1$H NMR (500 MHz, CDCl$_3$) δ 9.75 (s, 1H), 7.28 (dd, J=8.0, 5.7 Hz, 1H), 7.04 (d, J=8.0 Hz, 1H), 3.98 (s, 3H), 3.82 (s, 2H).

INTERMEDIATE 23

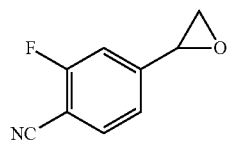

2-fluoro-4-oxiran-2-ylbenzonitrile

Step A: (4-cyano-3-fluorophenyl)acetic acid

A solution of dry diisopropylamine (16.5 g, 163 mmol) in dry THF (150 mL) under nitrogen was cooled with a −78° C. dry ice/acetone bath, and n-butyl lithium (2.50 M in hexane, 65.2 mL) was added slowly. The resulting solution was warmed to ambient temperature for 10 min and then cooled to −78° C. again. HMPA (30.0 mL, 168 mmol) was added, followed by a solution of 2-fluoro-4-methylbenzonitrile (20.0 g, 148 mmol) in 50 mL of dry THF. After stirring at −78° C. for 2 hours, CO$_2$ was bubbled through the solution for 20 min, and then the mixture was warmed slowly to 0° C. Then 1 N HCl was added until pH=2 and the mixture was extracted with EtOAc. The organic layers were washed with brine and dried over anhydrous sodium sulphate and concentrated to afford title compound.

Step B: 2-fluoro-4-(2-hydroxyethyl)benzonitrile

To a solution of (4-cyano-3-fluorophenyl)acetic acid (25.6 g, 143 mmol) in 150 mL of dry THF was cooled by ice/water, and then BH3/Me2S (10 M, 15.7 mL, 157 mmol) was added slowly. The reaction was warmed to ambient temperature and stirred overnight. The mixture was quenched with MeOH and concentrated to dryness. The residue was partitioned between water and EtOAc. The organic layers were washed with brine, dried over anhydrous sodium sulfate and concentrated to afford 2-fluoro-4-(2-hydroxyethyl)benzonitrile.

Step C: 2-(4-cyano-3-fluorophenyl)ethyl methanesulfonate

A solution of 2-fluoro-4-(2-hydroxyethyl)benzonitrile (22.5 g, 136 mmol) and MsCl (23.3 g, 205 mmol) in 200 mL of dry DCM was added dropwise TEA (27.5 g, 273 mmol) at 0° C. The resulting mixture was stirred at room temperature overnight before concentrating to dryness. The residue was dissolved in 300 mL of EtOAc and washed with 1 N HCl and brine, dried over anhydrous Na2SO4 and concentrated to afford crude title compound: LC-MS m/z 244 (M+1)$^+$;

Step D: 4-ethenyl-2-fluorobenzonitrile

A solution of 2-(4-cyano-3-fluorophenyl)ethyl methanesulfonate (35.0 g, 144 mmol) and triethylamine (50 mL) in DCM (200 mL) was added DBU (50 mL) dropwise to at 0° C. After stirring at room temperature overnight, the solution was diluted with DCM, washed with 1 N HCl and brine, and dried over anhydrous sodium sulphate and concentrated. The residue was purified by column chromatography to give title compound.

Step E: 2-fluoro-4-oxiran-2-ylbenzonitrile

To a solution of 4-ethenyl-2-fluorobenzonitrile (18.0 g, 122 mmol) in 200 mL of DCM was slowly added mCPBA (74.8 g, 367.347 mmol) in portions at 0° C. The mixture was warmed to room temperature and stirred overnight. The solution was washed with aqueous Na$_2$SO$_3$ until KI paper didn't change color. The organic layers was washed with brine and then concentrated. The residue was purified via column chromatography to give 2-fluoro-4-oxiran-2-ylbenzonitrile: $^1$H-NMR (400 MHz, CDCl$_3$) δ ppm 7.59-7.62 (m, 1H), 7.12-7.22 (m, 2H), 3.89-3.91 (m, 1H), 3.20-3.22 (m, 1H), 2.72-2.74 (m, 1H).

INTERMEDIATE 24

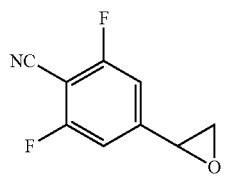

2,6-difluoro-4-(oxiran-2-yl)benzonitrile

Step A: 2,6-difluoro-4-vinylbenzonitrile 2,6-Difluoro-4-vinylbenzonitrile was prepared from 4-bromo-2,6-difluorobenzonitrile using potassium vinyl trifluoroborate and PdCl$_2$(dppf)2 in an analagous fashion as described for 4-ethenyl-3-methyl-2-(methyloxy)benzonitrile above.

Step B: 2,6-difluoro-4-(oxiran-2-yl)benzonitrile 2,6-Difluoro-4-(oxiran-2-yl)benzonitrile was prepared from 2,6-Difluoro-4-vinylbenzonitrile using mCPBA in an analagous fashion to that described for 5-fluoro-2-methoxy-4-(oxiran-2-yl)benzonitrile (Step H) above: $^1$H NMR (500 MHz, CDCl$_3$) δ 7.02 (d, J=8.0 Hz, 2H), 3.92 (dd, J=3.6, 2.4 Hz, 1H), 3.24 (dd, J=5.4, 4.0 Hz, 1H), 2.74 (dd, J=5.4, 2.4 Hz, 1H).

INTERMEDIATE 25

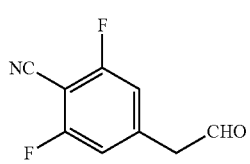

2,6-difluoro-4-(2-oxoethyl)benzonitrile

Step A: 2,6-difluoro-4-(2-hydroxyethyl)benzonitrile

To 2,6-difluoro-4-(oxiran-2-yl)benzonitrile (200 mg, 1.10 mmol) in ethanol (5.5 mL) was added Pd/C (42.3 mg, 0.397 mmol) and ammonium formate (209 mg, 3.31 mmol). The reaction mixture was vigorously stirred for 3 h, and was filtered through CELITE® to give the crude product, which was purified by column chromatography (0-100% EtOAc/hexanes) to give title compound.

Step B: 2,6-difluoro-4-(2-oxoethyl)benzonitrile

To 2,6-difluoro-4-(2-hydroxyethyl)benzonitrile (80.0 mg, 0.437 mmol) in DCM (2.2 mL) was added Dess-Martin periodinane (259 mg, 0.612 mmol). The reaction mixture was vigorously stirred for 1.5 h, and was diluted with saturated aqueous NaHCO$_3$ (2 mL) and Na$_2$S$_2$O$_3$ (2 mL), and stirred for 20 min. The aqueous layer was extracted with DCM (2×5 mL), and the organic layer was washed with brine, dried, and concentrated to give title compound. $^1$H NMR (500 MHz, CDCl$_3$) δ 9.81 (s, 1H), 6.97 (d, J=8.3 Hz, 2H), 3.89 (s, 2H).

INTERMEDIATE 26

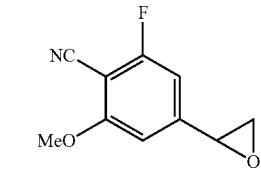

2-fluoro-6-methoxy-4-(oxiran-2-yl)benzonitrile

Step A: 4-bromo-2-fluoro-6-methoxybenzonitrile

To methanol (0.28 mL, 6.9 mmol) and 4-bromo-2,6-difluorobenzonitrile (1500 mg, 6.88 mmol) in THF (34 mL) was added NaHMDS (6.88 mL, 1.0 M in THF, 6.88 mmol) at 0° C. The reaction mixture was stirred at rt overnight, and diluted with brine, extracted with EtOAc. The organic layer was dried, and evaporated. The crude product was purified by column chromatography (0-30% EtOAc/Hex) to give 4-bromo-2-fluoro-6-methoxybenzonitrile.

Step B: 2-fluoro-6-methoxy-4-vinylbenzonitrile

The title compound was prepared from 4-bromo-2-fluoro-6-methoxybenzonitrile using potassium vinyl trifluoroborate and PdCl$_2$(dppf)2 in an analagous fashion as described for 4-ethenyl-3-methyl-2-(methyloxy)benzonitrile above.

Step C: 2-fluoro-6-methoxy-4-(oxiran-2-yl)benzonitrile

The title compound was prepared from 2-fluoro-6-methoxy-4-vinylbenzonitrile using mCPBA in an analagous fashion to that described for 5-fluoro-2-methoxy-4-(oxiran-2-yl)benzonitrile (Step H) above: $^1$H NMR (500 MHz, CDCl$_3$) 6.75 (dd, J=9.1, 0.9 Hz, 1H), 6.71 (d, J=0.9 Hz, 1H), 3.97 (s, 3H), 3.90 (dd, J=4.0, 2.5 Hz, 1H), 3.21 (dd, J=5.5, 4.0 Hz, 1H), 2.73 (dd, J=5.5, 2.5 Hz, 1H).

INTERMEDIATE 27

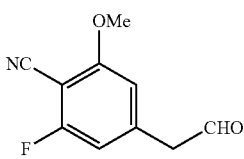

2-fluoro-6-methoxy-4-(2-oxoethyl)benzonitrile

Step A:
2-fluoro-4-(2-hydroxyethyl)-6-methoxybenzonitrile

To 2-fluoro-6-methoxy-4-(oxiran-2-yl)benzonitrile (200 mg, 1.10 mmol) in ethanol (5.2 mL) was added Pd/C (39.7 mg, 0.373 mmol) and ammonium formate (196 mg, 3.11 mmol). The reaction mixture was vigorously stirred for 3 h, and was filtered through CELITE® to give the crude product, which was purified by column chromatography (0-100% EtOAc/hexanes) to give title compound.

Step B:
2-fluoro-6-methoxy-4-(2-oxoethyl)benzonitrile

To 2-fluoro-4-(2-hydroxyethyl)-6-methoxybenzonitrile (80.0 mg, 0.437 mmol) in DCM (2.0 mL) was added Dess-Martin periodinane (243 mg, 0.574 mmol). The reaction mixture was vigorously stirred for 1.5 h, and was diluted with saturated aqueous NaHCO$_3$ (2 mL) and Na$_2$S$_2$O$_3$ (2 mL), and stirred for 20 min. The aqueous layer was extracted with DCM (2×5 mL), and the organic layer was washed with brine, dried, and concentrated to give title compound. $^1$H NMR (500 MHz, CDCl$_3$) δ 9.78 (t, J=1.4 Hz, 1H), 6.68 (d, J=8.9 Hz, 1H), 6.65 (s, 1H), 3.94 (s, 3H), 3.81 (d, J=1.4 Hz, 2H).

INTERMEDIATE 28

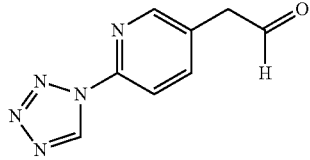

[6-(1H-tetrazol-1-yl)pyridin-3-yl]acetaldehyde

Step A: ethyl (6-nitropyridin-3-yl)acetate

To a suspension of NaH (60% in mineral oil, 13.8 g, 345 mmol) in 250 mL DMF in a 1 L flask with a magnetic stir bar was added tert-butyl ethyl propanedioate (65.3 mL, 345 mmol) maintaining the temperature below +12° C. in an ice bath over ~20 min (gas evolution). After 20 min, the ice bath was removed, allowed to warm to rt over 30 min. Commercially available 5-bromo-2-nitropyridine (50 g, 246 mmol) was added. A red suspension formed immediately. After 15 min, the reaction flask was placed in a 60° C. oil bath. After 1 h, the heating was turned off. The red-black slurry was allowed to stir overnight while cooling down. After 15 h at rt, the mixture was cooled in an ice bath. Additional 0.7 equiv NaH (60% in mineral oil, 6.90 g, 172 mmol) was added in ~10 portions below +10° C. (internal) to keep the foaming under control. After 30 min and 2/3 through the addition of NaH, the mixture turned very thick. Additional 100 mL DMF (2 volumes) was added to facilitate stirring. The rest of NaH was added over 10 min. Stirring in the ice bath was continued for additional 10 min. It is important to add NaH slowly in order to keep the exotherm and foaming under control. If all of NaH is added at the beginning of the reaction, it results in low yield and extensive decomposition. The cooling bath was removed, the mixture was allowed to stir to rt for 1 h. The reaction mixture was heated to 60° C. over 30 min, then was heated for the total of 3.5 h at 60° C. whereupon ~95% of the bromide had been consumed. The flask was then cooled in an ice bath. After 20 min in the ice bath, 100 mL MTBE was added followed by 300 mL of 1 M aqueous H$_3$PO$_4$ below +15° C. (pH=5). The red-black color of the reaction mixture sharply turned to light brown. The mixture was combined with 750 mL EtOAc, washed with 4×1 L water. The organic phase was concentrated. The resulting crude tert-butyl ethyl (6-nitropyridin-3-yl)propanedioate was dissolved in 153 mL DCM, and TFA (95 mL, 1230 mmol) was added. The mixture was stirred at 25° C. for 2 h, then was heated at 35° C. for 2 h, (80% conversion). An additional 2 equiv of TFA (39 mL, 492 mmol) was added. The mixture was heated at 35° C. for 1 h, then was kept at rt overnight (>95% conversion). The reaction was quenched with 1.0 L of 1 M aq K$_3$PO$_4$ in an ice bath below +20° C. to pH=6. The layers were separated, and the aqueous phase was extracted with an additional 200 mL of DCM. The organic phase was dried (MgSO$_4$), filtered, and concentrated. The residue was dissolved in 200 mL MTBE and the solution was filtered through 20 g of silica gel to remove tar. The silica plug was eluted with additional 750 mL MTBE. The filtrate was concentrated, the oily residue was suspended in ~100 mL of 3:1 Hexane/EtOAc. Crystallized occurred upon stirring/seeding. The suspension was filtered, and the filter cake washed with 100 mL of 5:1 hexane/EtOAc to provide the desired product. The mother liquors were concentrated, purified by flash chromatography on 7.5×18 cm silica (Hexane:EtOAc 3:1 to 3:2). The purest fractions were collected, concentrated to an oil, and treated with ~100 mL hexane to crystallize additional product. The slurry was stirred at rt for 1 h, filtered, the filter cake was washed with hexane to afford additional title compound.

Step B: ethyl (6-aminopyridin-3-yl)acetate

A suspension of 10% Pd on carbon (9.21 g, 8.66 mmol) in a solution of the ethyl (6-nitropyridin-3-yl)acetate (36.4 g, 173 mmol) in EtOH (364 mL) was hydrogenated at 20 psi and 25° C. for 2 h. The suspension was filtered through SOLKA FLOC® eluting with 200 mL EtOH. The filtrate was concentrated and solvent switched with EtOAc, then concentrated to afford the title compound.

Step C: ethyl [6-(1H-tetrazol-1-yl)pyridin-3-yl]acetate

A 1 L 3-neck flask was purged with nitrogen and charged with a solution of ethyl (6-aminopyridin-3-yl)acetate (31.7 g, 176 mmol) in EtOAc (317 mL) at +22° C. Then 30 mL of TMS trifluoroacetate was added (1.0 equiv) while cooling in a water bath. A mild exotherm to +25° C. and partial crystallization was observed. After 5 min, triethylorthoformate was added (44.0 mL, 264 mmol) followed by TMS-azide (28.0 mL, 211 mmol). The resulting suspension was stirred at +23° C. After 15 min, an additional 10 mL of TMS trifluoroacetate was added (0.30 equiv). A clear soln formed after ~10 min. The mixture was stirred for 3 days at +20° C.

whereupon a thin, light yellow suspension had formed. The mixture was cooled in an ice bath, and 200 mL of 1M aq $K_3PO_4$ was added while maintaining the temperature below +20° C. Then 465 mL EtOAc was added to solubilize the product. The layers were separated (pH of aq~8), then the organic phase was washed with 2×250 mL water, and concentrated to a thick slurry. Then 400 mL of n-heptane was added to the concentrated organic phase over 20 min. After 30 min, the suspension was filtered to afford the title compound.

Step D: 2-[6-(1H-tetrazol-1-yl)pyridin-3-yl]ethanol $LiBH_4$ (0.48 mL, 0.96 mmol, 2 M in THF) was added to a stirred solution of ethyl [6-(1H-tetrazol-1-yl)pyridin-3-yl] acetate (0.150 g, 0.64 mmol) in THF (20 ml) at 0° C. The resulting solution was stirred for 12 h. Water (5 ml) was added, and the resulting solution was extracted with dichloromethane (2×50 ml). The combined organic layers were dried over $MgSO_4$, filtered, and evaporated under reduced pressure to yield the product after flash chromatography (eluted with 10-50% ethyl acetate in hexanes). LC-MS (IE, m/z): 164.1 [$(M+1)^+$-28].

Step E: [6-(1H-tetrazol-1-yl)pyridin-3-yl]acetaldehyde

To a stirred solution of 2-[6-(1H-tetrazol-1-yl)pyridin-3-yl]ethanol (0.035 g, 0.18 mmol) in dry $CH_2Cl_2$ (20 mL) at 0° C. was added Dess-Martin periodinane (0.12 g, 0.28 mmol) in one portion. The mixture was stirred for 12 h at rt and quenched with a 1:1 mixture of saturated $Na_2S_2O_3$ (5 mL) and saturated $NaHCO_3$ (5 mL). The resulting mixture was diluted with $CH_2Cl_2$ (50 mL) and the layers were separated. The aqueous phase was extracted with $CH_2Cl_2$ (2×50 mL). The combined organic phases were washed with brine, dried ($Na_2SO_4$), and concentrated in vacuo to give crude title compound which was used directly. LC-MS (IE, m/z): 162.1 [$(M+1)^+$-28].

INTERMEDIATE 29

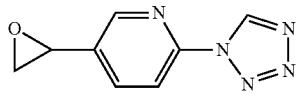

5-(Oxiran-2-yl)-2-(1H-tetrazol-1-yl)pyridine

Step A: 5-Bromo-2-(1H-tetrazol-1-yl)pyridine

To a mixture of 5-bromopyridin-2-amine (5.0 g, 28.9 mmol) in acetic acid (40 ml, 699 mmol) was added (diethoxymethoxy) ethane (7.70 ml, 46.2 mmol), followed by sodium azide (2.82 g, 43.3 mmol). The mixture was heated at 80° C. for 1 h. The reaction mixture was cooled to room temperature and diluted with water. The resulting precipitate was collected and dried under high vacuum to provide the title compound.

Step B: 5-Ethenyl-2-(1H-tetrazol-1-yl)pyridine

To a stirring solution of 5-bromo-2-(1H-tetrazol-1-yl) pyridine (1.0 g, 4.42 mmol), in EtOH (70 mL) were added bis[(diphenylphosphino)ferrocene]dichloropalladium(II), complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated to reflux (90° C., oil bath). Upon completion as determined by reverse phase HPLC-MS (1-2 h) and TLC (eluent: 10% ethyl acetate in hexanes), the reaction was cooled to room temperature, and then was diluted with water and extracted with EtOAc. The combined organic layers were washed with brine and dried over $MgSO_4$. The extracts were concentrated and chromatographed over a column of $SiO_2$ (0-20% EtOAc/hexanes as eluent). Evaporation of the solvent yielded the title compound. LC/MS $(M+1)^+$ =174.03.

Step C: 5-(Oxiran-2-yl)-2-(1H-tetrazol-1-yl)pyridine

A solution of 5-ethenyl-2-(1H-tetrazol-1-yl)pyridine (0.664 g, 3.83 mmol) in a 2:1 ratio of $H_2O$:t-BuOH (30 mL) was treated with N-bromosuccinimide in portions over 5 min (0.751 g, 4.22 mmol, 1.1 equiv) and stirred at 40° C. for 1 h. After cooling to 5° C., the reaction was basified with drop wise addition of solution of sodium hydroxide (0.46 g in 5 mL of $H_2O$, 11.50 mmol, 3 equiv) and stirred for another 1 h. The reaction mixture was poured into $H_2O$ (10 mL) and the product was precipitated out as white solid, filtered, washed with water, dried, yielding of the title compound. $^1$H NMR (500 MHz, DMSO-$d_6$), δ 10.17 (s, 1H), 8.60 (d, J=1.4 Hz, 1H), 8.04-7.99 (m, 2H), 4.14 (dd, J=2.7 Hz, J=2.8 Hz, 1H), 3.23 (t, J=4.6 Hz, 1H), 3.02 (dd, J=25 Hz, 1H); LC/MS $(M+1)^+$ =190.

INTERMEDIATE 30

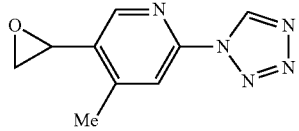

4-Methyl-5-(oxiran-2-yl)-2-(1H-tetrazol-1-yl)pyridine

The title compound was prepared in a similar fashion to that described for the synthesis of 5-(oxiran-2-yl)-2-(1H-tetrazol-1-yl)pyridine starting from commercially available 5-bromo-4-methylpyridin-2-amine to provide the title compound. $^1$H NMR (500 MHz, $CDCl_3$), δ 9.53 (s, 1H), 8.35 (s 1H), 7.93 (s, 1H), 4.07 (t, J=3.1 Hz, J=3.4 Hz, 1H), 3.29 (dd, J=4.6 Hz, J=4.1 Hz, 1H), 2.80 (dd, J=2.6 Hz, J=2.5 Hz, 1H), 2.60 (s, 3H); LC/MS $(M+1)^+$ =204.

INTERMEDIATE 31

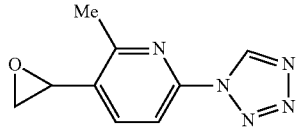

2-Methyl-3-(oxiran-2-yl)-6-(1H-tetrazol-1-yl)pyridine

The title compound was prepared in a similar fashion to that described for the synthesis of 5-(oxiran-2-yl)-2-(1H-tetrazol-1-yl)pyridine starting from 5-bromo-6-methylpyridin-2-amine to provide of the title compound. ¹H NMR (500 MHz, CDCl₃), δ 9.55 (s, 1H), 7.92 (d, J=8.2 Hz, 1H), 7.80 (d, J=8.2 Hz, 1H), 4.07 (t, J=2.8 Hz, J=3.6 Hz, 1H), 3.28 (dd, J=4.1 Hz, 1H), 2.73 (dd, J=2.5 Hz, 1H), 2.71 (s, 3H); LC/MS (M+1)⁺ =204.

INTERMEDIATE 32

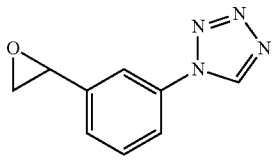

1-[3-(oxiran-2-yl)phenyl]-1H-tetrazole

Step A: 1-(3-bromophenyl)-1H-tetrazole

To a solution of 3-bromoaniline (1 g, 5.81 mmol) in glacial acetic acid (10 mL) was added triethyl orthoformate (2.90 mL, 17.4 mmol) and sodium azide (1.12 g, 17.4 mmol). The reaction mixture was heated at 80° C. for 3 hours in a sealed vial and then cooled to ambient temperature. Once cooled, water (10 mL) was added and the aqueous layer was extracted with ethyl acetate (3×20 mL). The combined organic layers were then dried over sodium sulfate, filtered and concentrated in vacuo to afford crude 1-(3-bromophenyl)-1H-tetrazole which was used without further purification. (M+H)⁺ 225.

Step B: 1-(3-ethenylphenyl)-1H-tetrazole

To a microwave vial was added 1-(3-bromophenyl)-1H-tetrazole (600 mg, 2.67 mmol), potassium vinyltrifluoroborate (536 mg, 4.00 mmol) and [1,1'-bis(diphenylphosphino)ferrocene]dichloropalladium(II) (9.80 mg, 0.133 mmol). The vial was sealed and vacuum purged with nitrogen three times. Anhydrous ethanol (10 mL, 0.05M) and triethylamine (0.743 mmol, 5.33 mmol) were added and degassed with nitrogen for 15 minutes. The reaction mixture was then heated to 80° C. for 3 hours, cooled, filtered over a pad CELITE®, and concentrated in vacuo. The crude residue was purified via MPLC (0-35% EtOAc/Hex gradient) to afford 1-(3-ethenylphenyl)-1H-tetrazole. (M+H)⁺ 173.

Step C: 1-[3-(oxiran-2-yl)phenyl]-1H-tetrazole

To an ice cooled DCM solution (10 mL) of 1-(3-ethenylphenyl)-1H-tetrazole (75 mg, 0.436 mmol) was added mCPBA (293 mg, 1.31 mmol). The reaction was warmed to ambient temperature, stirred for 15 hours and then quenched by the addition of aqueous sodium bicarbonate. The aqueous layer was extracted with DCM (3×25 mL). The combined organic layers were then dried over sodium sulfate, filtered and concentrated in vacuo. The crude residue was purified via MPLC (0-50% EtOAc/Hex gradient) to afford 1-[3-(oxiran-2-yl)phenyl]-1H-tetrazole. (M+H)⁺ 189.

INTERMEDIATE 33

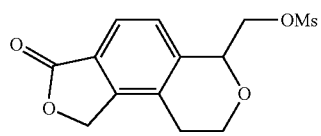

(3-oxo-3,6,8,9-tetrahydro-1H-furo[3,4-f]isochromen-6-yl)methyl-4-metylbenzenesulfonate Step A: 5-bromo-4-iodo-2-benzofuran-1 (3H]-one To a solution of 5-bromo-2-benzofuran-1(3H)-one (5.00 g, 23.5 mmol) at 0° C. in TfOH (100 mL) was added NIS (5.55 g, 24.6 mmol). The mixture was stirred at room temperature over night; LC analysis of the reaction mixture indicated completion of the reaction. The reaction mixture was then poured slowly into ice-water (1 L) with stirring. To the solution was then added EtOAc (500 mL) and subsequently stirred for 10 min. The mixture was filtered and the organic layer separated. The aqueous layer was extracted with EtOAc (2×200 mL). The combined organic layers were washed with water (500 mL), brine (500 mL), dried over Na₂SO₄, filtered, concentrated to dryness; it was absorbed into silica gel and separated with the solvent systems of (hexanes/EtOAc=1/1) to yield 5-bromo-4-iodo-2-benzofuran-1(3H]-one.

Step B: 5-bromo-4-prop-2-en-1-yl-2-benzofuran-1 (3H)-one

A mixture of 5-bromo-4-iodo-2-benzofuran-1(3H]-one (2.42 g, 7.13 mmol), allyltributyltin (2.36 g, 7.13 mmol), LiCl (1.50 g, 35.7 mmol) and Pd (PPh₃)₄ (200 g, 0.173 mmol) in toluene (50 mL) was heated at 90-100° C. under N₂ overnight; LC indicated that reaction had gone to completion, to the solution was poured EtOAc (100 mL) and washed with brine. The organic layer was dried over Na₂SO₄, filtered and concentrated to dryness, absorbed into silica gel and was then separated over silica gel column to give 5-bromo-4-prop-2-en-1-yl-2-benzofuran-1(3H)-one.

Step C: 5-bromo-4-(2-hydroxyethyl)-2-benzofuran-1 (3H)-one

To a solution of 5-bromo-4-prop-2-en-1-yl-2-benzofuran-1(3H)-one (1.27 g, 5.02 mmol) in MeOH (50 mL) and DCM (50 mL) was bubbled O₃ at −78° C. until the solution turned blue; excess ozone was removed on high vacuum. After the solution's color changed into colorless, NaBH₄ (0.8 g, 20 mmol) was added to the reaction mixture and subsequently stirred at room temperature for 30 min; LC and TLC indicated that reaction had gone to completion; solvent was removed on high vacuum, the residue was then re-dissolved in EtOAc and washed with water, dried over Na₂SO₄, filtered and concentrated to dryness. The organic residue was absorbed into silica gel and was separated on silica gel column to give 5-bromo-4-(2-hydroxyethyl)-2-benzofuran-1(3H)-one.

Step D: 5-ethenyl-4-(2-hydroxyethyl)-2-benzofuran-1(3H)-one

A mixture of 5-bromo-4-(2-hydroxyethyl)-2-benzofuran-1(3H)-one (0.460 g, 1.78 mmol), tributyl(vinyl)tin (0.676 g, 2.13 mmol), LiCl (0.224 g, 5.33 mmol) and Pd (PPh₃)4 (0.10 g, 0.087 mmol) in toluene (50 mL) was heated at 100-110° C. under N₂ overnight; TLC indicated that reaction had gone to completion and to the solution was poured EtOAc (100 mL) and washed with brine, water, dried over Na₂SO₄, filtered and concentrated to dryness. The residue was then absorbed into silica gel and separated over silica column to give title compound.

Step E: 4-(2-hydroxyethyl)-5-oxiran-2-yl-2-benzofuran-1(3H)-one

5-Ethenyl-4-(2-hydroxyethyl)-2-benzofuran-1(3H)-one (1.2 g, 5.9 mmol) was added to a flask containing a stir bar. To the flask was then added dichloromethane (20 mL). The flask was placed in a cool bath of 0° C.; to the flask was poured mCPBA (1.5 g, 8.8 mmol) and the resulting mixture was stirred at room temperature for overnight; LC as well as TLC (hexanes/EtOAc=1/1) indicated that reaction had gone to completion. The solution was treated with dichloromethane and washed with NaHCO$_3$, Na$_2$S$_2$O$_3$, and water, the organic layer was then dried over Na$_2$SO$_4$, filtered and concentrated to dryness, it was then treated with AcOH (20 mL) and stirred overnight; LC indicated formation of cyclized product. The solvent was removed and the resulting residue was absorbed into silica gel and 6-(hydroxymethyl)-8,9-dihydro-1H-furo[3,4-f]isochromen-3(6H)-one was isolated with the solvent systems of hexanes/EtOAc (1/1).

Step F: (3-oxo-3,6,8,9-tetrahydro-1H-furo[3,4-f]isochromen-6-yl)methyl-4-methylbenzenesulfonate 6-(Hydroxymethyl)-8,9-dihydro-1H-furo[3,4-f]isochromen-3(6H)-one, in DCM (10 mL) was treated with p-Toluenesulfonyl chloride (0.40 g, 2.3 mmol); to the mixture was added pyridine (2 mL) and the resulting mixture stirred at room temperature for 12 h. TLC (hexanes/EtOAc=1/0.5) and LC indicated the consumption of starting material and formation of the desired product. Reaction mixture was treated with dichloromethane and washed with NaCl, water and dried over Na$_2$SO$_4$, filtered and concentrated to dryness, absorbed into silica gel and was then subjected for purification over silica gel; (3-oxo-3,6,8,9-tetrahydro-1H-furo[3,4-f]isochromen-6-yl)methyl-4-methylbenzenesulfonate was isolated with the solvent system of hexanes/EtOAc (1/0.5). $^1$H-NMR (400 MHz, CDCl$_3$) δ ppm 7.781 (d, J=8 Hz, 1H), 7.727 (d, J=8 Hz, 1H), 7.367 (d, J=8 Hz, 1H), 7.257 (d, J=8.5 Hz, 1H), 7.206 (d, J=8 Hz, 1H), 5.253 (s, 2H), 5.110 (s, 1H), 4.481-4.452 (m, 2H), 4.419-4.385 (m, 2H), 4.196-4.153 (m, 2H), 2.495 (s, 3H).

INTERMEDIATES 34A AND 34B

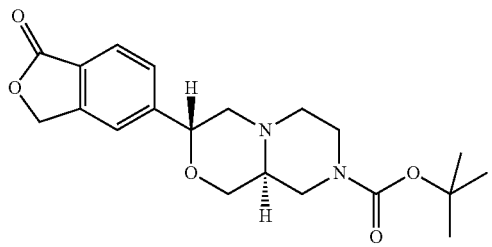

34A

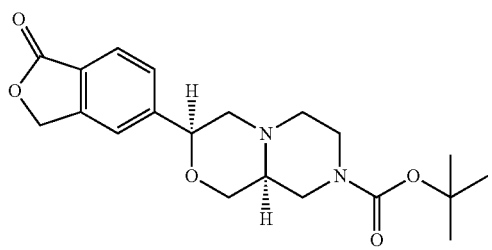

34B

34A: tert-butyl(3R,9aS)-3-(1-oxo-1,3-dihydro-2-benzofuran-5-yl)hexahydropyrazino[2,1-c][1,4]oxazine-8(1H)-carboxylate; 34B: tert-butyl(3S,9aS)-3-(1-oxo-1,3-dihydro-2-benzofuran-5-yl)hexahydropyrazino[2,1-c][1,4]oxazine-8(1H)-carboxylate

Step A: 5-ethenyl-2-benzofuran-1(3H)-one

5-Bromophthalide (50 g, 235 mmol), potassium vinyl trifluoroborate (62.9 g, 469 mmol), and PdCl$_2$(dppf)-CH$_2$Cl$_2$ Adduct (9.58 g, 11.7 mmol) were added to ethanol (500 mL) then TEA (65.4 mL, 469 mmol) was added. The reaction mixture was degassed then heated at reflux for 8 h. The reaction was worked up by diluting with ethyl acetate and washing with brine twice. The organic layer was dried and evaporated to dryness. The crude product was purified by MPLC (silica, 600 g column) with 25% EtOAc/hexane (3 L) then with 30% EtOAc/Hexane (2 L) to yield the title compound.

Step B: 5-(oxiran-2-yl)-2-benzofuran-1(3H)-one

5-Ethenyl-2-benzofuran-1(3H)-one (28.4 g, 177 mmol) was dissolved in DCM (400 mL) then mCPBA (47.7 g, 213 mmol) was added. The mixture was stirred at room temperature overnight. Some starting olefin remained. Another 25 g of mCPBA was added and the mixture was stirred overnight. The mixture was poured into ice cold Na$_2$SO$_3$ solution (saturated). The layers were separated and the organic layer was washed with 5% NaOH solution, brine, then was dried (MgSO$_4$). The crude product was purified by MPLC (330 g column, eluting with 40% EtOAc/hexane, 2 L, then with 45% EtOAc/hexane, 2 L, to afford 5-(oxiran-2-yl)-2-benzofuran-1(3H)-one. LC-MS: M+1=177.

Step C: tert-butyl(3S)-3-(hydroxymethyl)-4-[2-hydroxy-2-(1-oxo-1,3-dihydro-2-benzofuran-5-yl)ethyl]piperazine-1-carboxylate 5-(Oxiran-2-yl)-2-benzofuran-1(3H)-one (1.5 g, 8.5 mmol) and commercially available (S)-4-N-BOC-2-hydroxymethyl piperazine (2.394 g, 11.07 mmol) were combined in ethanol (10 mL) in a microwave tube. The mixture was degassed then heated for 60 min at 150° C. LC-MS showed the product peak. The reaction was worked up by adding ethyl acetate and washing once with brine. The organic layer was separated, dried, and concentrated to dryness. The crude product was purified by MPLC using an 80 g Redi-sep column and eluted with 50%-100% EtOAc/hexane yielding the title compound.

Step D: tert-butyl(9aS)-3-(1-oxo-1,3-dihydro-2-benzofuran-5-yl)hexahydropyrazino[2,1-c][1,4]oxazine-8(1H)-carboxylate tert-Butyl(3S)-3-(hydroxymethyl)-4-[2-hydroxy-2-(1-oxo-1,3-dihydro-2-benzofuran-5-yl)ethyl]piperazine-1-carboxylate (3.3 g, 8.4 mmol) and cyanomethylene tri-n-butylphosphorane (3.65 g, 15.1 mmol) were dissolved in 30 mL of benzene, the solution was degassed, and then heated to 100° C. for 3 h. LC-MS showed the product peak (M+1=389). The reaction mixture was cooled and evaporated to dryness. The residue was purified by MPLC through a 330 g Redi-sep column and eluted with a 15% acetone/85% hexane mixture to yield a cis-trans mixture of the title compound.

Step E: tert-butyl(3R,9aS)-3-(1-oxo-1,3-dihydro-2-benzofuran-5-yl)hexahydropyrazino[2,1-c][1,4]oxazine-8(1H)-carboxylate and tert-butyl(3S,9aS)-3-(1-oxo-1,3-dihydro-2-benzofuran-5-yl)hexahydropyrazino[2,1-c][1,4]oxazine-8(1H)-carboxylate The cis-trans isomer mixture from the prior step was separated using a ChiralCEL OD 4.6×250 mm 10μ column eluting with a 45% IPA/55% heptane solvent system. The trans-isomer 34A eluted first at 11.46 min and the cis-isomer 34B second at 17.43 min. 34A: $^1$H-NMR (500 MHz, CDCl$_3$): δ ppm 7.915 (d, J=8 Hz, 1H), 7.56 (s, 1H), 7.52 (d, J=8 Hz, 1H), 5.33 (s, 2H), 4.81 (dd, J=2 Hz, 10.5 Hz, 1H), 4.03-4.07 (m, 2H), 4.00 (dd, J=3, 11.25 Hz, 1H), 3.51 (t, J=10.5 Hz, 1H), 3.04 (b, 1H), 2.96 (dd J=2, 11.75 Hz, 1H), 2.76 (d, J=10.5 Hz, 1H), 2.57 (b, 1H), 2.21-2.32 (m, 3H), 1.5 (s, 9H). 34B: $^1$H-NMR (500 MHz, CDCl$_3$): δ ppm 7.95 (d, J=8 Hz, 1H), 7.72 (d, J=8 Hz, 1H), 7.70 (s, 1H), 5.37 (s, 2H), 4.91 (t, J=3.5 Hz, 1H), 3.65-4.07 (b, 2H), 3.64 (dd, J=3, 11.5 Hz, 1H), 3.40 (t, J=11.5 Hz, 1H), 3.29 (dd, J=3.5, 12 Hz, 1H), 3.02 (b, 1H), 2.82 (dd, J=3.5, 12 Hz, 2H), 2.66-2.67 (b, 1H), 2.50 (t, J=11 Hz, 2H), 1.5 (s, 9H).

INTERMEDIATES 35A AND 35B

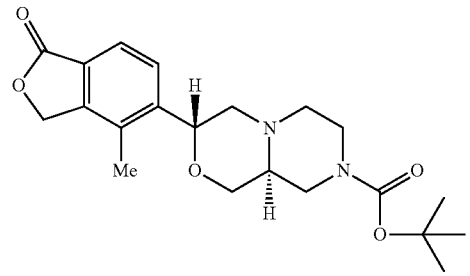

35A

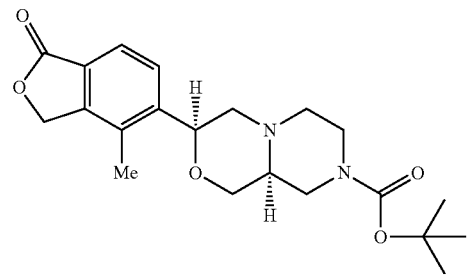

35B

35A: tert-butyl(3R,9aS)-3-(4-methyl-1-oxo-1,3-dihydro-2-benzofuran-5-yl)hexahydropyrazino[2,1-c][1,4]oxazine-8(1H)-carboxylate and 35B: tert-butyl(3S,9aS)-3-(4-methyl-1-oxo-1,3-dihydro-2-benzofuran-5-yl)hexahydropyrazino[2,1-c][1,4]oxazine-8(1H)-carboxylate Step A: tert-butyl(3S)-3-(hydroxymethyl)-4-[2-hydroxy-2-(4-methyl-1-oxo-1,3-dihydro-2-benzofuran-5-yl)ethyl]piperazine-1-carboxylate 4-Methyl-5-oxiran-2-yl-2-benzofuran-1(3H)-one (3.00 g, 15.8 mmol) and (S)-4-N-BOC-2-hydroxymethylpiperazine (5.12 g. 23.7 mmol) were suspended in ethanol (10 mL) in a 20 mL microwave tube. The reaction mixture was degassed and heated in a microwave apparatus for 30 min at 150° C. The reaction mixture was evaporated to dryness, then chromatographed through a 330 g Redi-sep column and eluted with a solvent system of 1:1 EtOAc/hexane to 100% EtOAc to yield the title compound. LC-MS: M+1=407.

Step B: tert-butyl(9aS)-3-(4-methyl-1-oxo-1,3-dihydro-2-benzofuran-5-yl)hexahydropyrazino[2,1-c][1,4]oxazine-8(1H)-carboxylate tert-Butyl(3S)-3-(hydroxymethyl)-4-[2-hydroxy-2-(4-methyl-1-oxo-1,3-dihydro-2-benzofuran-5-yl)ethyl]piperazine-1-carboxylate (3.3 g, 8.2 mmol) and cyanomethylene tri-n-butylphosphorane (2 equivalents) were dissolved in 45 mL benzene in a sealed and degassed tube. The mixture was heated to 100° C. for 3 h. The reaction mixture was cooled and evaporated to dryness. The residue was purified by chromatography through a 330 g Redi-sep column and eluted with 30% acetone/70% hexane mixture to yield the title compound as a cis-trans mixture. LC-MS: M+1=389.

Step C: Intermediates 35A and 35B

The cis/trans mixture of the product of Step B was separated using a Chiralpak AD 4.6×250 mm 10 g column with a 30% IPA/70% heptane solvent system. The trans isomer 35A eluted first and the cis-isomer 35B second. 35A: $^1$H-NMR (500 MHz, CDCl$_3$): δ ppm 7.82 (d, J=8 Hz, 1H) 7.73 (d, J=8 Hz, 1H), 5.28 (s, 2H), 4.97 ppm (dd, J=2.5, 10 Hz, 1H), 4.02 (dd, J=2.5, 11 Hz, 1H), 3.87-4.18 ppm (b, 2H) 3.53 ppm (t, J=11 Hz, 1H), 3.04 (b, 1H), 2.88 ppm (d, J=12 Hz, 1H), 2.76 (d, J=11.5 Hz, 1H), 2.54-2.59 (b, 1H), 2.36 (s, 3H), 2.22-2.34 (m, 3H), 1.50 (s, 9H): LC-MS: M+1=389.
35B: $^1$H-NMR (500 MHz, CDCl$_3$): δ ppm 8.12 (d, J=8 Hz, 1H), 7.79 (d, J=8 Hz, 1H), 5.29 (s, 2H), 5.01 (t, J=4 Hz, 1H), 3.69-4.03 (b, 2H), 3.62 (t, J=8.5 Hz, 1H), 3.38 (t, J=7.5 Hz, 1H), 3.23 (dd, J=4, 12 Hz, 1H), 3.09-3.20 ppm (b, 1H), 2.81 (dd, J=4, 12 Hz, 1H), 2.69-2.90 ppm (b, 2H), 2.55-2.58 (b, 2H), 2.38 ppm (s, 3H), 1.50 ppm (s, 9H): LC-MS: M+1=389.

INTERMEDIATES 35C AND 35D

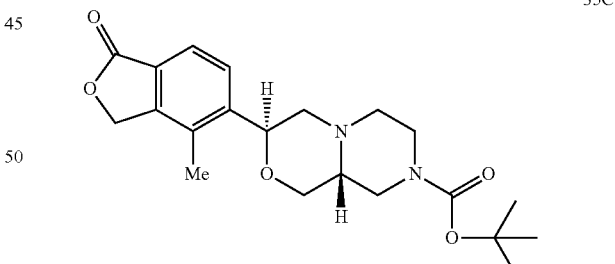

35C

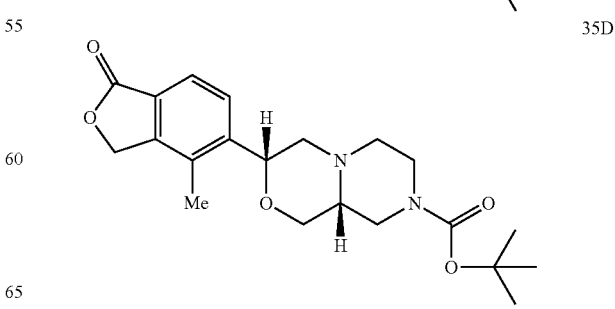

35D

35C: tert-butyl(3S,9aR)-3-(4-methyl-1-oxo-1,3-di-
hydro-2-benzofuran-5-yl)hexahydropyrazino[2,1-c]
[1,4]oxazine-8(1H)-carboxylates 35D: tert-butyl(3R,9aR)-3-(4-methyl-1-oxo-1,3-
dihydro-2-benzofuran-5-yl)hexahydropyrazino[2,1-
c][1,4]oxazine-8(1H)-carboxylate Intermediates 35C and 35D were made in a similar fashion to that described above for 35A and 35B, except (R)-4-N-BOC-2-hydroxymethylpiperazine was used in place of (S)-4-N-BOC-2-hydroxymethylpiperazine. The cis-trans isomers 35C and 35D were separated using a Chiral-CEL OD 4.6×250 mm 10 g column with the 20% IPA/80% heptane solvent system. The trans-isomer 35C eluted first and the cis-isomer 35D eluted second: 35C: $^1$H-NMR (500 MHz, CDCl$_3$): δ ppm 7.82 (d, J=8 Hz, 1H) 7.73 (d, J=8 Hz, 1H), 5.28 (s, 2H), 4.97 (dd, J=2.5, 10 Hz, 1H), 4.02 (dd, J=3, 11 Hz, 1H), 4.05-4.20 (b, 2H) 3.53 (t, J=4 Hz, 1H), 3.05 (b, 1H), 2.88 (dd, J=2, 11.7 Hz, 1H), 2.75 (d, J=10.5 Hz, 1H), 2.55 (b, 1H), 2.36 (s, 3H), 2.22-2.36 (m, 3H), 1.51 (s, 9H); LC-MS: M+1=389. 35D: $^1$H-NMR (500 MHz, CDCl$_3$): δ ppm 8.12 (d, J=7.8 Hz, 1H), 7.79 (d, J=8 Hz, 1H), 5.30 (d, J=1.8, 2H), 5.02 (t, J=3.85 Hz, 1H), 3.70-4.05 (b, 2H), 3.62 (dd, J=3, 11.65 Hz, 1H), 3.37 (t, J=9 Hz, 1H), 3.23 (dd, J=4, 12 Hz, 1H), 3.10 (b, 1H), 2.80-2.86 (m, 3H), 2.57 (b, 2H), 2.38 ppm (s, 3H), 1.50 ppm (s, 9H); LC-MS: M+1=389.

INTERMEDIATES 36A AND 36B

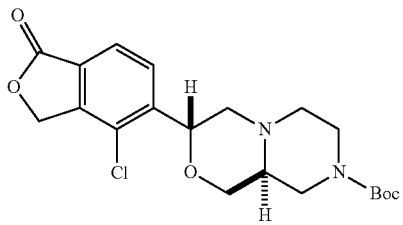

36A

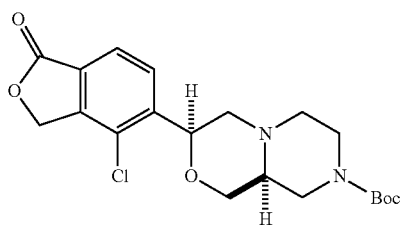

36B

36A: tert-butyl (3R,9aS)-3-(4-chloro-1-oxo-1,3-
dihydro-2-benzofuran-5-yl)hexahydropyrazino[2,1-
c][1,4]oxazine-8(1H)-carboxylate 36B: tert-butyl (3S,9aS)-3-(4-chloro-1-oxo-1,3-di-
hydro-2-benzofuran-5-yl)hexahydropyrazino[2,1-c]
[1,4]oxazine-8(1H)-carboxylate Step A: 2-chloro-3-(hydroxymethyl)phenol To a solution of 2-chloro-3-hydroxybenzaldehyde (8.10 g, 51.7 mmol) in MeOH was added NaBH$_4$ (1.96 g, 51.7 mmol) at 0° C. The reaction was allowed to stir for 30 minutes. TLC showed clean conversion to a more polar spot. The reaction was diluted with EtOAc (400 mL), washed with water and brine, dried over sodium sulfate, and concentrated. The crude product was used in Step B without further purification.

Step B: 4-bromo-2-chloro-3-(hydroxymethyl)phenol

To the flask charged with 2-chloro-3-(hydroxymethyl) phenol from Step A and a stir bar was added NBS (10.8 g, 60.5 mmol) and TFA (50 mL). The reaction was allowed to stir for 16 hours at RT. TLC showed complete reaction at that point. The solvent was removed under vacuum. The residue was re-dissolved in EtOAc, washed with water, and purified by silica gel flash chromatography. A pair of regio-isomers was collected from the separation. The less polar spot was the desired 4-bromo-2-chloro-3-(hydroxymethyl) phenol according to noe NMR analysis.

Step C:
4-chloro-5-hydroxy-2-benzofuran-1(3H)-one

To a flask charged with 4-bromo-2-chloro-3-(hydroxymethyl)phenol (2.44 g, 10.3 mmol) and a stir bar was added CuCN (2.76 g, 30.8 mmol) and DMF (25 mL). The flask was fitted with a condenser and purged three times with Nitrogen. The solution was then heated to 145° C. for 2 hours. At that point, water (0.555 mL, 30.8 mmol) was added to the reaction via a syringe, and the reaction was kept at 100° C. for another 24 hours. The reaction was cooled to RT, diluted with DCM (100 mL), and filtered through a pad of CELITE® to remove the solids. The filtrate was washed with saturated NH$_4$OAc, dried over sodium sulfate, concentrated and purified by silica gel flash chromatography. 4-Chloro-5-hydroxy-2-benzofuran-1(3H)-one was collected after removal of solvents.

Step D: 4-chloro-5-ethenyl-2-benzofuran-1(3H)-one

To a cold solution of 4-chloro-5-hydroxy-2-benzofuran-1(3H)-one (1.39 g, 7.53 mmol) in DCM (25 mL) was added Hunig's Base (3.29 mL, 18.8 mmol) and trifluoromethanesulfonic anhydride (2.54 mL, 15.1 mmol). The mixture was allowed to stir for 16 hours. Analysis by TLC showed complete consumption of all SM. The reaction was diluted with Hexane and washed with water. The solution was dried with sodium sulfate, concentrated, and purified by flash chromatography on a silica column. The solvent was removed under reduced pressure to give intermediate triflate: LC-MS (M+1=317). To the triflate was added a stir bar, potassium vinyltrifluoroborate (1.33 g, 9.90 mmol), PdCl$_2$ (dppf) (0.243 g, 0.332 mmol), triethylamine (1.89 mL, 13.3 mmol), and iso-propanol (50 mL). The mixture was purged three times with nitrogen, and heated to 60° C. for 2 hours. TLC showed complete reaction at that point. Most of the solvent was removed under vacuum. The crude residue was diluted with EtOAc (200 mL), washed with brine, dried over sodium sulfate, adsorbed onto silica gel, and purified by flash chromatography to give the title compound.

Step E: 4-chloro-5-oxiran-2-yl-2-benzofuran-1(3H)-
one

To a solution of 4-chloro-5-ethenyl-2-benzofuran-1(3H)-one (1.1 g, 5.7 mmol) in DCM (40 mL) was added mCPBA (1.9 g, 8.5 mmol). The solution was stirred at RT for 16 hours. Analysis by TLC and LC showed formation of the desired product, along with some untouched starting material. The reaction was diluted with DCM (200 mL), washed with aqueous Na₂S₂O₃ and Na₂CO₃, dried over sodium sulfate, concentrated, and purified by silica gel flash chromatography to afford the title compound.

Step F-G: tert-butyl (3R,9aS)-3-(4-chloro-1-oxo-1,3-dihydro-2-benzofuran-5-yl)hexahydropyrazino[2,1-c][1,4]oxazine-8(1H)-carboxylate and tert-butyl (3S,9aS)-3-(4-chloro-1-oxo-1,3-dihydro-2-benzofuran-5-yl)hexahydropyrazino[2,1-c][1,4]oxazine-8(1H)-carboxylate The title compounds were prepared from 4-chloro-5-(oxiran-2-yl)-2-benzofuran-1(3H)-one in two steps in an analogous fashion as that described for the synthesis of tert-butyl(3R,9aS)-3-(4-methyl-1-oxo-1,3-dihydro-2-benzofuran-5-yl)hexahydropyrazino[2,1-c][1,4]oxazine-8(1H)-carboxylate and tert-butyl(3S,9aS)-3-(4-methyl-1-oxo-1,3-dihydro-2-benzofuran-5-yl)hexahydropyrazino[2,1-c][1,4]oxazine-8(1H)-carboxylate. The crude product mixture was adsorbed onto silica gel, and purified by flash chromatography. The top product spot was determined by NMR to be the trans-isomer tert-butyl (3R,9aS)-3-(4-chloro-1-oxo-1,3-dihydro-2-benzofuran-5-yl)hexahydropyrazino[2,1-c][1,4]oxazine-8(1H)-carboxylate 36A, and more polar product spot was the cis-isomer tert-butyl (3S,9aS)-3-(4-chloro-1-oxo-1,3-dihydro-2-benzofuran-5-yl)hexahydropyrazino[2,1-c][1,4]oxazine-8(1H)-carboxylate 36B: ¹H-NMR (500 MHz, CDCl₃) δ ppm 36A: 7.83 (d, J=7.5 Hz, 1H), 7.78 (d, J=8.0 Hz, 1H), 5.26 (s, 2H), 5.10 (d, J=10.5 Hz, 1H), 3.98 (d, J=11.5 Hz, 1H), 3.90 (broad, 1H), 3.52 (t, J=10.5 Hz, 1H), 3.05 (d, J=11.5 Hz, 1H), 3.03 (broad, 1H), 2.75 (d, J=11 Hz, 1H), 2.54 (broad, 1H), 2.30 (t, J=10 Hz, 1H), 2.22 (t, J=11 Hz, 1H), 2.07 (t, J=10.5 Hz, 1H), 1.46 (s, 9H); 36B: 8.20 (d, J=7.5 Hz, 1H), 7.82 (d, J=8.0 Hz, 1H), 5.28 (s, 2H), 5.13 (s, 1H), 3.85 (broad, 1H), 3.71 (d, J=11.5, 1H), 3.49 (m, 1H), 3.09 (dd, J=12, 5.0 Hz, 1H), 3.05 (m, 1H), 2.91 (m, 1H), 2.88-2.80 (m, 2H), 2.64 (m, 1H), 1.47 (s, 9H).

INTERMEDIATE 37

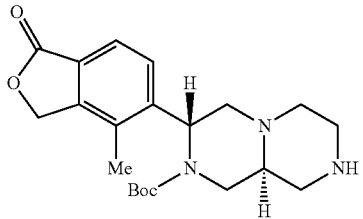

(3R,9aS)-tert-butyl 3-(4-methyl-1-oxo-1,3-dihydroisobenzofuran-5-yl)hexahydro-1H-pyrazino[1,2-a]pyrazine-2(6H)-carboxylate Step A: (S)-tert-butyl 4-((S)-2-hydroxy-2-(4-methyl-1-oxo-1,3-dihydroisobenzofuran-5-yl)ethyl)-3-(hydroxymethyl)piperazine-1-carboxylate (S)-4-methyl-5-(oxiran-2-yl)isobenzofuran-1(3H)-one (0.75 g, 3.95 mmol) and (S)-tert-butyl 3-(hydroxymethyl)piperazine-1-carboxylate (1.024 g, 4.73 mmol) in ethanol (12 ml) was heated in microwave at 150° C. for 1.5 h. The reaction solution was concentrated and the residue was purified on Biotage using 40-100% ethyl acetate/hexane to give the title compound. LC/MS: (M+1)⁺: 407.15.

Step B: (S)-benzyl 4-((S)-2-hydroxy-2-(4-methyl-1-oxo-1,3-dihydroisobenzofuran-5-yl)ethyl)-3-(hydroxymethyl)piperazine-1-carboxylate To the solution of (S)-tert-butyl 4-((S)-2-hydroxy-2-(4-methyl-1-oxo-1,3-dihydroisobenzofuran-5-yl)ethyl)-3-(hydroxymethyl)piperazine-1-carboxylate (2.57 g, 6.32 mmol) in methylene chloride (3 mL) was added trifluoroacetic acid (10 ml, 130 mmol) at rt for 1 h. After removing the volatile the residue was dissolved in methylene chloride (100 mL). To this solution was added triethylamine (4.40 ml, 31.6 mmol) and benzyl chloroformate (0.947 ml, 6.64 mmol) at 0° C. for 0.5 h. The reaction was quenched by water followed by addition of saturated sodium carbonate. The mixture was extracted with methylene chloride, dried over sodium sulfate, concentrated and the residue was purified on Biotage using 40-100% EtOAc/hexane to give the title compound. LC/MS: (M+1)⁺: 441.11.

Step C: (9aR)-benzyl 8-allyl-7-(4-methyl-1-oxo-1,3-dihydroisobenzofuran-5-yl)hexahydro-1H-pyrazino[1,2-a]pyrazine-2(6H)-carboxylate A solution of (S)-benzyl 4-((S)-2-hydroxy-2-(4-methyl-1-oxo-1,3-dihydroisobenzofuran-5-yl)ethyl)-3-(hydroxymethyl)piperazine-1-carboxylate (1.4 g, 3.18 mmol) in thionyl chloride (20 mL, 274 mmol) was heated at reflux for 1 h. After removing the volatile, the residue was dissolved in N,N-dimethylformamide (20 mL) and treated with allylamine (1.311 mL, 17.48 mmol) at 0° C. The resulting solution was treated with sodium iodide (0.088 g, 0.318 mmol) and heated at 90° C. for 1 h. The solution was diluted in ethyl acetate (300 mL) and was washed with saturated sodium bicarbonate three times, dried over sodium sulphate concentrated and the residue was purified on Biotage using 40-100% ethyl acetate/hexane to give the title compound. LC/MS: (M+1)⁺: 462.12.

Step D: (3S,9aS)-8-benzyl 2-tert-butyl 3-(4-methyl-1-oxo-1,3-dihydroisobenzofuran-5-yl)tetrahydro-1H-pyrazino[1,2-a]pyrazine-2,8(9H,9aH)-dicarboxylate A mixture of (9aR)-benzyl 8-allyl-7-(4-methyl-1-oxo-1,3-dihydroisobenzofuran-5-yl)hexahydro-1H-pyrazino[1,2-a]pyrazine-2(6H)-carboxylate (0.98 g, 2.123 mmol), 1,3-dimethylpyrimidine-2,4,6(1H,3H,5H)-trione (0.995 g, 6.37 mmol) and tetrakis(triphenylphosphine)palladium (0) (123 mg, 0.106 mmol) in methylene chloride (10 mL) was heated at 35° C. for 4 h. After cooling to rt, di-tert-butyl dicarbonate (556 mg, 2.55 mmol) and triethylamine (1194 μl, 8.49 mmol) were added and the resulting solution was stirred at rt overnight. After concentration, the residue was purified on Biotage using 20-100% EtOAc/hexane to give (3S,9aS)-8-benzyl 2-tert-butyl 3-(4-methyl-1-oxo-1,3-dihydroisobenzofuran-5-yl)tetrahydro-1H-pyrazino[1,2-a]pyrazine-2,8(9H,9aH)-dicarboxylate (less polar): LC/MS: (M+1)⁺: 522.12, ¹HNMR (500 MHz, CDCl₃) δ 8.250-8.050 (m, 1H), 7.763-7.747 (d, J=8.0 Hz, 1H), 7.406-7.395 (m, 5H), 5.292 (s, 2H), 5.181 (s, 2H), 4.174-4.096 (broad, 2H), 3.820-3.790 (broad, 1H), 3.123-3.088 (m, 2H), 2.772-2.667 (m, 5H), 2.335 (s, 3H), 2.214-2.172 (m, 2H), 1.595 (s, 9H); and (3R,9aS)-8-benzyl 2-tert-butyl 3-(4-methyl-1-oxo-1,3-dihydroisobenzofuran-5-yl)tetrahydro-1H-pyrazino[1,2-a]pyrazine-2,8(9H, 9aH)-dicarboxylate (more polar). LC/MS: (M+1)⁺: 522.12, ¹HNMR (500 MHz, CDCl₃) δ 7.758-7.742 (d, J=8.0 Hz, 1H), 7.698-7.681 (d, J=8.0 Hz, 1H), 7.398 (broad, 5H), 5.262 (s, 2H), 5.180 (s, 2H), 4.789-4.759 (m, 1H), 4.202-

4.130 (broad, 2H), 4.009-3.993 (m, 1H), 3.080 (broad, 1H), 2.903-2.849 (broad, 1H), 2.824-2.730 (broad, 3H), 2.359 (s, 3H), 2.329-2.311 (broad, 1H), 2.228-2.155 (m, 2H), 1.159 (s, 9H).

Step E: (3R,9aS)-tert-butyl 3-(4-methyl-1-oxo-1,3-dihydroisobenzofuran-5-yl)hexahydro-1H-pyrazino[1,2-a]pyrazine-2(6H)-carboxylate To a solution of (3R,9aS)-8-benzyl 2-tert-butyl 3-(4-methyl-1-oxo-1,3-dihydroisobenzofuran-5-yl)tetrahydro-1H-pyrazino[1,2-a]pyrazine-2,8(9H,9aH)-dicarboxylate (0.46 g, 0.882 mmol) in methanol (30 mL) was added palladium on carbon (10%, 0.094 g, 0.088 mmol) and the mixture was subjected to hydrogenation at rt overnight. After filtration the filtrate was concentrated to give the title compound. LC/MS: (M+1)$^+$: 388.10.

INTERMEDIATE 38

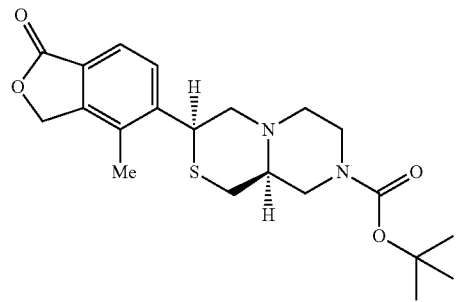

(3S,9aS)-tert-butyl 3-(4-methyl-1-oxo-1,3-dihydroisobenzofuran-5-yl)hexahydropyrazino[2,1-c][1,4]thiazine-8(1H)-carboxylate Step A: (S)-tert-butyl 4-((R)-2-hydroxy-2-(4-methyl-1-oxo-1,3-dihydroisobenzofuran-5-yl)ethyl)-3-(hydroxymethyl)piperazine-1-carboxylate The title compound was prepared starting from 4-methyl-5-[(2R)-oxiran-2-yl]-2-benzofuran-1(3H)-one in an analogous fashion to that described above for the synthesis of (S)-tert-butyl 4-((S)-2-hydroxy-2-(4-methyl-1-oxo-1,3-dihydroisobenzofuran-5-yl)ethyl)-3-(hydroxymethyl)piperazine-1-carboxylate.

Step B: (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate To the solution of (S)-tert-butyl 4-((R)-2-hydroxy-2-(4-methyl-1-oxo-1,3-dihydroisobenzofuran-5-yl)ethyl)-3-(hydroxymethyl)piperazine-1-carboxylate (817 mg, 2.01 mmol) in anhydrous THF (20 mL) under nitrogen atmosphere at 0° C. was added anhydrous triethylamine (0.560 mL, 4.02 mmol), followed by addition of methanesulfonyl chloride (0.234 mL, 3.01 mmol) and 4-dimethylaminopyridine (24.6 mg, 0.201 mmol). The ice bath was removed and the reaction mixture was stirred for 2 hours. The resulting mixture was then concentrated under reduced pressure. The resulting oil was redissolved in anhydrous DMSO (13 mL) and treated with potassium thioacetate (1235 mg, 10.81 mmol). The reaction mixture was stirred at room temperature under nitrogen for 2 hours. The mixture was diluted with ethyl acetate, washed with water (3 times), brine, and dried (MgSO$_4$), filtered and concentrated. The crude product was purified on Biotage SP1 (40+M equilibrated), eluting with 20-80% ethyl acetate/hexanes, 20 CV. LC/MS: [(M+1)]$^+$=465.2.

Step C: (3S)-tert-butyl 3-(acetylthiomethyl)-4-(2-chloro-2-(4-methyl-1-oxo-1,3-dihydroisobenzofuran-5-yl)ethyl)piperazine-1-carboxylate To a solution of (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate (573 mg, 1.233 mmol) in anhydrous toluene (12.3 mL) cooled with an ice bath was added thionyl chloride (0.268 mL, 3.70 mmol). Then, anhydrous pyridine (0.399 mL, 4.93 mmol) was added dropwise. The reaction mixture was kept at 0° C. for 20 min, then warmed to room temperature and stirred for 3 hours. TLC showed the consumption of the starting material. The reaction was concentrated under reduced pressure and dried on high vacuum overnight. The resulting product was used directly in the next step.

Step D: (3S,9aS)-tert-butyl 3-(4-methyl-1-oxo-1,3-dihydroisobenzofuran-5-yl)hexahydropyrazino[2,1-c][1,4]thiazine-8(1H)-carboxylate A solution of (3S)-tert-butyl 3-(acetylthiomethyl)-4-(2-chloro-2-(4-methyl-1-oxo-1,3-dihydroisobenzofuran-5-yl)ethyl)piperazine-1-carboxylate (596 mg, 1.234 mmol) in anhydrous THF (20 mL) was treated dropwise with sodium methoxide, 25% solution in methanol (0.846 mL, 3.70 mmol). The reaction mixture was stirred for 2 hours under nitrogen at room temperature. LCMS showed formation of the desired product. Solvent was removed under reduced pressure. Residue was redissolved in dichloromethane and washed with brine. The organic layer was dried over MgSO$_4$, filtered and concentrated. The residue was purified on Biotage SP1, eluting with 20-80% ethyl acetate/hexanes, 16 column volumes to provide the title compound: $^1$H NMR (500 MHz, CDCl$_3$) δ 8.64 (d, J=8.0 Hz, 1H), 7.77 (d, J=8.0 Hz, 1H), 5.29 (s, 2H), 3.81-4.20 (m, 3H), 3.38 (dd, J=2.3, 12.6 Hz), 3.00-3.22 (m, 2H), 2.57-2.82 (m, 2H), 2.24-2.56 (m, 7H), 1.51 (s, 9H).

INTERMEDIATE 39

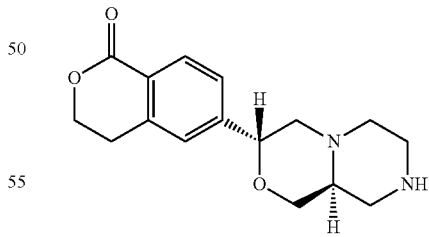

6-[(3R,9aS)-octahydropyrazino[2,1-c][,4]oxazin-3-y]-3,4-dihydro-1H-isochromen-1-one Step A: 6-bromo-3,4-dihydro-1H-isochromen-1-one Method A:
A 250-mL, three-necked, round-bottomed flask equipped with a septum, nitrogen inlet needle, and thermocouple was charged with diisopropylamine (3.10 g, 30.6 mmol) and 30 mL of THF. The reaction mixture was cooled at −20° C. while n-BuLi (2.5 M, 12.2 mL, 30.6 mmol) was added dropwise via syringe keeping the internal temperature below 0° C. The resulting reaction mixture was stirred at 0° C. for 15 min. The reaction mixture was then cooled at −40° C. while 4-bromo-2-methylbenzonitrile (4.00 g, 20.4 mmol) in 10 mL of THF was added dropwise via syringe over 1 h. An internal temperature of ca. −40° C. was maintained during the addition. The resulting reaction mixture was stirred at −40° C. for 30 min and then charged with DMF (2.98 g, 40.8 mmol, ca. 50 ppm water) in one portion. The reaction mixture was stirred at −40° C. for 15 min. The reaction mixture was quenched with MeOH (5 vol., 20 mL) and then charged with $NaBH_4$ (0.770 g, 20.4 mmol) in one portion and allowed to warm to room temperature. After complete reduction of intermediate aldehyde (as judged by HPLC analysis), the reaction mixture was carefully quenched with 5 M HCl (with cooling) to adjust the pH to 2-3. The reaction mixture was extracted with EtOAc and then solvent-switched to EtOH (40 mL). $H_2SO_4$ (98%, 20.0 g, 204 mmol) was added in one portion and the resulting reaction mixture was stirred at reflux for 24 h. After complete cyclization (monitored by HPLC analysis), the reaction mixture was cooled to room temperature and then solvent-switched to EtOAc. The resulting organic layer was washed with water, brine, and solvent-switched to MTBE. Precipitation from 1:1 MTBE:heptane afforded 6-bromo-3,4-dihydro-1H-isochromen-1-one.

Step A, Method B:

A solution of DIPA (4 M, 270 mL, 1080 mmol) in THF (900 mL) was cooled to −65° C. and hexyl lithium (2.1 M, 505 mL, 1060 mmol) was added dropwise over 15 min maintaining the internal temp <−55° C. Upon completion of the addition, the reaction mixture was warmed up to −40° C. where it was stirred 30 min. To the resulting solution of LDA was added 4-bromo-2-methylbenzoic acid (90 g, 419 mmol) slowly (over 15 min) as a solution in THF (400 mL). The reaction mixture was stirred for 30 min at −40° C. and then warmed to 15° C. at which point paraformaldehyde (50.30 g, 1674 mmol) was added in 3 portions as a solid keeping the internal temperature (ice water bath) below <18° C. Stirring was then continued at room temperature for 1 hour. After a second hour of stirring, the vessel was immersed in an ice water bath and 3N HCl (650 mL) was added at such a rate to keep the internal temperature less than 30° C. The contents of the reaction vessel was subsequently transferred to a separatory funnel where it was extracted 3×400 mL EtOAc and the combined organic phases were then concentrated to ~800 mL total volume. To this was added Amberlyst 15 resin (12 g) and the resulting mixture stirred at 48° C. overnight (~14 h). HPLC analysis the following morning indicated that cyclization to the desired 6-bromo-3,4-dihydro-1H-isochromen-1-one was nearly complete. The resin was removed by filtration and the solution concentrated to ~200 mL total volume at which point the desired product began to precipitate and the solids were then collected by filtration. The cake was subsequently washed with MTBE (2×80 mL) to give the first crop of product. Additional material was salvaged by washing the collected supernatant 2× with 200 mL 10% $K_2CO_3$,aq followed by 200 mL 1M $H_3PO_4$. After concentration to ~100 mL the precipitated material was collected by filtration, washed with MTBE and then combined with the first crop of 6-bromo-3,4-dihydro-1H-isochromen-1-one and dried.

Step B:
6-(bromoacetyl)-3,4-dihydro-1H-isochromen-1-one

6-Bromo-3,4-dihydro-1H-isochromen-1-one (6.90 g, 30.4 mmol), tributyl(1-ethoxyethenyl)stannane (10.8 mL, 31.9 mmol, 1.05 equiv), and $PdCl_2(PPh_3)_2$ (1.07 g, 1.52 mmol, 0.05 equiv) were weighed into a 250 mL round bottom flask. To this was added dioxane (70 mL) and the resulting mixture stirred at 80° C. for 4 h. The reaction was not complete by HPLC, therefore another 0.1 equiv of tin reagent was added. After 30 min 6-bromo-3,4-dihydro-1H-isochromen-1-one had been fully consumed as indicated by HPLC. The reaction mixture was cooled to 0° C. and 35 mL THF followed by 14 mL $H_2O$ were added. To this was introduced solid N-bromosuccinimide (5.68 g, 31.9 mmol, 1.05 equiv), added in portions over 5 min. After stirring for 30 min there was still evidence of remaining enol ether, therefore NBS was added in small portions (~300 additional mg added) until it was consumed as evidenced by HPLC. Water was then added and the mixture extracted with EtOAc. The aqueous layer was extracted 2 additional times with EtOAc, the combined organics dried with $MgSO_4$, filtered and concentrated in vacuo. This was transferred with EtOAc to a 100 mL round bottom flask, the resulting solution concentrated to ~25 mL total volume, at which point hexane (50 mL) was added dropwise. When complete the heterogeneous mixture was stirred for 30 min, then cooled to 0° C. and stirred for 10 min, then filtered and washed twice with hexanes. The desired product was dried under a nitrogen bag, then purified by flash chromatography (12 to 100% EtOAc/Hex) to provide the title compound.

Step C: tert-butyl(9aS)-3-hydroxy-3-(1-oxo-3,4-dihydro-1H-isochromen-6-yl)hexahydropyrazino[2,1-c][1,4]oxazine-8(1H)-carboxylate 6-(Bromoacetyl)-3,4-dihydro-1H-isochromen-1-one (~1.54 g, ~5.72 mmol, presence of c-chloroketone was noted, ~10%) and commercially available (S)-4-N-BOC-2-hydroxymethylpiperazine (1.24 g, 5.72 mmol) were added to a round bottom flask and diluted with THF (50 mL). Diisopropylethylamine (1.30 mL, 7.44 mmol) was then introduced and the mixture left stirring for 14 h at RT during which time a considerable amount of solid had formed (presumably HBr salt of DIPEA). The reaction mixture was diluted with EtOAc, then washed with saturated $NH_4Cl_{aq}$ followed by $H_2O$. Both aqueous layers were sequentially back extracted once with another portion of EtOAc, the organics were then combined, dried with $MgSO_4$, filtered, and concentrated in vacuo. The recovered crude product was subjected to purification by flash chromatography (Biotage, 50% EtOAc/Hex) to afford the title compound.

Step D: 6-[(3R,9aS)-octahydropyrazino[2,1-c][1,4]oxazin-3-yl]-3,4-dihydro-1H-isochromen-1-one tert-Butyl(9aS)-3-hydroxy-3-(1-oxo-3,4-dihydro-1H-isochromen-6-yl)hexahydropyrazino[2,1-c][1,4]oxazine-8 (1H)-carboxylate (1.84 g, 4.55 mmol) was diluted with TFA (18 mL, 234 mmol) and cooled to 0° C. Some off gassing was apparent and after a few minutes a homogenous solution had been formed. Approximately 5 minutes post-TFA addition, $Et_3SiH$ (5.09 mL, 31.8 mmol) was added and the reaction mixture allowed to slowly warm to RT (allowed to warm naturally in the ice bath) where it was stirred for 18 h. The trans:cis diastereomeric ratio appeared to be ~95:5. The reaction vessel was transferred to a rotary evaporator and concentrated in vacuo to a two phase liquid. This crude material was diluted with CH₂Cl₂ washed with NaHCO₃,aq then water. The separately kept aqueous layers were subsequently extracted once with the same portion of CH₂Cl₂, the combined organics dried with MgSO₄, filtered and concentrated in vacuo. The crude residue was dried under house vacuum then the mixture was further purified by flash chromatography (2% MeOH 2% Et₃N in CH₂Cl₂) to afford the title compound.

INTERMEDIATE 40

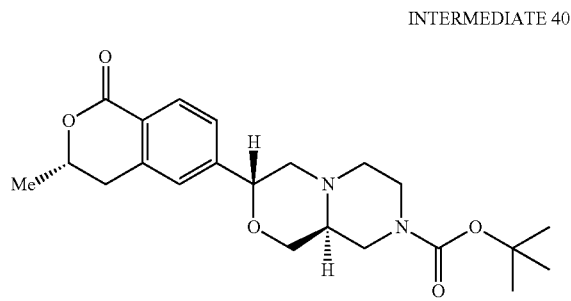 [SMILES: C[C@H]1Cc2cc([C@@H]3CN4CCN(C(=O)OC(C)(C)C)C[C@H]4CO3)ccc2C(=O)O1]

tert-Butyl (3R,9aS)-3-[(3S)-3-methyl-1-oxo-3,4-dihydro-1H-isochromen-6-yl]hexahydropyrazino[2,1-c][1,4]oxazine-8(1H)-carboxylate The title compound was prepared in a similar manner as 6-[(3R,9aS)-octahydropyrazino[2,1-c][1,4]oxazin-3-yl]-3,4-dihydro-1H-isochromen-1-one (Intermediate ?) except (3S)-6-Bromo-3-methyl-3,4-dihydro-1H-isochromen-1-one was used as the starting material in Step B. The cis/trans mixture was purified via chiral HPLC (30% 2:1 MeOH:MeCN/CO₂) on an AD column. The faster eluting diastereomer was the trans isomer. ¹H NMR (500 MHz; CDCl₃): 8.07 (d, J=8.1 Hz, 1H), 7.35 (d, J=8.0 Hz, 1H), 7.28 (s, 1H), 4.72 (dd, J=1.8, 10.5 Hz, 1H), 4.68 (m, 1H), 4.1-3.8 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.54 (d, J=6.2 Hz, 3H), 1.49 (s, 9H); LC-MS: (M+1)⁺ 403.

tert-butyl (3R,9aS)-3-(3-cyano-4-fluorophenyl)hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate Step A: 2-fluoro-5-(1-hydroxyethyl)benzonitrile 3-Cyano-4-fluorobenzaldehyde (2.17 g, 14.7 mmol) was dissolved in THF (50 mL) then cooled to −70° C. To this mixture was added methyl magnesiumbromide (5.34 mL, 16.0 mmol). The mixture was stirred for 1 h, then was quenched with brine and extracted with ether. The ethereal layer was separated, dried over Na₂SO₄, filtered, and evaporated to dryness. The residue was purified by MPLC chromatography through a 120 g Redi-sep column using 0-50% EtOAc/hexane eluent to yield 2-fluoro-5-(1-hydroxyethyl)benzonitrile: LC-MS: M+1=166.

Step B: 5-acetyl-2-fluorobenzonitrile

2-Fluoro-5-(1-hydroxyethyl)benzonitrile (0.80 g, 4.8 mmol) was dissolved in DCM (50 mL). To this mixture was added pyridinium dichromate (2.73 g, 7.27 mmol) and the mixture was stirred at RT overnight. Florisil (26 g) was added to the reaction mixture which was then diluted with 50 mL of ether and filtered through a pad of CELITE®. The filtrate was evaporated to dryness and the residue was purified by MPLC through a 120 g Redi-sep column, eluting with 0-100% EtOAc/hexane to yield 5-acetyl-2-fluorobenzonitrile.

Step C: 5-(bromoacetyl)-2-fluorobenzonitrile

5-Acetyl-2-fluorobenzonitrile (400 mg, 2.45 mmol) was dissolved in THF (20 mL) then copper (II) bromide (1.10 g, 4.90 mmol) was added and the mixture was stirred at RT for 48 h. The reaction mixture was diluted with 20 mL of ether then washed with water, followed by brine. The organic layer was separated, dried over Na₂SO₄, and filtered. The filtrate was evaporated to dryness then purified by MPLC INTERMEDIATES 41(isomer mixture), 41A and 41B

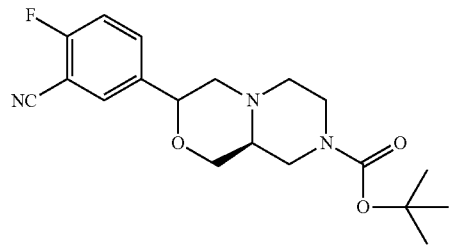

isomeric Mixture (Step F)

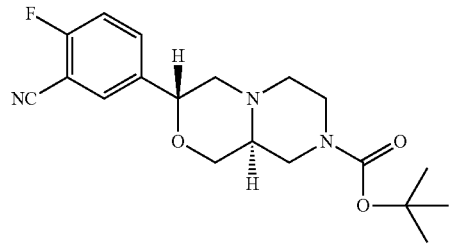

separated isomers (Step G)

chromatography through an 80 g Redi-sep column with 0-50% ethyl acetate/hexane eluent to yield 5-(bromoacetyl)-2-fluorobenzonitrile: LC-MS: M+1=244.

Step D: tert-butyl (3S)-4-[2-(3-cyano-4-fluorophenyl)-2-oxoethyl]-3-(hydroxymethyl)piperazine-1-carboxylate 5-(Bromoacetyl)-2-fluorobenzonitrile (590 mg, 2.44 mmol) and (S)-4-N-BOC-2-hydroxymethyl-piperazine (527 mg, 2.44 mmol) were dissolved in THF (40 mL) at 0° C. then TEA (247 mg, 2.44 mmol) was added. The reaction mixture was stirred at RT for 16 h, then poured into water and extracted with ethyl acetate. The organic layer was dried over $Na_2SO_4$, filtered, and evaporated to dryness. The crude product was purified by MPLC through an 80 g Redi-sep column using 0-100% EtOAc/hexane to yield the title compound.

Step E: tert-butyl (3S)-4-[2-(3-cyano-4-fluorophenyl)-2-hydroxyethyl]-3-(hydroxymethyl)piperazine-1-carboxylate tert-Butyl (3S)-4-[2-(3-cyano-4-fluorophenyl)-2-oxoethyl]-3-(hydroxymethyl)piperazine-1-carboxylate (800 mg, 2.12 mmol) was dissolved in ethanol (50 mL) then sodium borohydride (321 mg, 8.48 mmol) was added and the mixture was stirred at RT for 16 h. LC-MS analysis showed product to be present. The ethanol was removed and the residue was redissolved in EtOAc and stirred with 1N HCl for 5 min. The mixture was 10 then neutralized with saturated aqueous $NaHCO_3$ and extracted twice with EtOAc. The organic layers were washed with brine, dried over $Na_2SO_4$, filtered, and evaporated to dryness to yield the title compound. LC-MS: M+1=280.

Step F: tert-butyl (9aS)-3-(3-cyano-4-fluorophenyl)hexahydropyrazino[2,1-c][1,4]oxazine-8(1H)-carboxylate tert-Butyl (3S)-4-[2-(3-cyano-4-fluorophenyl)-2-hydroxyethyl]-3-(hydroxymethyl)piperazine-1-carboxylate (358 mg, 0.944 mmol) was dissolved in DCM (25 mL) and cooled to 0° C. To this mixture was added TEA (0.197 mL, 1.42 mmol) followed by methanesulfonyl chloride (0.096 mL, 1.2 mmol). The mixture was warmed to RT and stirred overnight. The reaction mixture was washed twice with brine, dried, and evaporated to dryness. The residue was purified by chromatography through a 40 g Redi-sep column, eluting with EtOAc/Hex 0-100% to yield the intermediate chloride (470 mg, 1.81 mmol). This chloride was then dissolved in THF (25 mL) and tetrabutylammonium chloride (436 mg, 1.18 mmol) was added at 0° C. followed by NaH (47.2 mg, 1.18 mmol) then the mixture was stirred at reflux overnight. The reaction mixture was diluted with EtOAc and washed with brine. The organic layer was dried over $Na_2SO_4$, filtered, and evaporated to dryness. The crude residue was purified by MPLC chromatography through a 40 g Redi-sep column, eluting with 0-100% ethyl acetate to yield the title compound as a mixture of two isomers: $^1$H-NMR (500 MHz, $CDCl_3$): δ ppm 7.86 (d, J=5.5 Hz, 0.5H), 7.75-7.81 (m, 0.5H), 7.65 (d, J=6 Hz, 1H), 7.58-7.61 (m, 0.5H), 7.19-7.24 (q, 1H), 4.79 (s, 0.5H), 4.66 d, J=10.5 Hz, 0.5H), 3.96 (dd, J=3, 11 Hz, 1H), 3.55-4.0 (b, 2H), 3.54 (dd, J=2.5, 11.5 Hz, 0.5H), 3.46 (t, J=10.5 Hz, 0.5H), 3.24 (t, J=8.5 Hz, 0.5 H), 3.18 (d, J=2.5 Hz, 0.5H) 3. (b, 2H), 2.89 (dd, J=2.1, 11.5 Hz, 0.5H), 2.7-2.8 (m, 2H), 2.5 (b, 1H), 2.38-2.45 (m, 1H), 2.25 (t, J=8.5 Hz, 1H), 2.17 (t, J=11 Hz, 1H), 1.48 (s, 9H); LC-MS: M+1=362.

Step G: tert-butyl (3R,9aS)-3-(3-cyano-4-fluorophenyl)hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate The title compounds were obtained by preparative HPLC separation of the mixture of isomers obtained in the prior step.

INTERMEDIATES 42A and 42B (Method 1)

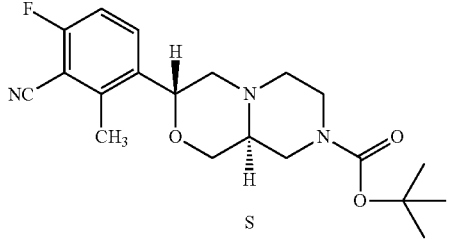

42A

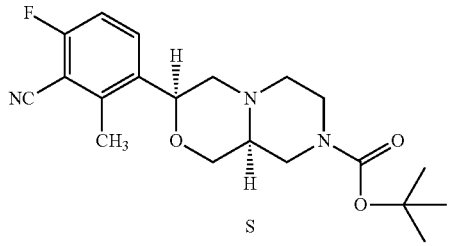

42B

42A: tert-butyl(3R,9aS)-3-(3-cyano-4-fluoro-2-methylphenyl)hexahydropyrazino[2,1-c][1,4]oxazine-8(1H)-carboxylate 42B: tert-butyl(3S,9aS)-3-(3-cyano-4-fluoro-2-methylphenyl)hexahydropyrazino[2,1-c][1,4]oxazine-8(1H)-carboxylate

Step A: 3-bromo-6-fluoro-2-methylbenzonitrile (Method A)

Commercially available 2-fluoro-6-methylbenzonitrile (Apollo Scientific, 15.0 g, 111 mmol) was dissolved in triflic acid (75 mL) at 0° C. then NBS (20.7 g, 117 mmol) was added. The reaction mixture was stirred at RT for 1 h then poured into ice water and extracted twice with DCM. The organic layer was washed with brine, dried over $Na_2SO_4$, then filtered and evaporated to dryness to yield 3-bromo-6-fluoro-2-methylbenzonitrile: LC-MS: M+1=216.

Alternate Step A (Method B):

To a 3 L 3 Neck RB equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By this time, HPLC shows the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over MgSO$_4$, concentrated, then stored in a −10° C. freezer overnight. Precipitate formed over this time, and was filtered and washed with 5% EtOAc/Hexanes. A second crop of precipitate was combined with the first crop to provide 3-bromo-6-fluoro-2-methyl-benzonitrile.

Step B: 3-ethenyl-6-fluoro-2-methylbenzonitrile

3-Bromo-6-fluoro-2-methylbenzonitrile (23.6 g, 110 mmol), potassium vinyl trifluoroborate (29.5 g, 221 mmol), PdCl$_2$(dppf)-CH$_2$Cl$_2$ Adduct (4.03 g, 5.51 mmol), and TEA (30.7 mL, 221 mmol) were added to 250 mL of ethanol. The reaction mixture was degassed then stirred at reflux for 4 h. LC-MS confirmed the presence of product. The reaction mixture was diluted with ethyl acetate, washed twice with brine, dried, and evaporated to dryness. The crude material was then purified by MPLC chromatography using a 330 g Redi-sep column and eluting with a 10% EtOAc/Hexane solvent system to yield 3-ethenyl-6-fluoro-2-methylbenzonitrile.

Step C: 6-fluoro-2-methyl-3-(oxiran-2-yl)benzonitrile

3-Ethenyl-6-fluoro-2-methylbenzonitrile (14.9 g, 92.0 mmol) was added to DCM (400 mL) at 0° C. then mCPBA (47.85 g, 277.5 mmol) was added and the mixture was stirred at RT for 72 h. The reaction mixture was washed with saturated aqueous Na$_2$S$_2$O$_3$, then with 1N NaOH, and brine. The organic layer was separated, dried over Na$_2$SO$_4$, filtered, and evaporated to dryness. The crude product was purified by chromatography through a 330 g Redi-sep column, eluting with 0-100% hexane/DCM solvent system to afford 6-fluoro-2-methyl-3-(oxiran-2-yl)benzonitrile. LC-MS: M+1=178.

Step D: tert-butyl (3S)-4-[2-(3-cyano-4-fluoro-2-methylphenyl)-2-hydroxyethyl]-3-(hydroxymethyl)piperazine-1-carboxylate 6-Fluoro-2-methyl-3-(oxiran-2-yl)benzonitrile (12.0 g, 67.7 mmol) and (S)-4-N-BOC-2-hydroxymethylpiperazine (22.0 g. 102 mmol) were suspended in ethanol (100 mL) then heated in a microwave apparatus for 30 minutes at 150° C. The reaction mixture was cooled and evaporated dryness. The residue was purified by MPLC chromatography through a 330 g Redi-sep column eluting with 5% MeOH/95% EtOAc solvent system to yield the title compound. LC-MS: M+1=394.

Step E: tert-butyl (9aS)-3-(3-cyano-4-fluoro-2-methylphenyl)hexahydropyrazino[2,1-c][1,4]oxazine-8(1H)-carboxylate tert-Butyl (3S)-4-[2-(3-cyano-4-fluoro-2-methylphenyl)-2-hydroxyethyl]-3-(hydroxymethyl)piperazine-1-carboxylate (18.5 g, 47.0 mmol) and cyanomethylenetri-n-butyl-phosphorane (20.4 g, 85.0 mmol) were dissolved in 180 mL of benzene. The reaction mixture was degassed and heated to 100° C. for 16 h. LC-MS analysis indicated product peak (M+1=376). The reaction was cooled and evaporated to dryness. The residue was purified by chromatography through a 330 g Redi-sep column, eluting with a 20% acetone/80% hexane mixture to yield a cis-trans mixture of the title compound.

Step F: tert-butyl(3R,9aS)-3-(3-cyano-4-fluoro-2-methylphenyl)hexahydropyrazino[2,1-c][1,4]ox-azine-8(1H)-carboxylate and tert-butyl(3S,9aS)-3-(3-cyano-4-fluoro-2-methylphenyl)hexahydropyrazino[2,1-c][1,4]oxazine-8(1H)-carboxylate The cis-trans isomers of the product of Step E were separated using a Chiralpak AD 4.6×250 mm 10 g column with 20% IPA/80% heptane solvent system: 42A (trans-isomer eluted first): $^1$H-NMR (500 MHz, CDCl$_3$): δ ppm 7.74 (dd, J=6, 8.5 Hz, 1H), 7.095 (t, J=8.5 Hz, 1H), 4.838 (d, J=10 Hz, 1H), 3.98 (dd, J=3, 11.5 Hz, 1H), 3.84-4.21 (b, 2H), 3.50 (t, J=11 Hz, 1H), 2.98-3.18 (b, 1H), 2.85 (dd, J=2, 11.5 Hz, 1H), 2.75 (d, J=10 Hz, 1H), 2.6 ppm (s, 3H), 2.45-2.68 (b, 1H), 2.24-2.31 (m, 2H), 2.16 (t, J=11 Hz, 1H), 1.50 ppm (s, 9H); LC-MS: M+1=376; 42B (cis-isomer eluted second): $^1$H-NMR (500 MHz, CDCl$_3$): δ ppm 8.20 (t, J=6.95 Hz, 1H), 7.06 (t, J=8.5 Hz, 1H), 4.91 (t, J=3.5 Hz, 1H), 3.70-4.07 (b, 2H), 3.55 (d, J=11 Hz, 1H), 3.26 (t, J=9 Hz, 1H), 3.15 (dd, J=3, 12 Hz, 1H), 2.98-3.11 (b, 1H), 2.82 (dd, J=4, 12 Hz, 2H), 2.63 (s, 3H), 2.59-2.7 (b, 1H), 2.44-2.49 (m, 2H), 1.50 (s, 9H); LC-MS: M+1=376.

Intermediate 42B

Method 2

Step A: 2-Fluoro-6-methyl-benzonitrile

A 10 L round bottom flask equipped with adapter, thermocouple and stir bar was charged with DMA (6 L) and degassed under vacuum and purged with N$_2$ three times. To the mixture was added Palladium Tetrakis triphenylphosphine (87.5 g, 72.0 mmol) and the mixture was degassed under vacuum and purged with N$_2$ three times. The reaction was heated to 80° C. for 30 min. 3-Fluoro-2-iodotoluene (575 g, 2.4 mol) and Zinc Cyanide (171.7 g, 1.46 mol) were added and the mixture was degassed under vacuum and purged with N$_2$ three times. The reaction mixture was heated to 80° C. for 16 h and then allowed to cool to RT. The solution was added to a 2.0 L aqueous solution of 1N NH$_4$OH and extracted three times with 1.5 L EtOAc. The extracts were washed with 2 L brine, dried over Na$_2$SO$_4$, filtered and concentrated. The crude product was treated with mCPBA in cooled DCM and then purified by chromatography (PE/EA=10:1) to get the title compound.

Step B: 3-Bromo-6-fluoro-2-methyl-benzonitrile

To a 3 L 3 Neck round bottomed flask equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By that time, HPLC showed the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over MgSO$_4$, concentrated, then stored in a −10° C. freezer overnight. Precipitate formed over this time, and was filtered and washed with 5% EtOAc/Hexanes, providing a first crop of product. A second crop of precipitate provided further 3-Bromo-6-fluoro-2-methyl-benzonitrile.

Step C: 3-(2-Bromo-acetyl)-6-fluoro-2-methyl-benzonitrile

Degassed tributyl(1-ethoxyvinyl)tin (200 mL, 591 mmol) was added to a stirred, room temperature mixture of 3-Bromo-6-fluoro-2-methyl-benzonitrile (115 g, 537 mmol) and cis-$PdCl_2(PPh_3)_2$ (18.9 g, 26.9 mmol) in degassed dioxane (1149 mL) and the mixture was stirred at 100° C. for 22 hours. By this time HPLC showed complete conversion of starting material (requires at least 12 hours), completion of the reaction can be seen by plating of palladium metal onto the side of the flask. At this time the reaction was cooled to 0° C. and THF (575 mL) and Water (230 mL) were added followed by NBS (110 g, 618 mmol) (added portionwise over 15 min, maintaining internal temperature <5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over $MgSO_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester Diisopropylethylamine (44.0 mL, 252 mmol) was added to a stirred, room temperature mixture of 72 wt % 3-(2-Bromo-acetyl)-6-fluoro-2-methyl-benzonitrile (69 g, 194 mmol) and (S)-4-N-Boc-2-hydroxymethyl-piperazine (42.0 g, 194 mmol) in THF (1000 mL) and the mixture was stirred at room temperature for 18 h. The reaction was diluted with 1 L EtOAc, washed 2× with 500 mL 10% w/w $NaHCO_3$ aqueous solution, dried over $MgSO_4$, filtered and concentrated. The residue was purified by column chromatography on silica gel (40-80% EtOAc/Hexanes, linear gradient), to give the title compound.

Step E: (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester Mesyl-Cl (17.2 mL, 221 mmol) was added dropwise to a stirred, <5° C. internal temperature mixture of (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (66.6 g, 170 mmol) and triethylamine (71.1 mL, 510 mmol) in $CH_2Cl_2$ (1000 mL) (exotherm occurs, so must keep addition slow), and the reaction was allowed to warm to room temperature for 30 minutes, by which time reaction was complete. The solution was washed with 500 mL 10% w/w $NaHCO_3$ aqueous solution. The organics were dried over $MgSO_4$, filtered and concentrated. The resulting material was taken up in a minimal amount of EtOAc (125 mL) with some heating (solution kept <50° C.) until all solids dissolved. The solution was allowed to cool with stirring, then dropwise overnight 350 mL hexanes was added. By the next morning the solution had clarified and there was considerable powder. The solids were collected by filtration and washed with 20% EtOAc/Hexanes, providing the title product. The mother liquors were concentrated until precipitate appeared, which was filtered to give additional title product.

Step F: (3S,9aS)-3-(3-Cyano-4-fluoro-2-methyl-phenyl)-hexahydro-pyrazino[2,1-c][1,4]oxazine-8-carboxylic acid tert-butyl ester To a 1 L 3 neck RB was charged 5% $Pd/CaCO_3$ (10.0 g., 4.02 mmol), MeOH (405 mL), and (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester (15.0 g., 40.2 mmol). The solution was sparged with $N_2$ for 5 min, then put under an atmosphere of hydrogen with balloon pressure and warmed to 40° C. with stirring. After 38 h, HPLC shows full conversion of the olefin, with a 5:1 cis:trans ratio of diastereomers. The suspension was cooled to room temperature, filtered through a pad of CELITE® and concentrated. The residue was purified via column chromatography (60-100% EtOAc/Hexanes, linear gradient), to provide the title compound. $^1$H NMR (400 MHz, $CDCl_3$): δ 8.18 (m, 1H), 7.03 (t, J=7.9 Hz, 1H), 4.87 (s, 1H), 4.10-3.60 (m, 2H), 3.56 (d, J=10.5 Hz, 1H), 3.25-2.88 (m, 3H), 2.80-2.35 (m, 8H), 1.50 (s, 9H).

Intermediate 42A

Method 2

A three-necked, round-bottomed flask equipped with a nitrogen inlet adapter, thermocouple, and a septum was charged with (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (330 g, 840 mmol), TFA (1.65 L, 21 mol), and 3300 mL of DCM. $Et_3SiH$ (292 g, 2.52 mol, 3 equiv) was added in one portion and the reaction mixture stirred at room temperature for 24 h. The reaction mixture was concentrated and azeotroped with toluene (100 mL) to remove the TFA. The resulting material was dissolved in DCM (1.7 L) and carefully charged with 2.5 M $Na_2CO_3$ (pH should be basic). $Boc_2O$ (218 g, 1.2 equiv) was added in one portion and the reaction mixture was stirred at room temperature for 2 h. The organic layer was separated, concentrated, and purified via column chromatography (0-30% acetone-hexanes) to give a mixture of product cis/trans isomers. Chiral SFC purification (Berger Multi-Gram™ SFC, Mettler Toledo Co, Ltd, AD 250 mm×50 mm, 5 um column, A: supercritical $CO_2$, B: methanol, A:B=85:15 at 150 mL/min) afforded the major trans diastereomer 42A as well as the cis diastereomer 42B.

INTERMEDIATES 42C and 42D (Method 1)

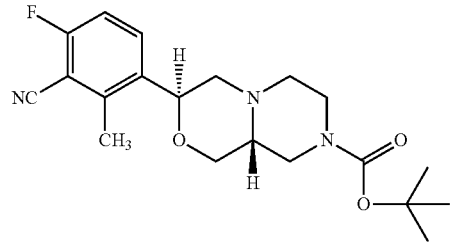

42C

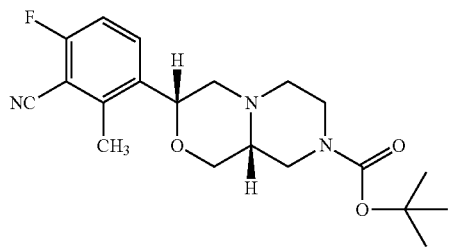

42C: tert-butyl(3S,9aR)-3-(3-cyano-4-fluoro-2-methylphenyl)hexahydropyrazino[2,1-c][1,4]oxazine-8(1H)-carboxylate 42D: tert-butyl(3R,9aR)-3-(3-cyano-4-fluoro-2-methylphenyl)hexahydropyrazino[2,1-c][1,4]oxazine-8(1H)-carboxylate Step A: tert-butyl (3R)-4-[2-(3-cyano-4-fluoro-2-methylphenyl)-2-hydroxyethyl]-3-(hydroxymethyl)piperazine-1-carboxylate 6-Fluoro-2-methyl-3-(oxiran-2-yl)benzonitrile (prepared as described above for I-42A and I-42B, Method 1, Steps A-C) (4.80 g, 27.1 mmol) and (R)-4-N-BOC-2-hydroxymethyl-piperazine (8.79 g. 40.6 mmol) were suspended in EtOH (30 mL) and heated in a microwave apparatus at 150° C. for 1 h. The reaction mixture was cooled and evaporated to dryness. The residue was purified by chromatography through a 330 g ISCO Redi-sep column eluting with ethyl acetate to 5% MeOH/ethyl acetate to yield the title compound. LC-MS: M+1=394;

Step B: tert-butyl(3S,9aR)-3-(3-cyano-4-fluoro-2-methylphenyl)hexahydropyrazino[2,1-c][1,4]oxazine-8(1H)-carboxylate and tert-butyl(3R,9aR)-3-(3-cyano-4-fluoro-2-methylphenyl)hexahydropyrazino[2,1-c][1,4]oxazine-8(1H)-carboxylate tert-Butyl (3R)-4-[2-(3-cyano-4-fluoro-2-methylphenyl)-2-hydroxylethyl]-3-(hydroxymethyl)piperazine-1-carboxylate (7.14 g, 18.2 mmol) and cyanomethylene tributylphosphorane (7.88 g, 32.7 mmol) were dissolved in benzene (60.0 mL) then heated at 100° C. overnight. The reaction mixture was cooled and evaporated to dryness. The residue was purified by chromatography through a 330 g ISCO Redi-sep column eluting with 10% acetone/DCM to 20% acetone DCM gradient to yield trans-cis mixture. The isomers were resolved by chiral HPLC (70 mL/min of 15% 2:1 MeOH:MeCN:$CO_2$ on a 30×250 mm Chiralpak IC column (Diacel Chemical Industries, LTD.) at 100 bar and 35° C., 230 nM). Isomer 42C (faster eluting): $^1$H-NMR (500 MHz, $CDCl_3$): δ ppm 7.73 (dd, J=9.0, 6.0 Hz, 1H), 7.09 (t, J=8.4 Hz, 1H), 4.83 (d, J=9.3 Hz, 1 Hz, 1H), 4.05 (b, 2H), 3.98 (dd, J=11.25, 2.7, 1H), 3.49 (t, J=10.5 Hz, 1H), 3.031 (b, 1H), 2.84 (d, J=11, 6 Hz, 1H), 2.74 (d, J=11.5 Hz, 1H), 2.59 (s, 3H), 2.54 (b, 1H), 2.22-2.30 (m, 2H), 2.146 (t, J=11.0 Hz, 1H), 1.5 (s, 9H): Isomer 42D (slower eluting): $^1$H-NMR (500 MHz, $CDCl_3$): δ ppm 8.19 (b, 1H), 7.05 (t, J=8.5 Hz, 1H), 4.90 (s, 1H), 3.98 (b, 3H), 3.54 (d, J=12.5 Hz, 1H), 3.24 (b, 1H), 3.14 (dd, J=12, 2.5 Hz, 1H), 3.05 (b, 1H), 2.80 (dd, J=11.25, 2.5 Hz, 2H), 2.68 (b, 1H), 2.63 (s, 3H), 2.46 (b, 1H), 1.5 (s, 9H).

Intermediate 42C and 42D

Method 2

Step A: 2-Fluoro-6-methyl-benzonitrile

A 10 L round bottom flask equipped with adapter, 10 thermocouple and stir bar was charged with DMA (6 L) and degassed under vacuum and purged with $N_2$ three times. To the mixture was added palladium tetrakis triphenylphosphine (87.5 g, 72.0 mmol) and the mixture was degassed under vacuum and purged with $N_2$ three times. The reaction was heated to 80° C. for 30 min. 3-Fluoro-2-iodotoluene (575 g, 2.4 mol) and zinc cyanide (171.7 g, 1.46 mol) were added and the mixture was degassed under vacuum and purged with $N_2$ three times. The reaction mixture was heated to 80° C. for 16 h and then allowed to cool to RT. The solution was added to a 2.0 L aqueous solution of 1N $NH_4OH$, which was extracted three times with 1.5 L EtOAc, washed with 2 L brine, dried over $Na_2SO_4$, filtered and concentrated. The crude product was treated with mCPBA in cooled DCM and then purified by chromatography (PE/EA=10:1) to get the title compound.

Step B: 3-Bromo-6-fluoro-2-methyl-benzonitrile

To a 3 L 3 Neck round bottomed flask equipped with overhead stirrer was charged 2-fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. The reaction was poured into 1 L of ice, diluted with 700 mL 30% EtOAc/Hexanes, and agitated. The aqueous layer was cut, and the organics washed 2× with 1N NaOH and with water. The organics were dried over $MgSO_4$, concentrated, then stored in a −10° C. freezer overnight. Precipitate formed over this time, and was filtered and washed with 5% EtOAc/Hexanes, providing a first crop of product. A second crop of precipitate provided additional 3-Bromo-6-fluoro-2-methyl-benzonitrile.

Step C: 3-(2-Bromo-acetyl)-6-fluoro-2-methyl-benzonitrile

Degassed tributyl(1-ethoxyvinyl)tin (200 mL, 591 mmol) was added to a stirred, room temperature mixture of 3-bromo-6-fluoro-2-methyl-benzonitrile (115 g, 537 mmol) and cis-$PdCl_2(PPh_3)_2$ (18.9 g, 26.9 mmol) in degassed dioxane (1149 mL) and the mixture was stirred at 100° C. for 22 hours. Completion of the reaction could be seen by plating of palladium metal onto the side of the flask. The reaction was cooled to 0° C. and THF (575 mL) and Water (230 mL) were added followed by NBS (110 g, 618 mmol) (added portionwise over 15 min, maintaining internal temperature <5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over $MgSO_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3S,9aR)-3-(3-Cyano-4-fluoro-2-methyl-phenyl)-3-hydroxy-hexahydro-pyrazino[2,1-c][1,4]oxazine-8-carboxylic acid tert-butyl ester Diisopropylethylamine (156 mL, 894 mmol) was added to a stirred, room temperature mixture of 3-(2-Bromo-acetyl)-6-fluoro-2-methyl-benzonitrile (176 g, 688 mmol) and (R)-4-N-Boc-2-hydroxymethyl-piperazine (149 g, 688 mmol) in THF (3500 mL) and the mixture was stirred at room temperature for 18 h. The reaction was diluted with 3 L EtOAc, washed 2× with 1500 mL 10% w/w NaHCO$_3$ aqueous solution, dried over MgSO$_4$, filtered and concentrated. The residue was purified by column chromatography on silica gel (40-80% EtOAc/Hexanes, linear gradient), to provide the title compound.

Step E: 42C and 42D

A 5000-mL, three-necked, round-bottomed flask equipped with a nitrogen inlet adapter, thermocouple, and a septum was charged with the product of Step D (273 g, 696.2 mmol), TFA (1340 mL, 17.45 mol, 25 equiv), and 1300 mL of DCM. Et$_3$SiH (333 mL, 2.1 mol, 3 equiv) was added in one portion and the reaction mixture was stirred at room temperature for 12 h. The reaction mixture was concentrated to remove the TFA. The resulting material was dissolved in DCM (600 mL) and carefully charged with 2.5 M Na$_2$CO$_3$ (1400 mL, 3.5 mol, 5 equiv) (pH should be basic). Boc$_{20}$ (243 mL, 1.05 mol, 1.5 equiv) was added in one portion and the reaction mixture was stirred at room temperature for 2 h. The organic layer was separated, concentrated, and purified via column chromatography (0-30% acetone-hexanes) to give the product (ca. 2:1 trans: cis), which was separated by Chiral SFC to give both single isomers: Chrial SFC HPLC separation conditions: Instrument: Berger MultiGram SFC, Mettler Toledo Co, Ltd.; Column: Chiralpak AD column (Diacel Chemical Industries, LTD.) 250 mm×50 mm, 5 um.; Mobile phase: A: Supercritical CO$_2$, B: MeOH, A:B=85:15 at 150 mL/min.; Column Temp: 38° C.; Nozzle Pressure: 100 Bar; Nozzle Temp: 60° C.; Evaporator Temp: 20° C.; Trimmer Temp: 25° C.; Wavelength: 235 nm. 42C trans isomer $^1$H NMR 400 MHz, CDCl$_3$ δ: 7.720-7.683 (dd, J=9.6 Hz, 1H), 7.056 (t, J=8 Hz, 1H), 4.811-4.787 (d, J=9 Hz, 1H), 3.962-3.928 (dd, J=9.6 Hz, 3H), 3.465 (t, J=10 Hz 1H), 3.002 (s, 1H), 2.826-2.797 (d, J=11 Hz, 1H), 2.719 (s, 1H), 2.638-2.559 (m, 4H), 2.091-2.253 (m, 3H), 1.469 (s, 9H); 42D cis isomer $^1$H NMR 400 MHz, CDCl$_3$ δ: 8.182-8.146 (t, J=7 Hz, 1H), 7.019 (t, J=9 Hz, 1H), 4.873 (s, 1H), 3.952-3.711 (m, 2H), 3.530-3.503 (d, J=11 Hz, 1H), 3.215-3.020 (m, 3H), 2.801-2.761 (d, J=16 Hz, 1H), 2.593 (s, 4H), 2.452-2.430 (m, 3H), 1.463 (s, 9H).

INTERMEDIATE 43A

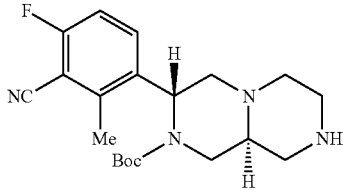

(3R,9aS)-tert-butyl 3-(3-cyano-4-fluoro-2-methylphenyl)hexahydro-1H-pyrazino[1,2-a]pyrazine-2(6H)-carboxylate

Step A: (3S)-tert-butyl 4-(2-(3-cyano-4-fluoro-2-methylphenyl)-2-hydroxyethyl)-3-(hydroxymethyl)piperazine-1-carboxylate A mixture of 6-fluoro-2-methyl-3-(oxiran-2-yl)benzonitrile (785 mg, 4.43 mmol) and (S)-tert-butyl 3-(hydroxymethyl)piperazine-1-carboxylate (1340 mg, 6.2 mmol) in ethanol (10 mL) was heated in microwave at 150° C. for 3 h. The volatile was evaporated and the residue was purified on Biotage using 40-100% ethyl acetate/hexane to give the title compound: LC/MS: (M+1)$^+$: 394.19.

Step B: (3S)-benzyl 4-(2-(3-cyano-4-fluoro-2-methylphenyl)-2-hydroxyethyl)-3-(hydroxymethyl)piperazine-1-carboxylate To a solution of (3S)-tert-butyl 4-(2-(3-cyano-4-fluoro-2-methylphenyl)-2-hydroxyethyl)-3-(hydroxymethyl)piperazine-1-carboxylate (2.87 g, 7.32 mmol) in methylene chloride (20 mL) was added trifluoroacetic acid (20 mL) at rt, and the resulting solution was stirred at rt for 1 h. After removing the volatile solvents, the residue was dissolved in methylene chloride (50 mL). To the above solution was added triethylamine (6.12 mL, 43.9 mmol) and benzyl chloroformate (1.1 mL, 7.3 mmol) dropwise at 0° C. The reaction solution was stirred at 0° C. for 1 h before quenching with saturated sodium bicarbonate solution (200 mL). The mixture was then extracted with methylene chloride (3×100 mL). The combined organic phase was dried over sodium sulphate and concentrated to give the title compound. LC/MS: (M+1)$^+$:428.18.

Step C: (7R,9aR)-benzyl 8-allyl-7-(3-cyano-4-fluoro-2-methylphenyl)hexahydro-1H-pyrazino[1,2-a]pyrazine-2(6H)-carboxylate and (7S,9aR)-benzyl 8-allyl-7-(3-cyano-4-fluoro-2-methylphenyl)hexahydro-1H-pyrazino[1,2-a]pyrazine-2(6H)-carboxylate A solution of (3S)-benzyl 4-(2-(3-cyano-4-fluoro-2-methylphenyl)-2-hydroxyethyl)-3-(hydroxymethyl)piperazine-1-carboxylate (1.68 g, 3.93 mmol) in sulfonyl chloride (14.0 g, 118 mmol) was heated at 90° C. for 1 h. After removing the volatile, the residue was dissolved in DMF (16 mL), treated with allylamine (1.726 mL, 23.58 mmol) and sodium iodide (0.059 g, 0.39 mmol) in a sealed tube at 0° C. and the resulting mixture was heated at 90° C. for 1 h. The mixture was diluted in ethyl acetate (300 mL), was washed with saturated sodium bicarbonate (3×200 mL), dried over sodium sulphate, concentrated, and the residue was purified on Biotage using 40-80% ethyl acetate/hexane to give the title compound (more polar on TLC). LC/MS: (M+1)$^+$: 449.24.

Step D: (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate A mixture of (7R,9aR)-benzyl 8-allyl-7-(3-cyano-4-fluoro-2-methylphenyl)hexahydro-1H-pyrazino[1,2-a]pyrazine-2(6H)-carboxylate (1260 mg, 2.81 mmol), 1,3-dimethylpyrimidine-2,4,6(1H,3H,5H)-trione (1316 mg, 8.430 mmol) and tetrakis(triphenylphosphine)palladium(0) (162 mg, 0.140 mmol) in methylene chloride (10 mL) was heated at 35° C. for 4 h. After cooling to rt, di-tert-butyl dicarbonate (736 mg, 3.37 mmol) and triethylamine (1579 µL, 11.24 mmol) were added and the resulting solution was stirred at rt overnight. After concentration, the residue was purified on Biotage using 40% EtOAc/hexane to give the title compound. LC/MS: (M+1)$^+$: 509.32.

Step E: (3R,9aS)-tert-butyl 3-(3-cyano-4-fluoro-2-methylphenyl)hexahydro-1H-pyrazino[1,2-a]pyrazine-2(6H)-carboxylate To a solution of (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate (600 mg, 1.180 mmol) in MeOH (100 mL) was added palladium on carbon (10%, 126 mg, 0.118 mmol) and the resulting mixture was subjected to hydrogenation at rt overnight. The reaction mixture was filtered through CELITE®, washed with mixture of methanol and methylene chloride (1:1) and the filtrate was concentrated to give the title compound: LC/MS: (M+1)$^+$: 375.28.

INTERMEDIATE 43B

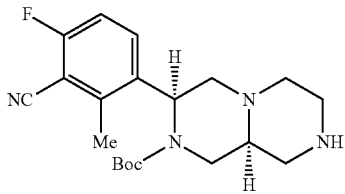

(3S,9aS)-tert-butyl 3-(3-cyano-4-fluoro-2-methylphenyl)hexahydro-1H-pyrazino[1,2-a]pyrazine-2(6H)-carboxylate Step A: (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate A mixture of (7S,9aR)-benzyl 8-allyl-7-(3-cyano-4-fluoro-2-methylphenyl)hexahydro-1H-pyrazino[1,2-a]pyrazine-2(6H)-carboxylate (518 mg, 1.155 mmol), 1,3-dimethylpyrimidine-2,4,6(1H,3H,5H)-trione_(518 mg, 1.16 mmol) and tetrakis(triphenylphosphine)palladium(0) (66.7 mg, 0.058 mmol) in methylene chloride (10 mL) was heated at 35° C. for 4 h. After cooling to rt, di-tert-butyl dicarbonate (302 mg, 1.39 mmol) and triethylamine (649 µL, 4.62 mmol) was added and the resulting solution was stirred at rt overnight. After concentration, the residue was purified on Biotage using 40% EtOAc/hexane to give the title compound: LC/MS: (M+1)$^+$: 509.26.

Step B: (3S,9aS)-tert-butyl 3-(3-cyano-4-fluoro-2-methylphenyl)hexahydro-1H-pyrazino[1,2-a]pyrazine-2(6H)-carboxylate To a solution of (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate (0.78 g, 1.534 mmol) in MeOH (100 mL) was added palladium on carbon (10%, 0.163 g, 0.153 mmol) and the resulting mixture was subjected to hydrogenation at rt overnight. The reaction mixture was filtered through CELITE®, washed with mixture of methanol and methylene chloride (1:1) and the filtrate was concentrated to give the title compound: LC/MS: (M+1)$^+$: 375.28.

INTERMEDIATE 43C

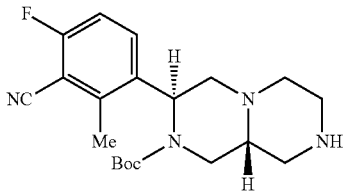

(3S,9aR)-tert-butyl 3-(3-cyano-4-fluoro-2-methylphenyl)hexahydro-1H-pyrazino[1,2-a]pyrazine-2(6H)-carboxylate The title compound was prepared in an analogous fashion to that described for the synthesis of (3R,9aS)-tert-butyl 3-(3-cyano-4-fluoro-2-methylphenyl)hexahydro-1H-pyrazino[1,2-a]pyrazine-2(6H)-carboxylate starting from 6-fluoro-2-methyl-3-(oxiran-2-yl)benzonitrile and (R)-tert-butyl 3-(hydroxymethyl)piperazine-1-carboxylate. LC/MS: 375.16 (M+1)+.

INTERMEDIATE 43D

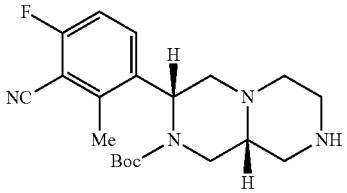

(3R,9aR)-tert-butyl 3-(3-cyano-4-fluoro-2-methylphenyl)hexahydro-1H-pyrazino[1,2-a]pyrazine-2(6H)-carboxylate The title compound was prepared in an analogous fashion to that described for the synthesis of (3S,9aS)-tert-butyl 3-(3-cyano-4-fluoro-2-methylphenyl)hexahydro-1H-pyrazino[1,2-a]pyrazine-2(6H)-carboxylate starting from (7R,9aS)-benzyl 8-allyl-7-(3-cyano-4-fluoro-2-methylphenyl)hexahydro-1H-pyrazino[1,2-a]pyrazine-2(6H)-carboxylate (obtained from the synthesis of (3S,9aR)-tert-butyl 3-(3-cyano-4-fluoro-2-methylphenyl)hexahydro-1H-pyrazino[1,2-a]pyrazine-2(6H)-carboxylate). LC/MS: 375.14 (M+1)+.

INTERMEDIATES 44A and 44B

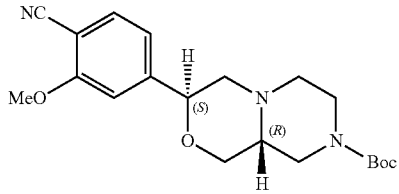

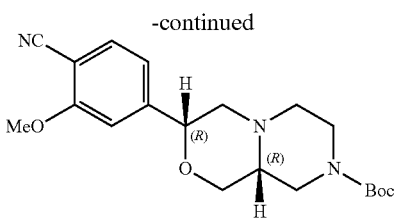

44A: tert-Butyl (3S,9aR)-3-(4-cyano-3-methoxyphenyl)hexahydropyrazino[2,1-c][1,4]oxazine-8(1H)-carboxylate and 44B: tert-Butyl (3R,9aR)-3-(4-cyano-3-methoxyphenyl)hexahydropyrazino[2,1-c][1,4]oxazine-8(1H)-carboxylate Step A: tert-Butyl (3R)-4-[2-(4-cyano-3-methoxyphenyl)-2-hydroxyethyl]-3 (hydroxymethyl) piperazine1-carboxylate A Pyrex vessel was charged with magnetic stirring bar, (2.0 g, 11.42 mmol) of 2-methoxy-4-(oxiran-2-yl)benzonitrile, (3.70 g, 17.12 mmol) of tert-butyl (3R)-3-(hydroxymethyl)piperazine-1-carboxylate, and 6 mL of EtOH. Then it was introduced in the microwave reactor and irradiated at 150° C. for 3 h. The mixture was cooled to room temperature and the solvent was evaporated and the resulting residue was purified by column chromatography (silica gel, 1-20% dichloromethane/MeOH) which afforded the product as a mixture of two diastereomers (1:1) LC/MS: (IE, m/z) [(M+1)-t-Bu]⁺=336.41

Step B: tert-Butyl (9aR)-3-(4-cyano-3-methoxyphenyl)hexahydropyrazino[2,1-c][1,4]oxazine-8(1H)-carboxylate The isomeric mixture of the prior step (3.48 g, 8.89 mmol, 1:1) in benzene was treated with (tributyl-$\lambda^5$-phosphanylidene) acetonitrile (3.22 g, 13.3 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1→3:7, as eluent) to give an isomeric mixture of the bicyclic title compound.

Step C: tert-Butyl(3S,9aR)-3-(4-cyano-3-methoxyphenyl)hexahydropyrazino[2,1-c][1,4]oxazine-8(1H)-carboxylate and tert-Butyl(3R,9aR)-3-(4-cyano-3-methoxyphenyl)hexahydropyrazino[2,1-c][1,4]oxazine-8(1H)-carboxylate The isomeric mixture was further separated into its enantiomers using a 21×250 mm ChiralCel OJ-H, column, eluting with 15% MeOH/CO₂ with a flow rate of 50 mL/min, 100 bar, 59 mg/mL in MeOH, 35C, 220 nm, Thr=200: trans-¹H NMR (CDCl₃, (trans) isomer, 500 MHz) δ 7.54 (d, J=7.9 Hz, 1H), 7.05 (s, 1H), 6.97 (d, J=7.9 Hz, 1H), 4.72 (d, J=8.9 Hz, 1H), 4.12-4.0 (m, 2H), 3.98 (s, 3H), 3.49 (t, J=9.4 Hz, J=9.0 Hz, 1H), 3.03 (bs, 1H), 2.94 (d, J=11.2 Hz, 1H), 2.76 (d, J=9 Hz, 1H), 2.56 (bs, 1H), 2.29-2.192 (m, 3H), 1.69 (bs, 1H), 1.50 (s, 9H); LC/MS: (IE, m/z) [(M+1)-t-Bu]⁺=318.40; cis-¹H NMR (CDCl₃, (cis) isomer, 500 MHz) δ 7.58 (d, J=7.9 Hz, 1H), 7.21 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (d, J=11.6 Hz, 1H), 3.05 (bs, 1H), 2.81 (bs, 2H), 2.72-2.42 (m, 3H), 1.50 (s, 9H); LC/MS: (IE, m/z) [(M+1)-t-Bu]⁺=318.35.

INTERMEDIATES 44C and 44D

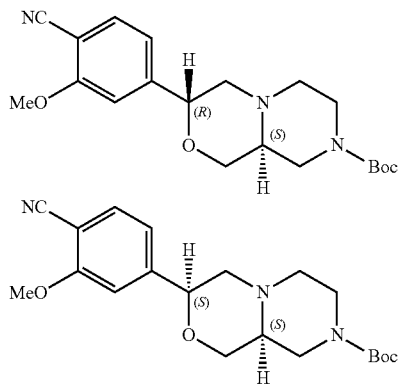

44C: tert-Butyl (3R,9aS)-3-(4-cyano-3-methoxyphenyl)hexahydropyrazino[2,1-c][1,4]oxazine-8(1H)-carboxylate and 44D: tert-Butyl (3S,9aS)-3-(4-cyano-3-methoxyphenyl)hexahydropyrazino[2,1-c][1,4]oxazine-8(1H)-carboxylate Step A: tert-Butyl (3S)-4-[2-(4-cyano-3-methoxyphenyl)-2-hydroxyethyl]-3-(hydroxymethyl)piperazine-1-carboxylate A Pyrex vessel was charged with magnetic stirring bar, (0.350 g, 2.00 mmol) of 2-methoxy-4-(oxiran-2-yl)benzonitrile, (0.457 g, 2.20 mmol) of tert-butyl (3S)-3-(hydroxymethyl)piperazine-1-carboxylate, and 6 mL of EtOH. Then it was introduced in the microwave reactor and irradiated at 150° C. for 3 hr. Then the mixture was cooled to room temperature and the solvent was evaporated and the resulting residue was purified by column chromatography (silica gel, 1-20% dichloromethane/MeOH) which afforded the title compound as a mixture of two diastereomers (1:1). LC/MS: (IE, m/z) [(M+1)-t-Bu]⁺=336.1.

Step B: tert-Butyl (9aS)-3-(4-cyano-3-methoxyphenyl)hexahydropyrazino[2,1-c][1,4]oxazine-8(1H)-carboxylate The isomeric mixture of the prior step (0.55 g, 1.40 mmol, 1:1) in benzene was treated with (tributyl-$\lambda^5$-phosphanylidene) acetonitrile (0.678 g, 2.81 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1-3:7, as eluent) to give an isomeric mixture of the bicyclic title compound. LC/MS: (IE, m/z) [(M+1)-t-Bu]⁺=318.06.

Step C: 44C: and 44D tert-Butyl (9aS)-3-(4-cyano-3-methoxyphenyl)hexahydropyrazino[2,1-c][1,4]oxazine-8(1H)-carboxylate was further separated into its enantiomers using a 21×250 mm ChiralCel OJ-H, column, eluting with 15% MeOH/CO₂ with a flow rate of 50 mL/min, 100 bar, 59 mg/mL in MeOH, 35C, 220 nm, Thr=200: trans-¹H NMR (CDCl₃, (trans)

isomer, 500 MHz) δ 7.55 (d, J=8.0 Hz, 1H), 7.06 (s, 1H), 6.97 (d, J=8.0 Hz, 1H), 4.71 (d, J=9.4 Hz, 1H), 4.12-4.0 (m, 2H), 3.98 (s, 3H), 3.48 (t, J=9.4 Hz, J=10.3 Hz, 1H), 3.03 (bs, 1H), 2.94 (d, J=11.0 Hz, 1H), 2.76 (d, J=7.8 Hz, 1H), 2.54 (bs, 1H), 2.29-2.192 (m, 3H), 1.51 (s, 9H); LC/MS: (IE, m/z) [(M+1)-t-Bu]⁺=318.17; cis-¹H NMR (CDCl₃, (cis) isomer, 500 MHz) δ 7.58 (d, J=8.0 Hz, 1H), 7.22 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (dd, J=3.6 Hz, J=3.7 Hz, 1H), 3.01 (bs, 1H), 2.80 (bs, 2H), 2.72-2.42 (m, 3H), 1.50 (s, 9H); LC/MS: (IE, m/z) [(M+1)-t-Bu]⁺=318.35.

INTERMEDIATES 45A and 45B

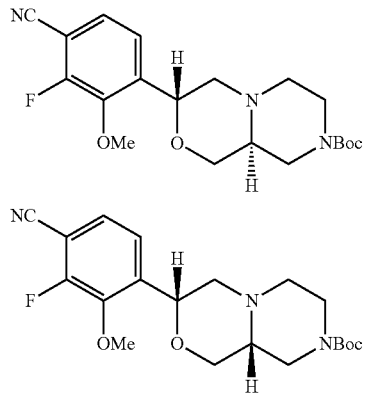

tert-butyl (3R,9aS)-3-(4-cyano-3-fluoro-2-methoxyphenyl)hexahydropyrazino[2,1-c][1,4]oxazine-8(1H)-carboxylate and tert-butyl (3R,9aR)-3-(4-cyano-3-fluoro-2-methoxyphenyl)hexahydropyrazino[2,1-c][1,4]oxazine-8(1H)-carboxylate The title compound was prepared in an analogous fashion to that described for the synthesis of tert-Butyl (3R,9aS)-3-(4-cyano-3-methoxyphenyl)hexahydropyrazino[2,1-c][1,4]oxazine-8(1H)-carboxylate except starting from 2-fluoro-3-methoxy-4-(oxiran-2-yl)benzonitrile. Trans and cis isomers were separated by prep SFC with 15% (2:1 MeOH:MeCN)/ $CO_2$ on OD column. Trans isomer eluted first; ¹H NMR (500 MHz, CDCl₃) δ 7.29-7.16 (m, 2H), 4.83 (dd, J=10.1, 1.7 Hz, 1H), 3.92-3.82 (m, 6H), 3.33 (t, J=10.7 Hz, 1H), 2.90-2.80 (m, 2H), 2.60 (d, J=10.6 Hz, 1H), 2.40 (br s, 1H), 2.16-2.04 (m, 2H), 1.90 (t, J=10.8 Hz, 1H), 1.32 (s, 9H).

INTERMEDIATE 46

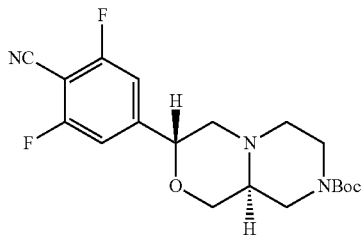

tert-butyl (3R,9aS)-3-(4-cyano-3,5-difluorophenyl)hexahydropyrazino[2,1-c][1,4]oxazine-8(1H)-carboxylate The title compound was prepared in an analogous fashion to that described for the synthesis of tert-Butyl (3R,9aS)-3-(4-cyano-3-methoxyphenyl)hexahydropyrazino[2,1-c][1,4]oxazine-8(1H)-carboxylate except starting from 2,6-difluoro-4-(oxiran-2-yl)benzonitrile. Trans and cis isomers were separated by prep SFC with 15% (2:1 MeOH:MeCN)/ $CO_2$ on IA column; ¹H NMR (500 MHz, CDCl₃) δ 7.08 (d, J=8.4 Hz, 2H), 4.69 (dd, J=10.4, 2.1 Hz, 1H), 4.12-3.92 (m, 3H), 3.46 (t, J=10.8 Hz, 1H), 3.00-2.87 (m, 2H), 2.72 (d, J=11.1 Hz, 1H), 2.48 (br s, 1H), 2.25-2.20 (m, 2H), 2.14 (t, J=11.0 Hz, 1H), 1.49 (s, 9H).

INTERMEDIATE 47A

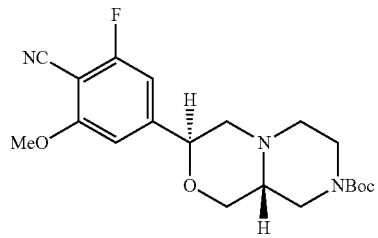

tert-butyl (3S,9aR)-3-(4-cyano-3-fluoro-5-methoxyphenyl)hexahydropyrazino[2,1-c][1,4]oxazine-8 (1H)-carboxylate The title compound was prepared in an analogous fashion to 15 that described for the synthesis of tert-Butyl (3S,9aR)-3-(4-cyano-3-methoxyphenyl)hexahydropyrazino[2,1-c][1,4]oxazine-8(1H)-carboxylate except starting from 2-fluoro-6-methoxy-4-(oxiran-2-yl)benzonitrile and tert-butyl (3R)-3-(hydroxymethyl)piperazine-1-carboxylate. Trans and cis isomers were separated by prep SFC with 15% (2:1 MeOH: MeCN)/CO₂ on IA column; ¹H NMR (500 MHz, CDCl₃) δ 6.80 (s, 1H), 6.75 (d, J=9.1 Hz, 1H), 4.65 (dd, J=10.4, 2.1 Hz, 1H), 4.12-3.92 (m, 6H), 3.43 (t, J=10.6 Hz, 1H), 3.02-2.87 (m, 2H), 2.73 (d, J=11.0 Hz, 1H), 2.50 (br s, 1H), 2.28-2.18 (m, 2H), 2.15 (t, J=11.0 Hz, 1H), 1.47 (s, 9H).

INTERMEDIATES 48A and 48B

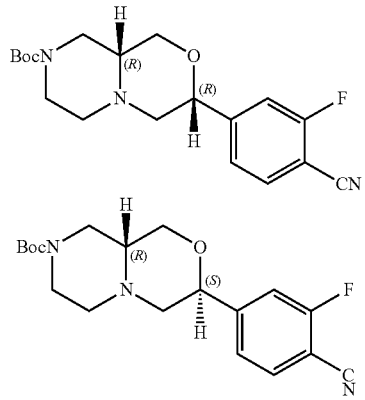

48B: tert-butyl (3S,9aR)-3-(4-cyano-3-fluorophenyl)hexahydropyrazino[2,1-c][1,4]oxazine-8(1H)-carboxylate and 48A: tert-butyl (3R,9aR)-3-(4-cyano-3-fluorophenyl)hexahydropyrazino[2,1-c][1,4]oxazine-8 (1H)-carboxylate The title compounds were prepared in an analogous fashion to that described for the synthesis of tert-Butyl (3S,9aR)-3-(4-cyano-3-methoxyphenyl)hexahydropyrazino[2,1-c][1,4]oxazine-8(1H)-carboxylate except starting from 2-fluoro-4-oxiran-2-ylbenzonitrile and tert-butyl (3R)-3-(hydroxymethyl)piperazine-1-carboxylate. Trans and cis isomers were separated by prep SFC.

INTERMEDIATE 49B

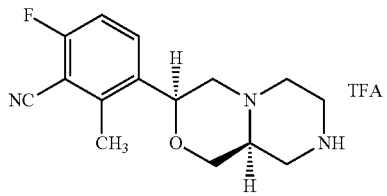

6-fluoro-2-methyl-3-[(3S,9aS)-octahydropyrazino[2,1-c][1,4]oxazin-3-yl]benzonitrile 2,2,2-trifluoroacetate tert-Butyl (3S,9aS)-3-(3-cyano-4-fluoro-2-methylphenyl)hexahydropyrazino[2,1-c][1,4]oxazine-8(1H)-carboxylate (1.88 g, 5.01 mmol) was treated with 10 mL TFA at RT for 1 h. The TFA was then removed under reduced pressure to yield the title compound. LC-MS: M+1=276: $^1$H-NMR (600 MHz, DMSO) δ ppm 7.954 (dd, J=8.7, 6.25 Hz, 1H), 7.412 (t, J=8.85 Hz, 1H), 4.939 (dd, J=8.4, 2.75 Hz, 1H), 3.848 (d, J=11.8 Hz, 1H), 3.762 (b, 1H), 3.189-3.536 (m, 8H), 3.072 (d, J=12 Hz, 1) 2.485 (s, 3H).

INTERMEDIATE 49A

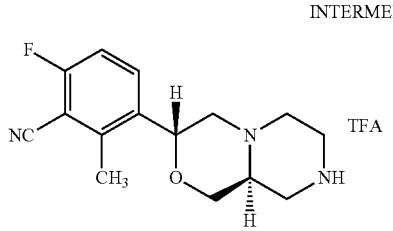

6-fluoro-2-methyl-3-[(3R,9aS)-octahydropyrazino[2,1-c][1,4]oxazin-3-yl]benzonitrile 2,2,2-trifluoroacetate tert-Butyl (3R,9aS)-3-(3-cyano-4-fluoro-2-methylphenyl)hexahydropyrazino[2,1-c][1,4]oxazine-8(1H)-carboxylate (1.73 g, 4.61 mmol) was treated with 10 mL TFA at RT for 1 h. The trifluoroacetic acid was then removed under reduced pressure to yield the title compound. LC-MS: M+1=276: $^1$H-NMR (600 MHz, DMSO) δ ppm 7.724 (dd, J=9.0, 6.2 Hz, 1H), 7.353 (t, J=8.85 Hz, 1H), 4.738 (d, J=10.3 Hz, 1H), 3.924 (d, J=11.10 Hz, 1H), 3.386 (t, J=11.65 Hz, 1H), 3.285 (d, J=12.3 Hz, 1H), 3.20 (d, J=11.8 Hz, 1H), 3.01 (b, 1H), 2.934 (d, J=11.6 Hz, 1H), 2.884 (d, J=11.0 Hz, 1H), 2.642 (b, 1H), 2.476 (s, 3H), 2.47 (b, 1H), 2.329-2.367 (m, 1H), 2.054-2.089 (m, 1H).

INTERMEDIATE 49C-1 (Method 1)

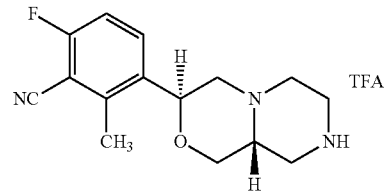

6-fluoro-2-methyl-3-[(3S,9aR)-octahydropyrazino[2,1-c][1,4]oxazin-3-yl]benzonitrile 2,2,2-trifluoroacetate (3S,9aR)-tert-Butyl 3-(3-cyano-4-fluoro-2-methylphenyl)hexahydropyrazino[2,1-c][1,4]oxazine-8(1H)-carboxylate (3.00 g, 7.99 mmol) was dissolved in TFA (10 mL) and stirred for 1 hr. The trifluoroacetic acid was removed under reduced pressure and azeotroped with dichloroethane (3×) then was dried over high vacuum to yield the title compound: LC-MS (IE, m/z): 276 [M+1]$^+$; $^1$H-NMR (500 MHz, DMSO) δ ppm 7.755 (dd, J=8.75, 6.2 Hz, 1H), 7.38 (t, J=8.85 Hz, 1H), 4.80 (d, J=10.1 Hz, 1H), 3.98 (dd, J=11.25, 2.5 Hz, 1H), 3.456 (t, J=10.7 Hz, 1H), 3.354 (d, J=12.6 Hz, 1H), 3.273 (d, J=11.8 Hz, 1H), 2.984-3.089 (m, 3H), 2.715 (t, J=11.37 Hz, 1H), 2.639 (t, J=10 Hz, 1H), 2.50 (s, 3H), 2.46 (b, 1H), 2.337 (t. J=10.9 Hz, 1H).

INTERMEDIATE 49C-2 (Method 2)

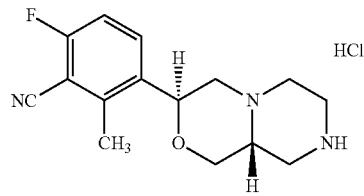

6-fluoro-2-methyl-3-[(3S,9aR)-octahydropyrazino[2,1-c][1,4]oxazin-3-yl]benzonitrile hydrochloride (3S,9aR)-tert-Butyl 3-(3-cyano-4-fluoro-2-methylphenyl)hexahydropyrazino[2,1-c][1,4]oxazine-8(1H)-carboxylate (158.8 g, 423.0 mmol) was suspended with 318 mL of 2-propanol. The resulting slurry was treated with HCl solution in 2-propanol (5.5 M, 1000 mL, 5499 mmol), and the mixture was heated to 50° C. for 2 hours. The mixture was concentrated to remove approximately 400 mL of 2-propanol, then was cooled to rt and agitated overnight. The mixture was filtered to collect the solid product and the wet cake was washed with 50 mL of 2-propanol. The filter cake was dried under vacuum for two days at 40° C. with nitrogen bleed to afford the title compound.

INTERMEDIATE 49D

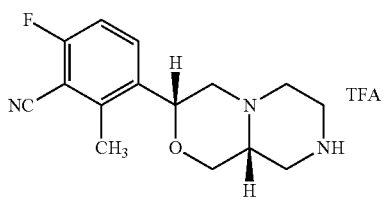

6-fluoro-2-methyl-3-[(3R,9aR)-octahydropyrazino[2,1-c][1,4]oxazin-3-yl]benzonitrile 2,2,2-trifluoroacetate (3R,9aR)-tert-Butyl 3-(3-cyano-4-fluoro-2-methylphenyl)hexahydropyrazino[2,1-c][1,4]oxazine-8(1H)-carboxylate (1.09 g, 2.90 mmol) was stirred in trifluoroacetic acid (10 mL) for 1 h then concentrated and azeotroped with dichloroethane (3×) to yield the title compound. LC-MS (IE, m/z): 276 [M+1]$^+$; $^1$H-NMR (500 MHz, DMSO) δ ppm 7.989 (t, J=6.4 Hz, 1H), 7.416 (t, J=8.85 Hz, 1H), 4.959 (dd, J=7.75, 2.35 Hz, 1H), 3.855 (d, J=11.9 Hz, 1H), 3.755 (b, 1H), 3.236-3.54 (m, 8H), 3.066 (d, J=11.5 Hz, 1H), 2.50 (s, 3H).

INTERMEDIATE 50A

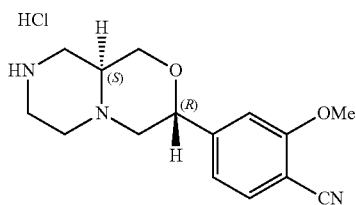

2-Methoxy-4-[(3S,9aR)-octahydropyrazino[2,1-c][1,4]oxazin-3-yl]benzonitrile hydrochloride tert-Butyl (3S,9aR)-3-(4-cyano-3-methoxyphenyl)hexahydropyrazino[2,1-c][1,4]oxazine-8(1H)-carboxylate (520 mg, 1.39 mmol) was dissolved in 10 mL of 4 M HCl in dioxane and stirred at room temperature for 8 h. The mixture was concentrated to ¼ the original volume and diluted with 10 mL of diethyl ether. The precipitate was filtered and dried under high vacuum to provide the title amine HCl salt: $^1$H NMR (DMSO-d$_6$, E (trans) isomer, 500 MHz) δ 7.76 (d, J=8.0 Hz, 1H), 7.25 (s, 1H), 7.11 (d, J=7.9 Hz, 1H), 5.0 (bs, 1H), 4.17 (bs, 1H), 3.94 (s, 3H), 3.85-3.60 (bs, 2H), 3.62-3.34 (m, 6H), 1.69 (bs, 2H); LC/MS: (IE, m/z) [M+1]$^+$=274.

INTERMEDIATE 50B

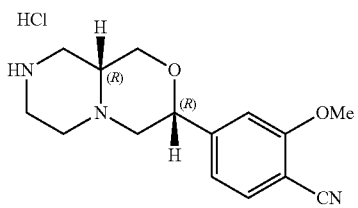

2-Methoxy-4-[(3R,9aR)-octahydropyrazino[2,1-c][1,4]oxazin-3-yl]benzonitrile hydrochloride tert-Butyl (3R,9aR)-3-(4-cyano-3-methoxyphenyl)hexahydropyrazino[2,1-c][1,4]oxazine-8(1H)-carboxylate (120 mg, 0.321 mmol) was dissolved in 10 mL of 4 M HCl in dioxane and stirred at room temperature for 8 h. The mixture was concentrated to ¼ the original volume and diluted with 10 mL of diethyl ether. The precipitate was filtered and dried under high vacuum to provide the title amine HCl salt: NMR (DMSO-d$_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]$^+$=274.

INTERMEDIATE 50C

2-Methoxy-4-[(3R,9aS)-octahydropyrazino[2,1-c][1,4]oxazin-3-yl]benzonitrile hydrochloride tert-Butyl (3R,9aS)-3-(4-cyano-3-methoxyphenyl)hexahydropyrazino[2,1-c][1,4]oxazine-8(1H)-carboxylate (90.0 mg, 0.241 mmol) was dissolved in 5 mL of 4 M HCl in dioxane and stirred at room temperature for 8 h. The mixture was concentrated to ¼ the original volume and diluted with 10 mL of diethyl ether. The precipitate was filtered and dried under high vacuum to provide the title amine HCl salt: $^1$H NMR (DMSO-d$_6$, E (trans) isomer, 500 MHz) δ 7.68 (d, J=8.0 Hz, 1H), 7.19 (s, 1H), 7.07 (d, J=8.0 Hz, 1H), 4.65 (dd, J=1.8 Hz, J=1.6 Hz, 1H), 3.91 (s, 3H), 3.82 (dd, J=3.0 Hz, 1H), 3.32-3.27 (m, 2H), 2.87-2.62 (m, 5H), 2.24-1.98 (m, 3H); LC/MS: (IE, m/z) [M+1]$^+$=274.

INTERMEDIATE 50D

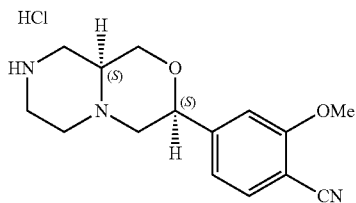

2-Methoxy-4-[(3S,9aS)-octahydropyrazino[2,1-c][1,4]oxazin-3-yl]benzonitrile hydrochloride tert-Butyl (3S,9aS)-3-(4-cyano-3-methoxyphenyl)hexahydropyrazino[2,1-c][1,4]oxazine-8(1H)-carboxylate (38.0 mg, 0.102 mmol) was dissolved in 10 mL of 4 M HCl in dioxane and stirred at room temperature for 8 h. The mixture was concentrated to ¼ the original volume and diluted with 5 mL of diethyl ether. The precipitate was filtered and dried under high vacuum to provide the title amine HCl salt: $^1$H NMR (DMSO-d$_6$, Z (cis) isomer, 500 MHz) δ 7.77 (d, J=7.9

Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]⁺=274.

The intermediates shown in Table 1 below were prepared in an analagous fashion to that described for the syntheses of Intermediates I-49B: 6-fluoro-2-methyl-3-[(3S,9aS)-octahydropyrazino[2,1-c][1,4]oxazin-3-yl]benzonitrile 2,2,2-trifluoroacetate, and I-50D: 2-methoxy-4-[(3S,9aS)-octahydropyrazino[2,1-c][1,4]oxazin-3-yl]benzonitrile hydrochloride, using either HCl or TFA to remove the Boc protective group present in the corresponding Boc-piperazine precursor (the acid used in the reaction and the mass spec data are provided in Table 1). It is understood that the resulting intermediates may be TFA or HCl salts, or they may be obtained as free base amines by routine partitioning of the product with an organic solvent and a basic aqueous solution such as saturated sodium bicarbonate solution and concentration of the resulting organic solution.

TABLE 1

| Intermediate No. | |
| --- | --- |
| 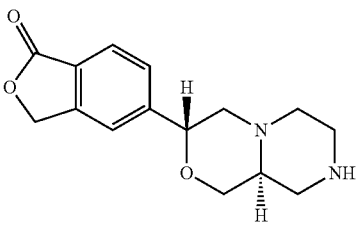<br>TFA<br>MS (M + H)⁺ 275 | 51A |
| 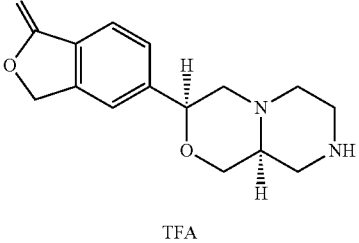<br>TFA<br>MS (M + H)⁺ 275 | 51B |
| 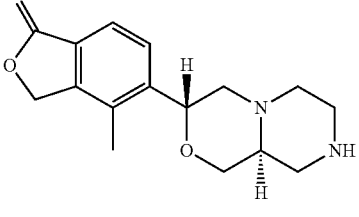<br>TFA<br>MS (M + H)⁺ 289 | 52A |

TABLE 1-continued

| Intermediate No. | |
| --- | --- |
| 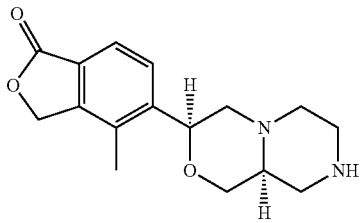<br>TFA<br>MS (M + H)⁺ 289 | 52B |
| 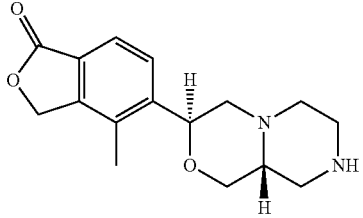<br>TFA<br>MS (M + H)⁺ 289 | 52C |
| 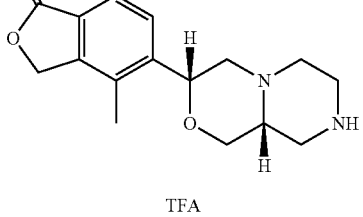<br>TFA<br>MS (M + H)⁺ 289 | 52D |
| 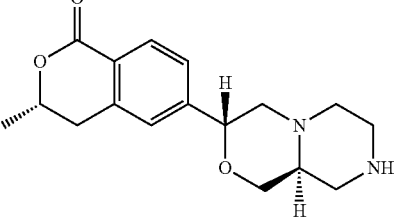<br>HCl | 53 |
| 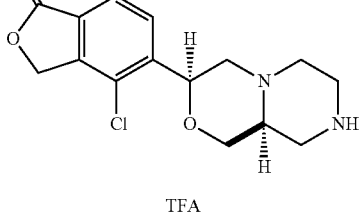<br>TFA<br>MS (M + H)⁺ 309 | 54 |

TABLE 1-continued

Intermediate No.

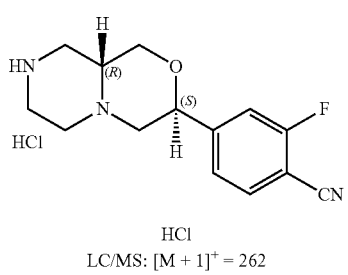

55

TFA
MS (M + H)+ 262

56

TFA
LC/MS: [(M + 1)]+ = 305

57A

HCl
LC/MS: [M + 1]+ = 262

57B

HCl
LC/MS: [M + 1]+ = 262

58

TFA
LC/MS: [(M + 1)]+ = 280

TABLE 1-continued

Intermediate No.

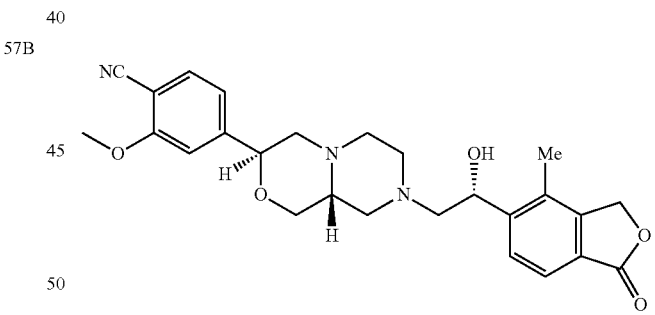

59

TFA
LC/MS: [(M + 1)]+ = 292

60A

TFA
LC/MS: [(M + 1)]+ = 292

60B

TFA

Example 1

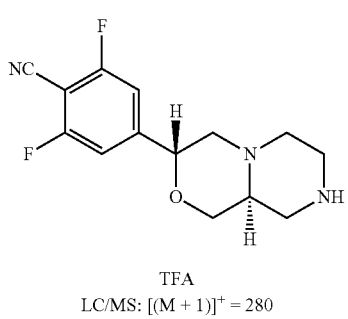

4-{(3S,9aR)-8-[(2R)-2-hydroxy-2-(4-methyl-1-oxo-1,3-dihydro-2-benzofuran-5-yl)ethyl]octahydropyrazino[2,1-c][1,4]oxazin-3-yl}-2-methoxybenzonitrile To a microwave tube containing 4-methyl-5-[(2R)-oxiran-2-yl]-2-benzofuran-1(3H)-one (200 mg, 1.05 mmol) dissolved in absolute ethanol (3 mL) was added the free base of 2-methoxy-4-[(3S,9aR)-octahydropyrazino[2,1-c][1,4]oxazin-3-yl]benzonitrile (345 mg, 1.26 mmol). The reaction was heated in a microwave apparatus for 1 hour at 150° C. The crude product was allowed to cool and concentrated in vacuo. Purification was achieved by mass directed reverse-phase HPLC, and the regioisomeric by-product was removed using SFC HPLC 50% IPA+0.2% DEA/CO$_2$ in MeOH on Chiralcel OD-H column to yield the title product. LC/MS: (IE, m/z) [(M+1)]$^+$=464.04.

Example 2

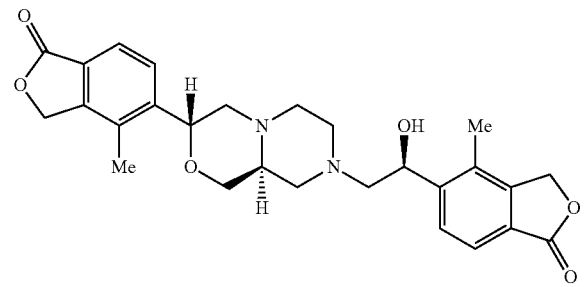 [SMILES: Cc1c([C@H](O)CN2CCN3C[C@@H](c4ccc5c(c4C)COC5=O)OC[C@@H]3C2)ccc2c1COC2=O]

5-((S)-1-hydroxy-2-((3R,9aS)-3-(4-methyl-1-oxo-1,3-dihydroisobenzofuran-5-yl)hexahydropyrazino[2,1-c][1,4]oxazin-8(1H)-yl)ethyl)-4-methylisobenzofuran-1(3H)-one 4-methyl-5-((3R,9aS)-octahydropyrazino[2,1-c][1,4]oxazin-3-yl)isobenzofuran-1(3H)-one (0.06 g, 0.21 mmol), (S)-4-methyl-5-(oxiran-2-yl)isobenzofuran-1(3H)-one (0.08 g, 0.41 mmol) were added into a 5 ml microwave tube; to the tube was added EtOH (2.5 mL), the tube was degassed and purged with N$_2$, followed by heating in a microwave reactor at 140° C. for 1 hr.; LC indicated completion of the reaction and formation of the desired product. The solution was concentrated to dryness, re-dissolved in DCM, adsorbed on silica gel and loaded into an MPLC, with the solvent systems of 5% MeOH in DCM, to isolate the title product. (LC/MS: [(M+1)]$^+$=479; (LC/MS: [(M+1)]$^+$=479.

Example 3

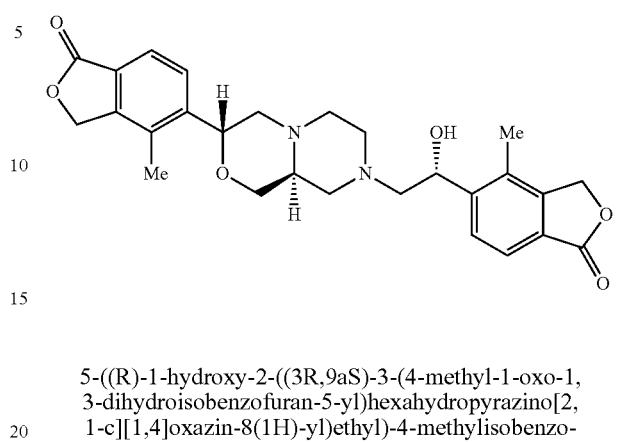

5-((R)-1-hydroxy-2-((3R,9aS)-3-(4-methyl-1-oxo-1,3-dihydroisobenzofuran-5-yl)hexahydropyrazino[2,1-c][1,4]oxazin-8(1H)-yl)ethyl)-4-methylisobenzofuran-1(3H)-one To a 5 ml microwave tube was added 4-methyl-5-((3R,9aS)-octahydropyrazino[2,1-c][1,4]oxazin-3-yl)isobenzofuran-1(3H)-one (0.13 mg, 0.43 mmol), (R)-4-methyl5-(oxiran-2-yl)isobenzofuran-1(3H)-one (0.12 g, 0.65 mmol) and ethanol (4 mL). The tube was degassed and purged with N$_2$, followed by heating in a microwave reactor at 140° C. for 1 hr.; LC indicated completion of the reaction and formation of the desired product. The solution was concentrated to dryness, re-dissolved in DCM, adsorbed onto silica gel and loaded into an MPLC, with the solvent systems of 5% MeOH in DCM, to isolate the title product. (LC/MS: [(M+1)]$^+$=479.

The Examples in Table 2 were prepared in an analogous fashion to that described for Examples 1-3 above starting from amines and epoxides prepared as described above. The compounds were isolated as free bases, HCl salts, or TFA salts. In cases where the epoxides used are racemic two diastereomeric products are produced. These diastereomers can be separated by SFC chiral HPLC using one of several chiral HPLC (columns used in the below examples are indicated).

TABLE 2

| EXAMPLE | Amine Intermediate | Epoxide Intermediate | Structure, name and characterization |
|---|---|---|---|
| 4 | 50D | 4 | (3S,9aS)-3-(4-cyano-3-methoxyphenyl)-8-[2-hydroxy-2-(4-methyl-1-oxo-1,3-dihydro-2-benzofuran-5-yl)ethyl]octahydropyrazino[2,1-c][1,4]oxazin-5-ium chloride; LC/MS: [(M + 1)]$^+$ = 464 |

TABLE 2-continued

| EXAMPLE | Amine Intermediate | Epoxide Intermediate | Structure, name and characterization |
|---|---|---|---|
| 5 | 49A | 4B | 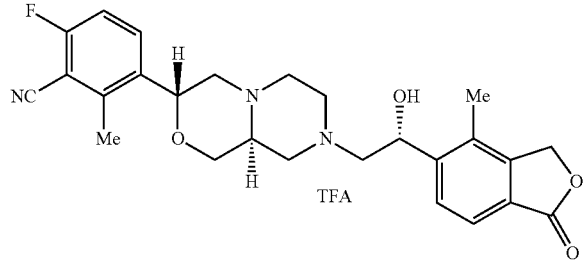 [SMILES: Cc1c([C@@H]2CN3CCN(C[C@H](O)c4ccc5c(c4C)COC5=O)C[C@H]3CO2)ccc(F)c1C#N ; "TFA"]<br>(3R,9aS)-3-(3-cyano-4-fluoro-2-methylphenyl)-8-[(2R)-2-hydroxy-2-(4-methyl-1-oxo-1,3-dihydro-2-benzofuran-5-yl)ethyl]octahydropyrazino[2,1-c][1,4]oxazin-5-ium trifluoroacetate; LC/MS: [(M + 1)]$^+$ = 466 |
| 6 | 49B | 4B | 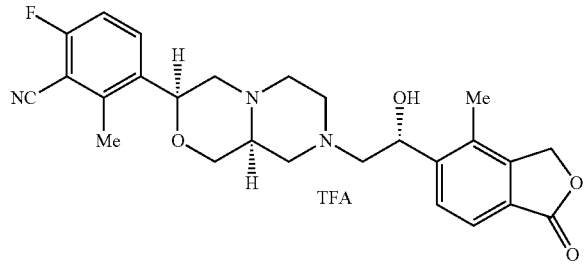 [SMILES: Cc1c([C@H]2CN3CCN(C[C@H](O)c4ccc5c(c4C)COC5=O)C[C@H]3CO2)ccc(F)c1C#N ; "TFA"]<br>(3S,9aS)-3-(3-cyano-4-fluoro-2-methylphenyl)-8-[(2R)-2-hydroxy-2-(4-methyl-1-oxo-1,3-dihydro-2-benzofuran-5-yl)ethyl]octahydropyrazino[2,1-c][1,4]oxazin-5-ium trifluoroacetate; LC/MS: [(M + 1)]$^+$ = 466 |
| 7 | 49C | 4B | 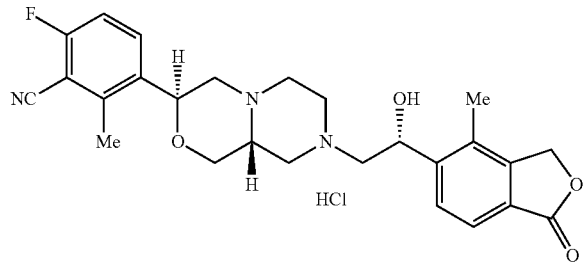 [SMILES: Cc1c([C@H]2CN3CCN(C[C@H](O)c4ccc5c(c4C)COC5=O)C[C@@H]3CO2)ccc(F)c1C#N ; Cl]<br>(3S,9aR)-3-(3-cyano-4-fluoro-2-methylphenyl)-8-[(2R)-2-hydroxy-2-(4-methyl-1-oxo-1,3-dihydro-2-benzofuran-5-yl)ethyl]octahydropyrazino[2,1-c][1,4]oxazin-5-ium chloride; LC/MS: [(M + 1)]$^+$ = 466 |
| 8 | 49D | 4B | 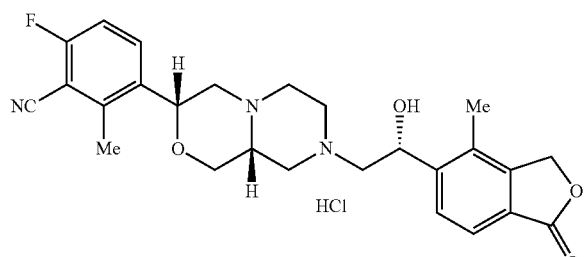<br>(3R,9aR)-3-(3-cyano-4-fluoro-2-methylphenyl)-8-[(2R)-2-hydroxy-2-(4-methyl-1-oxo-1,3-dihydro-2-benzofuran-5-yl)ethyl]octahydropyrazino[2,1-c][1,4]oxazin-5-ium chloride; LC/MS: [(M + 1)]$^+$ = 466 |

TABLE 2-continued

| EXAMPLE | Amine Intermediate | Epoxide Intermediate | Structure, name and characterization |
|---|---|---|---|
| 9 | 52A | 19 | 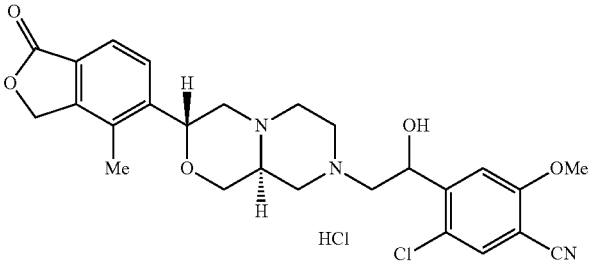 [SMILES: COc1cc(C(O)CN2CCN3C[C@@H](c4ccc5c(c4C)COC5=O)OC[C@@H]3C2)c(Cl)cc1C#N ; Cl]<br>(3R,9aS)-8-[2-(2-chloro-4-cyano-5-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride; LC/MS: [(M + 1)]$^+$ = 498 |
| 10 | 51A | 19 | 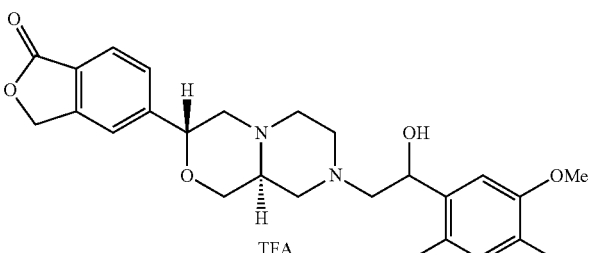<br>(3R,9aS)-8-[2-(2-chloro-4-cyano-5-methoxyphenyl)-2-hydroxyethyl]-3-(1-oxo-1,3-dihydro-2-benzofuran-5-yl)octahydropyrazino[2,1-c][1,4]oxazin-5-ium trifluoroacetate; LC/MS: [(M + 1)]$^+$ = 484 |
| 11 | 51A | 4B | 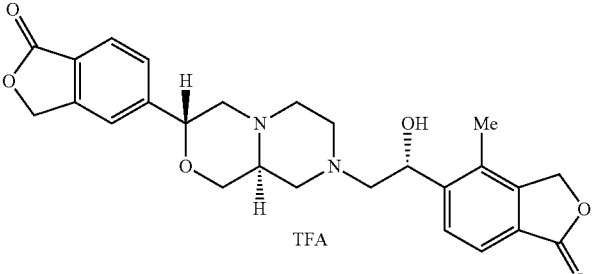<br>(3R,9aS)-8-[(2R)-2-hydroxy-2-(4-methyl-1-oxo-1,3-dihydro-2-benzofuran-5-yl)ethyl]-3-(1-oxo-1,3-dihydro-2-benzofuran-5-yl)octahydropyrazino[2,1-c][1,4]oxazin-5-ium trifluoroacetatep; LC/MS: [(M + 1)]$^+$ = 465 |
| 12 | 51A | 4A | 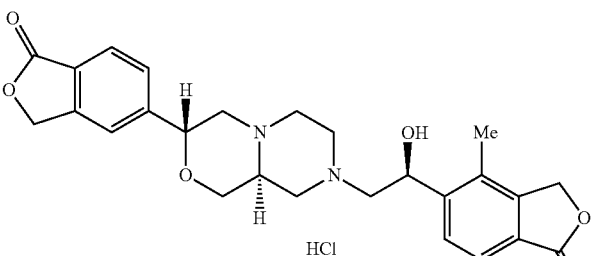<br>(3R,9aS)-8-[(2S)-2-hydroxy-2-(4-methyl-1-oxo-1,3-dihydro-2-benzofuran-5-yl)ethyl]-3-(1-oxo-1,3-dihydro-2-benzofuran-5-yl)octahydropyrazino[2,1-c][1,4]oxazin-5-ium chloride; LC/MS: [(M + 1)]$^+$ = 465 |

TABLE 2-continued

| EXAMPLE | Amine Intermediate | Epoxide Intermediate | Structure, name and characterization |
|---|---|---|---|
| 13 | 52A | 20 | 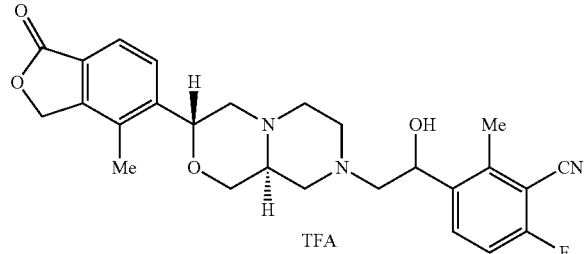<br>(3R,9aS)-8-[2-(3-cyano-4-fluoro-2-methylphenyl)-2-hydroxyethyl]-3-(4-methyl-1-oxo-1,3-dihydro-2-benzofuran-5-yl)octahydropyrazino[2,1-c][1,4]oxazin-5-ium trifluoroacetate;<br>LC/MS: [(M + 1)]$^+$ = 466 |
| 14 | 50A | 15 | 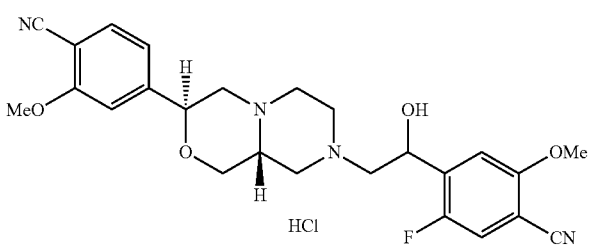 [SMILES: COc1cc([C@H]2CN3CCN(CC(O)c4cc(OC)c(C#N)cc4F)C[C@@H]3CO2)ccc1C#N ; Cl]<br>(3S,9aR)-8-[2-(4-cyano-2-fluoro-5-methoxyphenyl)-2-hydroxyethyl]-3-(4-cyano-3-methoxyphenyl)octahydropyrazino[2,1-c][1,4]oxazin-5-ium chloride; LC/MS: [(M + 1)]$^+$ = 467 |
| 15 | 52A | 15 | 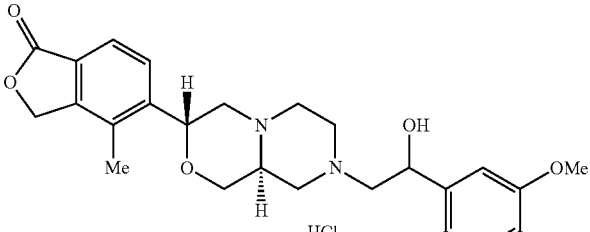<br>(3R,9aS)-8-[2-(4-cyano-2-fluoro-5-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride;<br>LC/MS: [(M + 1)]$^+$ = 482 |
| 16 | 49A | 29 | 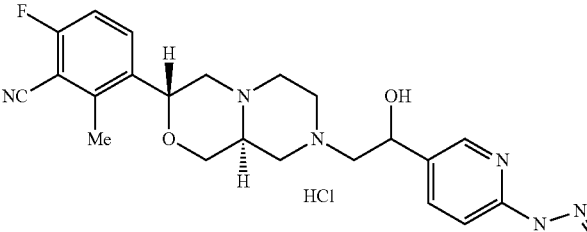<br>(3R,9aS)-3-(3-cyano-4-fluoro-2-methylphenyl)-8-{2-hydroxy-2-[6-(1H-tetrazol-1-yl)pyridin-3-yl]ethyl}octahydropyrazino[2,1-c][1,4]oxazin-5-ium chloride; single isomer with unknown stereochemistry at pyridine benzylic center, first peak to elute from chiral HPLC separation using Chiralpak AD column;<br>LC/MS: [(M + 1)]$^+$ = 465 |

TABLE 2-continued

| EXAMPLE | Amine Intermediate | Epoxide Intermediate | Structure, name and characterization |
|---|---|---|---|
| 17 | 49B | 29 | 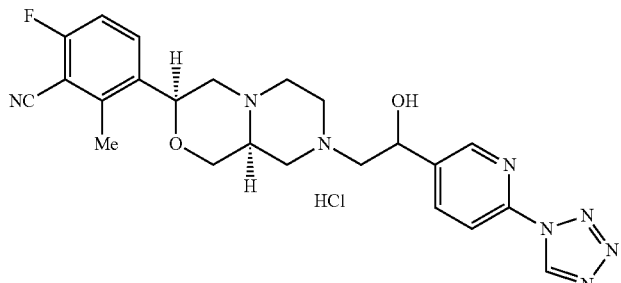<br>(3S,9aS)-3-(3-cyano-4-fluoro-2-methylphenyl)-8-{2-hydroxy-2-[6-(1H-tetrazol-1-yl)pyridin-3-yl]ethyl}octahydropyrazino[2,1-c][1,4]oxazin-5-ium chloride; single isomer with unknown stereochemistry at pyridine benzylic center, first peak to elute from chiral HPLC separation using Chiralpak AD column; LC/MS: [(M + 1)]$^+$ = 465 |
| 18 | 49B | 29 | 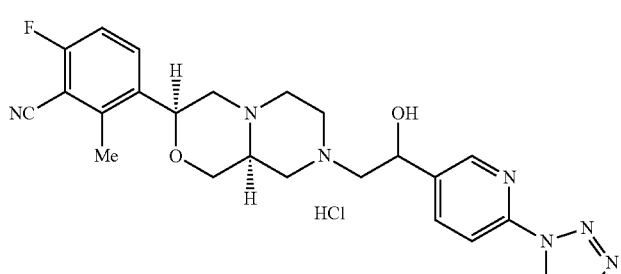<br>(3S,9aS)-3-(3-cyano-4-fluoro-2-methylphenyl)-8-{2-hydroxy-2-[6-(1H-tetrazol-1-yl)pyridin-3-yl]ethyl}octahydropyrazino[2,1-c][1,4]oxazin-5-ium chloride; single isomer with unknown stereochemistry at pyridine benzylic center, second peak to elute from chiral HPLC separation using Chiralpak AD column; LC/MS: [(M + 1)]$^+$ = 465 |
| 19 | 49A | 30 | Faster eluting isomer<br>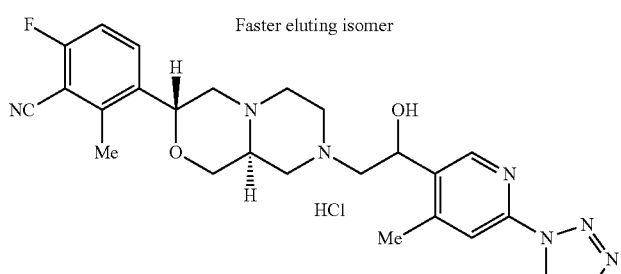<br>(3R,9aS)-3-(3-cyano-4-fluoro-2-methylphenyl)-8-{2-hydroxy-2-[4-methyl-6-(1H-tetrazol-1-yl)pyridin-3-yl]ethyl}octahydropyrazino[2,1-c][1,4]oxazin-5-ium chloride; single isomer with unknown stereochemistry at pyridine benzylic center, first peak to elute from chiral HPLC separation using Chiralpak AD column; LC/MS: [(M + 1)]$^+$ = 479 |

TABLE 2-continued

| EXAMPLE | Amine Intermediate | Epoxide Intermediate | Structure, name and characterization |
|---|---|---|---|
| 20 | 49A | 30 | Slower eluting isomer<br><br>(3R,9aS)-3-(3-cyano-4-fluoro-2-methylphenyl)-8-{2-hydroxy-2-[4-methyl-6-(1H-tetrazol-1-yl)pyridin-3-yl]ethyl}octahydropyrazino[2,1-c][1,4]oxazin-5-ium chloride; single isomer with unknown stereochemistry at pyridine benzylic center, second peak to elute from chiral HPLC separation using Chiralpak AD column;<br>LC/MS: [(M + 1)]$^+$ = 479 |
| 21 | 49A | 31 | Faster eluting isomer<br><br>(3R,9aS)-3-(3-cyano-4-fluoro-2-methylphenyl)-8-{2-hydroxy-2-[2-methyl-6-(1H-tetrazol-1-yl)pyridin-3-yl]ethyl}octahydropyrazino[2,1-c][1,4]oxazin-5-ium chloride; single isomer with unknown stereochemistry at pyridine benzylic center, first peak to elute from chiral HPLC separation using Chiralpak AD column;<br>LC/MS: [(M + 1)]$^+$ = 479 |
| 22 | 49D | 32 | (3R,9aR)-3-(3-cyano-4-fluoro-2-methylphenyl)-8-{2-hydroxy-2-[3-(1H-tetrazol-1-yl)phenyl]ethyl}octahydropyrazino[2,1-c][1,4]oxazin-5-ium chloride; single isomer with unknown stereochemistry at benzylic center, first peak to elute from chiral HPLC separation using Chiralcel OJ column; LC/MS: [(M + 1)]$^+$ = 464 |
| 23 | 49D | 32 | (3R,9aR)-3-(3-cyano-4-fluoro-2-methylphenyl)-8-{2-hydroxy-2-[3-(1H-tetrazol-1-yl)phenyl]ethyl}octahydropyrazino[2,1-c][1,4]oxazin-5-ium chloride; single isomer with unknown stereochemistry at benzylic center, second peak to elute from chiral HPLC separation using Chiralcel OJ column; LC/MS: [(M + 1)]$^+$ = 464 |

TABLE 2-continued

| EXAMPLE | Amine Intermediate | Epoxide Intermediate | Structure, name and characterization |
|---|---|---|---|
| 24 | 49A | 5 | 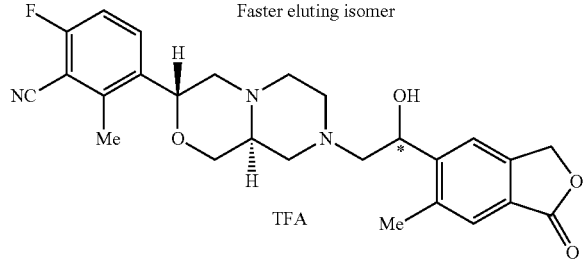 [SMILES: Cc1cc2c(cc1C(O)CN1CCN3C[C@@H](c4ccc(F)c(C#N)c4C)OC[C@@H]3C1)COC2=O ; "Slower eluting isomer" ; "TFA"] Faster eluting isomer<br><br>(3R,9aS)-3-(3-cyano-4-fluoro-2-methylphenyl)-8-[2-hydroxy-2-(6-methyl-1-oxo-1,3-dihydro-2-benzofuran-5-yl)ethyl]octahydropyrazino[2,1-c][1,4]oxazin-5-ium trifluoroacetate; single isomer with unknown stereochemistry at benzylic center, first peak to elute from chiral HPLC separation using Chiralpak AD column; LC/MS: $[(M + 1)]^+$ = 466 |
| 25 | 49A | 5 | 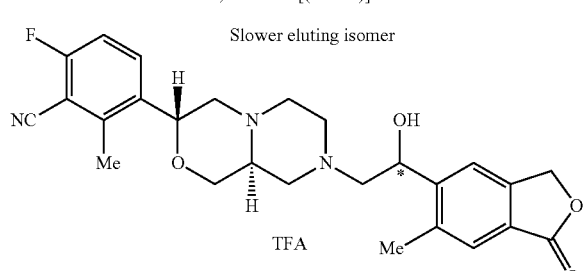 Slower eluting isomer<br><br>(3R,9aS)-3-(3-cyano-4-fluoro-2-methylphenyl)-8-[2-hydroxy-2-(6-methyl-1-oxo-1,3-dihydro-2-benzofuran-5-yl)ethyl]octahydropyrazino[2,1-c][1,4]oxazin-5-ium trifluoroacetate; single isomer with unknown stereochemistry at benzylic center, second peak to elute from chiral HPLC separation using Chiralpak AD column; LC/MS: $[(M + 1)]^+$ = 466 |
| 26 | 49B | 5 | 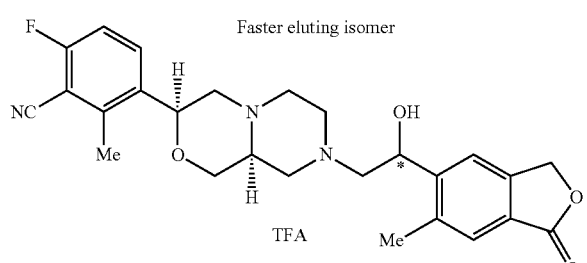 Faster eluting isomer<br><br>(3S,9aS)-3-(3-cyano-4-fluoro-2-methylphenyl)-8-[2-hydroxy-2-(6-methyl-1-oxo-1,3-dihydro-2-benzofuran-5-yl)ethyl]octahydropyrazino[2,1-c][1,4]oxazin-5-ium trifluoroacetate; single isomer with unknown stereochemistry at benzylic center, first peak to elute from chiral HPLC separation using Chiralpak AD column; LC/MS: $[(M + 1)]^+$ = 466 |
| 27 | 49B | 5 | 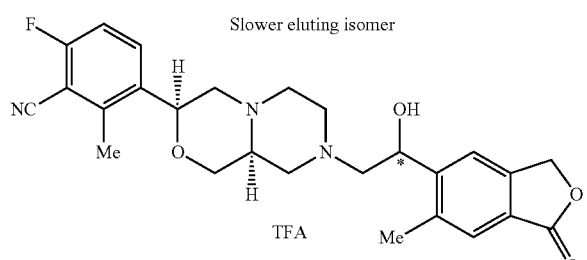 Slower eluting isomer<br><br>(3S,9aS)-3-(3-cyano-4-fluoro-2-methylphenyl)-8-[2-hydroxy-2-(6-methyl-1-oxo-1,3-dihydro-2-benzofuran-5-yl)ethyl]octahydropyrazino[2,1-c][1,4]oxazin-5-ium trifluoroacetate; single isomer with unknown stereochemistry at benzylic center, second peak to elute from chiral HPLC separation using Chiralpak AD column; LC/MS: $[(M + 1)]^+$ = 466 |

TABLE 2-continued

| EXAMPLE | Amine Intermediate | Epoxide Intermediate | Structure, name and characterization |
|---|---|---|---|
| 28 | 57B | 4B | (3S,9aR)-3-(4-cyano-3-fluorophenyl)-8-[(2R)-2-hydroxy-2-(4-methyl-1-oxo-1,3-dihydro-2-benzofuran-5-yl)ethyl]octahydropyrazino[2,1-c][1,4]oxazin-8-ium chloride; LC/MS: $[(M + 1)]^+ = 452$ |
| 29 | 57A | 4B | (3R,9aR)-3-(4-cyano-3-fluorophenyl)-8-[(2R)-2-hydroxy-2-(4-methyl-1-oxo-1,3-dihydro-2-benzofuran-5-yl)ethyl]octahydropyrazino[2,1-c][1,4]oxazin-8-ium chloride; LC/MS: $[(M + 1)]^+ = 452$ |
| 30 | 60A | 4B | (3R,9aS)-3-(4-cyano-3-fluoro-2-methoxyphenyl)-8-[(2R)-2-hydroxy-2-(4-methyl-1-oxo-1,3-dihydro-2-benzofuran-5-yl)ethyl]octahydropyrazino[2,1-c][1,4]oxazin-8-ium chloride; LC/MS: $[(M + 1)]^+ = 482$ |
| 31 | 60A | 4A | (3R,9aS)-3-(4-cyano-3-fluoro-2-methoxyphenyl)-8-[(2S)-2-hydroxy-2-(4-methyl-1-oxo-1,3-dihydro-2-benzofuran-5-yl)ethyl]octahydropyrazino[2,1-c][1,4]oxazin-8-ium chloride; LC/MS: $[(M + 1)]^+ = 482$ |

TABLE 2-continued

| EXAMPLE | Amine Intermediate | Epoxide Intermediate | Structure, name and characterization |
|---|---|---|---|
| 32 | 60B | 4B | 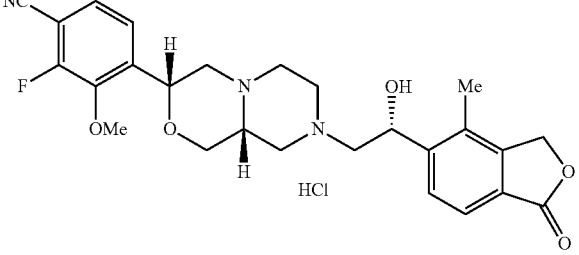<br>(3R,9aR)-3-(4-cyano-3-fluoro-2-methoxyphenyl)-8-[(2R)-2-hydroxy-2-(4-methyl-1-oxo-1,3-dihydro-2-benzofuran-5-yl)ethyl]octahydropyrazino[2,1-c][1,4]oxazin-8-ium chloride;<br>LC/MS: $[(M + 1)]^+ = 482$ |
| 33 | 52D | 21 | 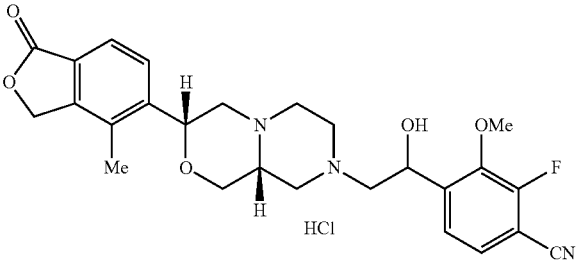 [SMILES: COc1c(C(O)CN2CCN3C[C@@H](c4ccc5c(c4C)COC5=O)OC[C@H]3C2)ccc(C#N)c1F ; Cl]<br>(3R,9aR)-8-[2-(4-cyano-3-fluoro-2-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride;<br>LC/MS: $[(M + 1)]^+ = 482$ |
| 34 | 52A | 21 | 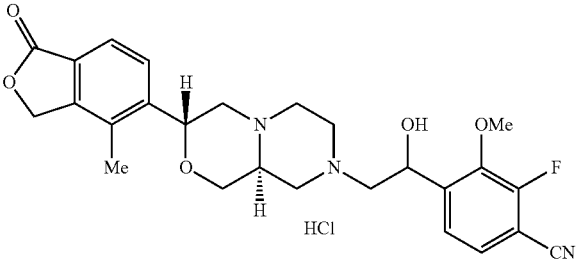 [SMILES: COc1c(C(O)CN2CCN3C[C@@H](c4ccc5c(c4C)COC5=O)OC[C@@H]3C2)ccc(C#N)c1F ; Cl]<br>(3R,9aS)-8-[2-(4-cyano-3-fluoro-2-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride;<br>LC/MS: $[(M + 1)]^+ = 482$ |
| 35 | 52B | 21 | 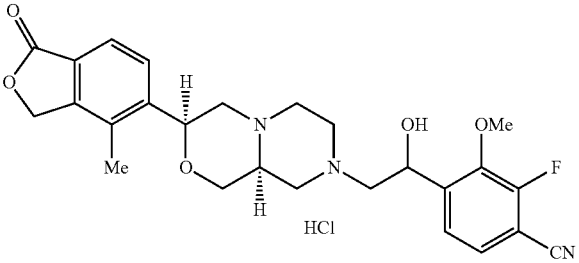 [SMILES: COc1c(C(O)CN2CCN3C[C@H](c4ccc5c(c4C)COC5=O)OC[C@@H]3C2)ccc(C#N)c1F ; Cl]<br>(3S,9aS)-8-[2-(4-cyano-3-fluoro-2-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride;<br>LC/MS: $[(M + 1)]^+ = 482$ |

TABLE 2-continued

| EXAMPLE | Amine Intermediate | Epoxide Intermediate | Structure, name and characterization |
|---|---|---|---|
| 36 | 52C | 15 | 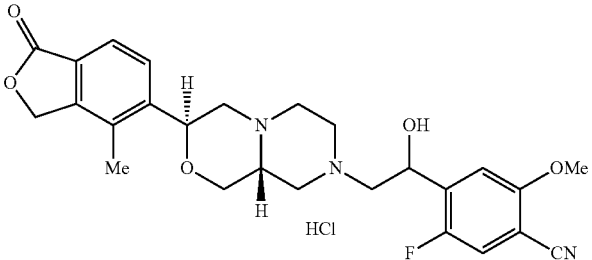 [SMILES: COc1cc(C(O)CN2CCN3C[C@H](c4ccc5c(c4C)COC5=O)OC[C@H]3C2)c(F)cc1C#N ; Cl]<br>(3S,9aR)-8-[2-(4-cyano-2-fluoro-5-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride;<br>LC/MS: [(M + 1)]$^+$ = 482 |
| 37 | 52A | 15 | 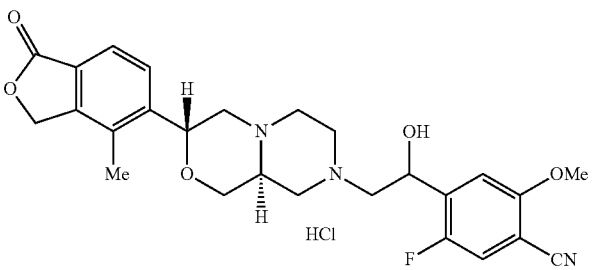 [SMILES: COc1cc(C(O)CN2CCN3C[C@@H](c4ccc5c(c4C)COC5=O)OC[C@@H]3C2)c(F)cc1C#N ; Cl]<br>(3R,9aS)-8-[2-(4-cyano-2-fluoro-5-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, second peak to elute from chiral HPLC separation LC/MS: [(M + 1)]$^+$ = 482 |
| 38 | 52A | 24 | 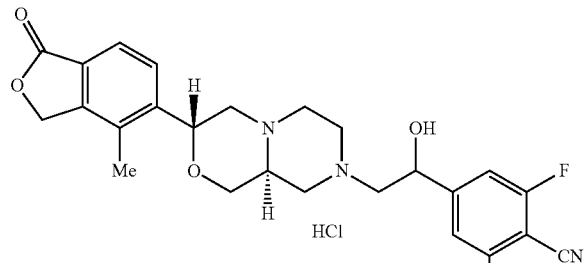<br>(3R,9aS)-8-[2-(4-cyano-3,5-difluorophenyl)-2-hydroxyethyl]-3-(4-methyl-1-oxo-1,3-dihydro-2-benzofuran-5-yl)octahydropyrazino[2,1-c][1,4]oxazin-5-ium chloride; LC/MS: [(M + 1)]$^+$ = 470 |
| 39 | 52A | 21 | 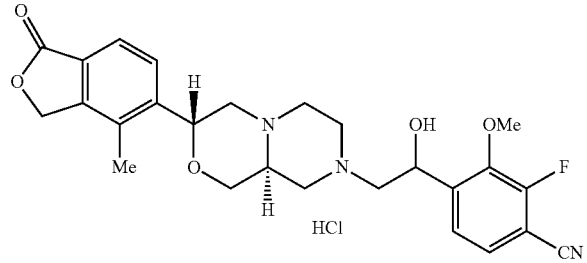 [SMILES: COc1c(C(O)CN2CCN3C[C@@H](c4ccc5c(c4C)COC5=O)OC[C@@H]3C2)ccc(C#N)c1F ; Cl]<br>(3R,9aS)-8-[2-(4-cyano-3-fluoro-2-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride;<br>LC/MS: [(M + 1)]$^+$ = 482 |

TABLE 2-continued

| EXAMPLE | Amine Intermediate | Epoxide Intermediate | Structure, name and characterization |
|---|---|---|---|
| 40 | 52B | 21 | 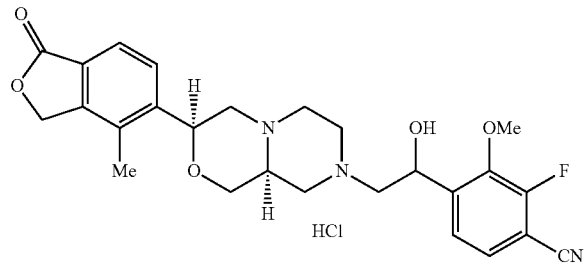 [SMILES: COc1c(C(O)CN2CCN3C[C@H](c4ccc5c(c4C)COC5=O)OC[C@@H]3C2)ccc(C#N)c1F ; Cl]<br>(3S,9aS)-8-[2-(4-cyano-3-fluoro-2-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride; LC/MS: [(M + 1)]$^+$ = 482 |
| 41 | 52D | 21 | 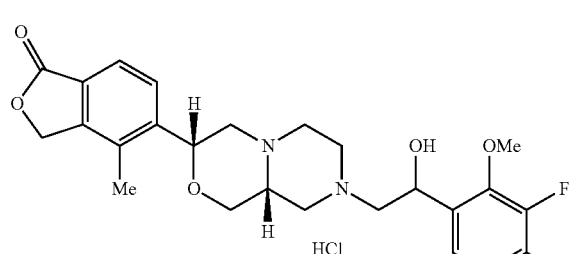<br>(3R,9aR)-8-[2-(4-cyano-3-fluoro-2-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, first peak to elute from chiral HPLC separation; LC/MS: [(M + 1)]$^+$ = 482 |
| 42 | 52A | 5 | 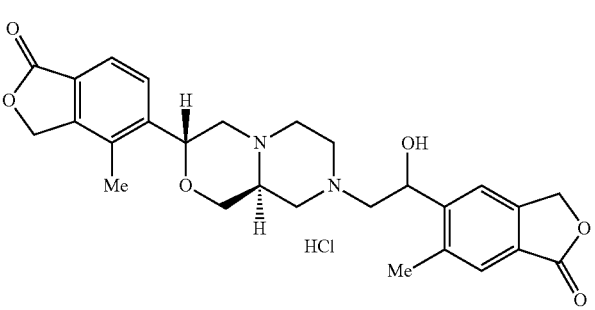 [SMILES: Cc1cc2c(cc1C(O)CN1CCN3C[C@@H](c4ccc5c(c4C)COC5=O)OC[C@@H]3C1)COC2=O ; Cl]<br>(3R,9aS)-8-[2-hydroxy-2-(6-methyl-1-oxo-1,3-dihydro-2-benzofuran-5-yl)ethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, first peak to elute from chiral HPLC separation; LC/MS: [(M + 1)]$^+$ = 479 |
| 43 | 52A | 5 | 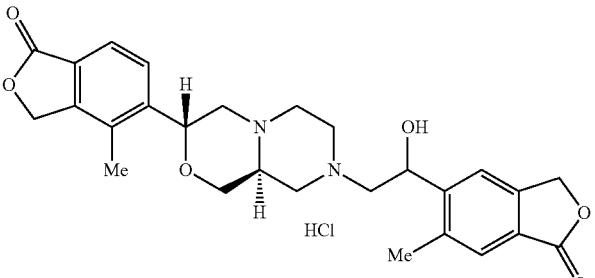<br>(3R,9aS)-8-[2-hydroxy-2-(6-methyl-1-oxo-1,3-dihydro-2-benzofuran-5-yl)ethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, second peak to elute from chiral HPLC separation; LC/MS: [(M + 1)]$^+$ = 479 |

TABLE 2-continued

| EXAMPLE | Amine Intermediate | Epoxide Intermediate | Structure, name and characterization |
|---|---|---|---|
| 44 | 52A | 10B | (3R,9aS)-8-{2-hydroxy-2-[(3S)-3-methyl-1-oxo-3,4-dihydro-1H-isochromen-6-yl]ethyl}-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, first peak to elute from chiral HPLC separation using Chirapak AS column; LC/MS: [(M + 1)]$^+$ = 493 |
| 45 | 52A | 10B | (3R,9aS)-8-{2-hydroxy-2-[(3S)-3-methyl-1-oxo-3,4-dihydro-1H-isochromen-6-yl]ethyl}-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, second peak to elute from chiral HPLC separation using Chirapak AS column; LC/MS: [(M + 1)]$^+$ = 493 |
| 46 | 52A | 10A | (3R,9aS)-8-{2-hydroxy-2-[(3R)-3-methyl-1-oxo-3,4-dihydro-1H-isochromen-6-yl]ethyl}-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, first peak to elute from chiral HPLC separation using Chiralcel OD-H column; LC/MS: [(M + 1)]$^+$ = 493 |

TABLE 2-continued

| EXAMPLE | Amine Intermediate | Epoxide Intermediate | Structure, name and characterization |
|---|---|---|---|
| 47 | 52A | 12 | 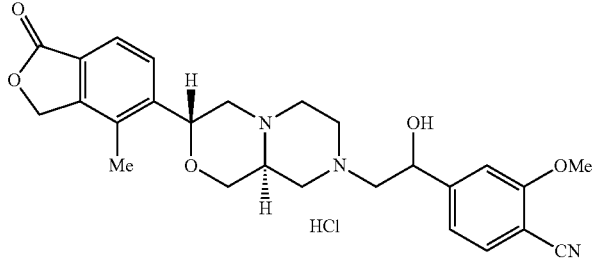 [SMILES: COc1cc(C(O)CN2CCN3C[C@@H](c4ccc5c(c4C)COC5=O)OC[C@@H]3C2)ccc1C#N ; Cl]<br>(3R,9aS)-8-[2-(4-cyano-3-methoxyphenyl)-2-hydroxyethyl]-3-(4-methyl-1-oxo-1,3-dihydro-2-benzofuran-5-yl)octahydropyrazino[2,1-c][1,4]oxazin-8-ium chloride; single isomer with unknown stereochemistry at benzylic center, second peak to elute from chiral HPLC separation; LC/MS: $[(M + 1)]^+ = 464$ |
| 48 | 52A | 26 | 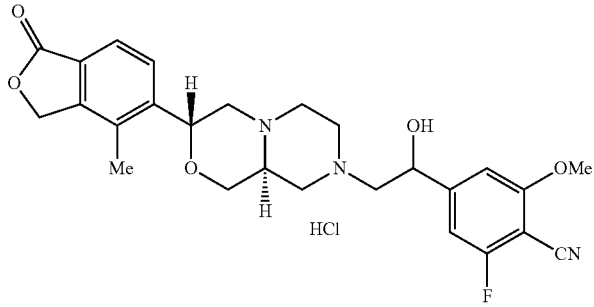 [SMILES: COc1cc(C(O)CN2CCN3C[C@@H](c4ccc5c(c4C)COC5=O)OC[C@@H]3C2)cc(F)c1C#N ; Cl]<br>(3R,9aS)-8-[2-(4-cyano-3-fluoro-5-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 482$ |
| 49 | 52A | 24 | 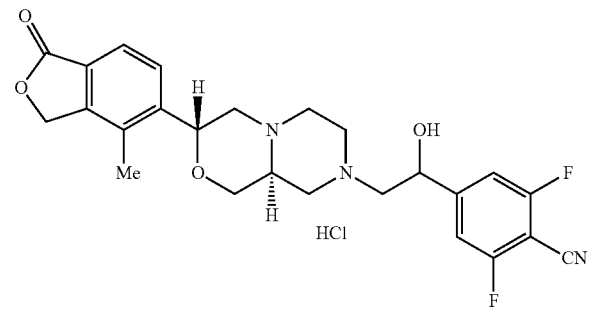 [SMILES: Cc1c([C@@H]2CN3CCN(CC(O)c4cc(F)c(C#N)c(F)c4)C[C@H]3CO2)ccc2c1COC2=O ; Cl]<br>(3R,9aS)-8-[2-(4-cyano-3,5-difluorophenyl)-2-hydroxyethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, first peak to elute from chiral HPLC separation; LC/MS: $[(M + 1)]^+ = 470$ |

| EXAMPLE | Amine Intermediate | Epoxide Intermediate | Structure, name and characterization |
|---|---|---|---|
| 50 | 52A | 8 | 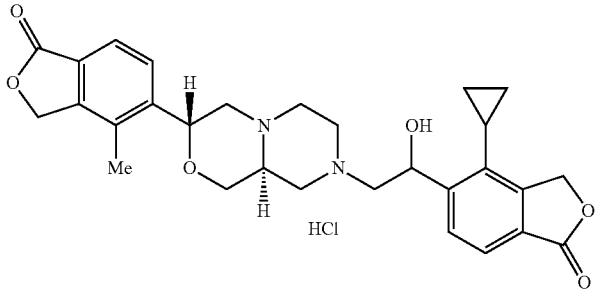 [SMILES: Cc1c([C@@H]2CN3CCN(CC(O)c4ccc5c(c4C4CC4)COC5=O)C[C@H]3CO2)ccc2c1COC2=O ; Cl]<br>(3R,9aS)-8-[2-(4-cyclopropyl-1-oxo-1,3-dihydro-2-benzofuran-5-yl)-2-hydroxyethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, second peak to elute from chiral HPLC separation using Chiralcel OD column; LC/MS: $[(M + 1)]^+ = 505$ |
| 51 | 52A | 8 | 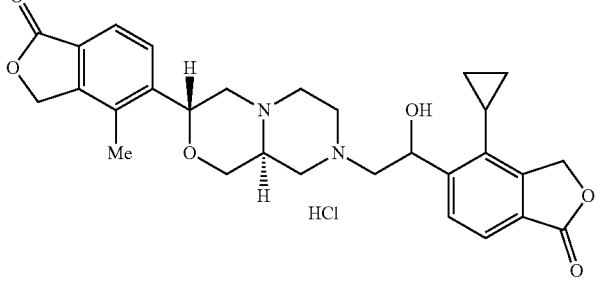<br>(3R,9aS)-8-[2-(4-cyclopropyl-1-oxo-1,3-dihydro-2-benzofuran-5-yl)-2-hydroxyethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, second peak to elute from chiral HPLC separation using Chiralcel OD column; LC/MS: $[(M + 1)]^+ = 505$ |
| 52 | 58 | 4B | 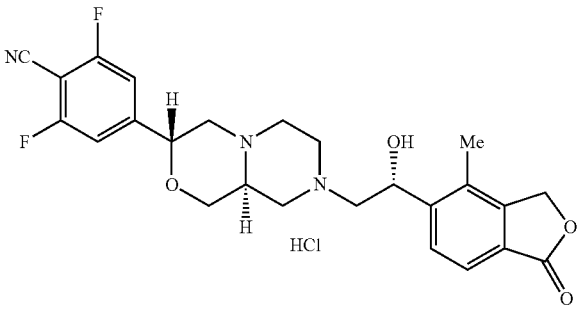 [SMILES: Cc1c([C@@H](O)CN2CCN3C[C@@H](c4cc(F)c(C#N)c(F)c4)OC[C@@H]3C2)ccc2c1COC2=O ; Cl]<br>(3R,9aS)-3-(4-cyano-3,5-difluorophenyl)-8-[(2R)-2-hydroxy-2-(4-methyl-1-oxo-1,3-dihydro-2-benzofuran-5-yl)ethyl]octahydropyrazino[2,1-c][1,4]oxazin-8-ium chloride; LC/MS: $[(M + 1)]^+ = 470$ |

TABLE 2-continued

| EXAMPLE | Amine Intermediate | Epoxide Intermediate | Structure, name and characterization |
|---|---|---|---|
| 53 | 59 | 4B | 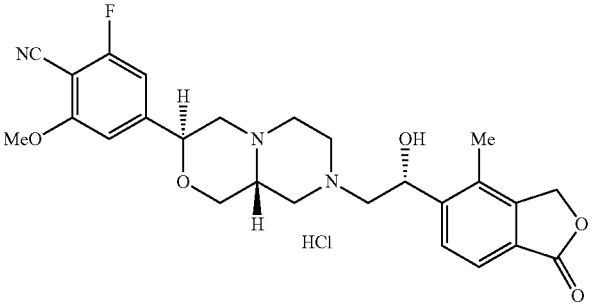 [SMILES: COc1cc([C@H]2CN3CCN(C[C@H](O)c4ccc5c(c4C)COC5=O)C[C@@H]3CO2)cc(F)c1C#N ; Cl]<br>(3S,9aR)-3-(4-cyano-3-fluoro-5-methoxyphenyl)-8-[(2R)-2-hydroxy-2-(4-methyl-1-oxo-1,3-dihydro-2-benzofuran-5-yl)ethyl]octahydropyrazino[2,1-c][1,4]oxazin-8-ium chloride; LC/MS: [(M + 1)]$^+$ = 482 |
| 54 | 52A | 26 | 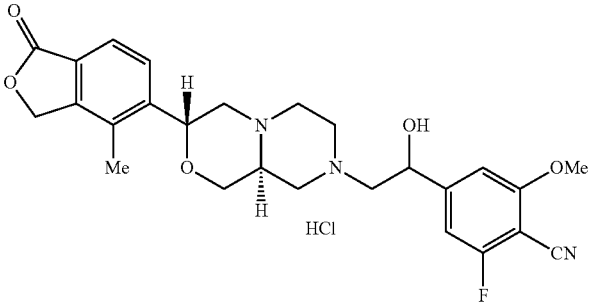 [SMILES: COc1cc(C(O)CN2CCN3C[C@@H](c4ccc5c(c4C)COC5=O)OC[C@@H]3C2)cc(F)c1C#N ; Cl]<br>(3R,9aS)-8-[2-(4-cyano-3-fluoro-5-methoxyphenyl)-2-hydroxyethyl]-3-(4-methyl-1-oxo-1,3-dihydro-2-benzofuran-5-yl)octahydropyrazino[2,1-c][1,4]oxazin-5-ium chloride; single isomer with unknown stereochemistry at benzylic center, second peak to elute from chiral HPLC separation; LC/MS: [(M + 1)]$^+$ = 482 |
| 55 | 56 | 4B | 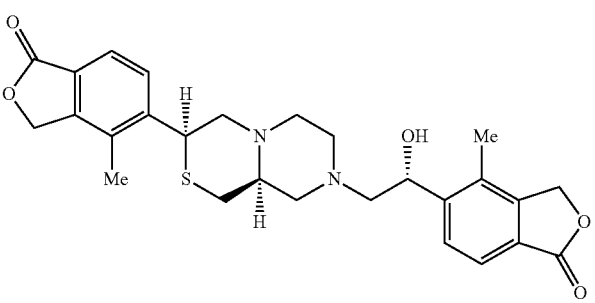 [SMILES: Cc1c([C@@H](O)CN2CCN3C[C@H](c4ccc5c(c4C)COC5=O)SC[C@@H]3C2)ccc2c1COC2=O]<br>5-{(3S,9aS)-8-[(2R)-2-hydroxy-2-(4-methyl-1-oxo-1,3-dihydro-2-benzofuran-5-yl)ethyl]octahydropyrazino[2,1-c][1,4]thiazin-3-yl}-4-methyl-2-benzofuran-1(3H)-one; LC/MS: [(M + 1)]$^+$ = 495 |

Example 56

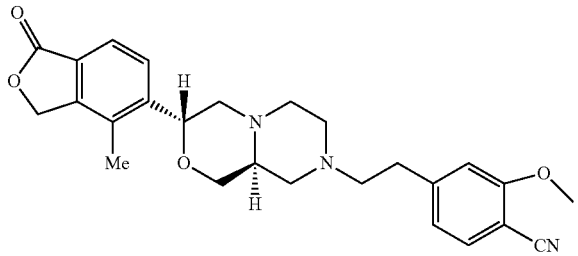 [SMILES: COc1cc(CCN2CCN3C[C@@H](c4ccc5c(c4C)COC5=O)OC[C@@H]3C2)ccc1C#N]

2-methoxy-4-(2-((3R,9aS)-3-(4-methyl-1-oxo-1,3-dihydroisobenzofuran-5-yl)hexahydropyrazino[2,1-c][1,4]oxazin-8(1H)-yl)ethyl)benzonitrile 4-Methyl-5-((3R,9aS)-octahydropyrazino[2,1-c][1,4]oxazin-3-yl)isobenzofuran-1 (3H)-one (100 mg, 0.249 mmol), 2-methoxy-4-(2-oxoethyl)benzonitrile (87 mg, 0.497 mmol) and TEA (0.069 ml, 0.497 mmol) were dissolved in dichloroethane (10 ml), then sodium triacetoxyborohydride (158 mg, 0.746 mmol) was added and the mixture was stirred at room temperature for 48 hrs. The reaction was washed with NaHCO₃ solution and brine. The organic 10 layer was separated, dried over Na₂SO₄, filtered and concentrated. The residue was purified mass directed HPLC and re-purified by TLC prep-plate using 5% (NH₄OH: MeOH 1:9) in DCM solvent system to yield 2-methoxy-4-(2-((3R,9aS)-3-(4-methyl-1-oxo-1,3-dihydroisobenzofuran-5-yl)hexahydropyrazino[2,1-c][1,4]oxazin-8(1H)-yl)ethyl)benzonitrile.
LC-MS (IE, m/z): 448 [M+1]⁺; ¹H-NMR (500 MHz, DMSO) δ ppm 7.688 (d, J=8.0 Hz, 1H), 7.631 (d, J=8.0 Hz, 1H), 7.610 (d, J=8.0 Hz, 1H), 7.167 (s, 1H), 6.98 (d, J=7.8 Hz, 1H), 5.40 (m, 2H), 4.863 (d, J=10 Hz, 1H), 3.907 (s, 3H), 3.882 (d, J=2.9 Hz, 1H), 3.417 (t, J=10.7 Hz, 1H), 2.863 (d, J=9.6 Hz, 1H), 2.819 (m, 4H), 2.723 (d, J=8.0 Hz, 1H), 2.564 (t, J=7.6 Hz, 2H), 2.282 (s, 3H), 2.151-2.265 (m, 3H), 2.004 (t, J=11.0 Hz, 1H), 1.767 (t, J=10.3 Hz, 1H).

Example 57

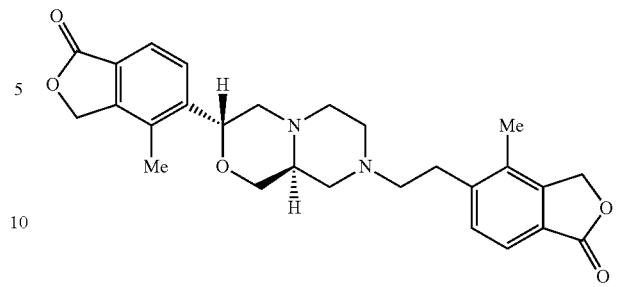

4-Methyl-5-((3R,9aS)-8-(2-(4-methyl-1-oxo-1,3-dihydroisobenzofuran-5-yl)ethyl)octahydropyrazino[2,1-c][1,4]oxazin-3-yl)isobenzofuran-1(3H)-one 4-Methyl-5-((3R,9aS)-octahydropyrazino[2,1-c][1,4]oxazin-3-yl)isobenzofuran-1 (3H)-one (100 mg, 0.249 mmol), 2-(4-methyl-1-oxo-1,3-dihydroisobenzofuran-5-yl)acetaldehyde (70.9 mg, 0.373 mmol) and TEA (0.104 ml, 0.746 mmol) were dissolved in dichloroethane (10 ml) then sodium triacetoxyborohydride (158 mg, 0.746 mmol) was added and the mixture stirred at room temperature for 2 hrs. When LC-MS showed product peak, the reaction was washed with NaHCO₃ solution and brine then dried over Na₂SO₄, filtered and concentrated. The residue was purified by mass directed HPLC and re-purified by TLC prep-plate using 5% (NH₄OH: MeOH 1:9) in DCM solvent system to yield 4-methyl-5-((3R,9aS)-8-(2-(4-methyl-1-oxo-1,3-dihydroisobenzofuran-5-yl)ethyl) octahydropyrazino[2,1-c][1,4]oxazin-3-yl)isobenzofuran-1(3H)-one. LC-MS (IE, m/z): 463 [M+1]⁺. ¹H-NMR (500 MHz, CDCl3) δ ppm 7.82 (d, J=7.8 Hz, 1H), 7.751 (d, J=7.3 Hz, 1H), 7.736 (d, J=7.3 Hz, 1H), 7.387 (d, J=7.8 Hz, 1H), 5.283 (s, 4H), 4.978 (d, J=9.1 Hz, 1H), 3.996 (d, J=9.9 Hz, 1H), 3.578 (t, J=10.8 Hz, 1H), 2.96-3.0 (m, 3H), 2.891 (t, J=10 Hz, 2H), 2.834 (d, J=9.4 Hz, 1H), 2.631 (t, J=8.0 Hz, 2H), 2.403-2.551 (m, 2H), 2.364 (s, 3H), 2.338 (s, 3H), 2.272 (t, J=10.8 Hz, 1H), 1.972 (t, J-10.3 Hz, 1H).

The Examples in Table 3 were prepared in an analogous fashion to that described for Examples 56-57 above starting from amines and aldehydes or ketones prepared as described above. The compounds were isolated as free bases, HCl salts, or TFA salts. In cases where ketones are used two diastereomeric products are produced. These diastereomers can be separated by SFC chiral HPLC using one of several chiral HPLC (columns used in the below examples are indicated).

TABLE 3

| EXAMPLE | Amine Intermediate | Aldehyde Intermediate | Structure, name and characterization |
|---|---|---|---|
| 58 | 51A | 11 | ![structure] <br> (3R,9aS)-8-[2-(4-cyano-3-methoxyphenyl)ethyl]-3-(1-oxo-1,3-dihydro-2-benzofuran-5-yl)octahydropyrazino[2,1-c][1,4]oxazin-5-ium chloride; LC/MS: [(M + 1)]⁺ = 434 |

TABLE 3-continued

| EXAMPLE | Amine Intermediate | Aldehyde Intermediate | Structure, name and characterization |
|---------|-------------------|----------------------|--------------------------------------|
| 59 | 51B | 11 | (3S,9aS)-8-[2-(4-cyano-3-methoxyphenyl)ethyl]-3-(1-oxo-1,3-dihydro-2-benzofuran-5-yl)octahydropyrazino[2,1-c][1,4]oxazin-5-ium trifluoroacetate; LC/MS: $[(M+1)]^+ = 434$ |
| 60 | 52B | 11 | (3S,9aS)-8-[2-(4-cyano-3-methoxyphenyl)ethyl]-3-(4-methyl-1-oxo-1,3-dihydro-2-benzofuran-5-yl)octahydropyrazino[2,1-c][1,4]oxazin-5-ium trifluoroacetate; LC/MS: $[(M+1)]^+ = 448$ |
| 61 | 52C | 11 | (3S,9aR)-8-[2-(4-cyano-3-methoxyphenyl)ethyl]-3-(4-methyl-1-oxo-1,3-dihydro-2-benzofuran-5-yl)octahydropyrazino[2,1-c][1,4]oxazin-5-ium trifluoroacetate; LC/MS: $[(M+1)]^+ = 448$ |
| 62 | 51A | 1 | (3R,9aS)-3-(1-oxo-1,3-dihydro-2-benzofuran-5-yl)-8-[2-(1-oxo-1,3-dihydro-2-benzofuran-5-yl)ethyl]octahydropyrazino[2,1-c][1,4]oxazin-5-ium trifluoroacetate; LC/MS: $[(M+1)]^+ = 435$ |

TABLE 3-continued

| EXAMPLE | Amine Intermediate | Aldehyde Intermediate | Structure, name and characterization |
|---|---|---|---|
| 63 | 51B | 1 | 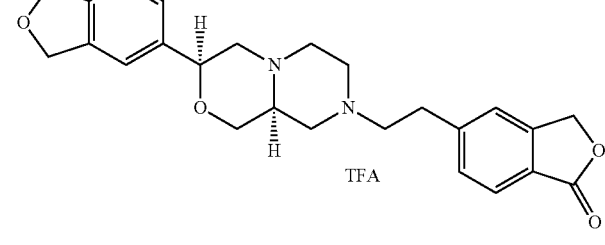<br>(3S,9aS)-3-(1-oxo-1,3-dihydro-2-benzofuran-5-yl)-8-[2-(1-oxo-1,3-dihydro-2-benzofuran-5-yl)ethyl]octahydropyrazino[2,1-c][1,4]oxazin-5-ium trifluoroacetate; LC/MS: [(M + 1)]⁺ = 435 |
| 64 | 52A | 1 | 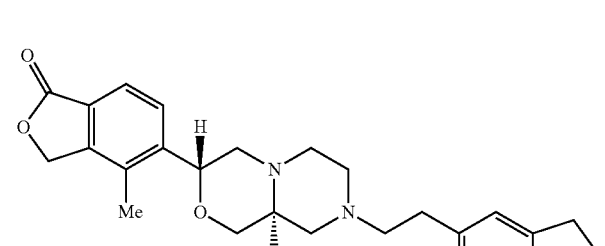<br>(3R,9aS)-3-(4-methyl-1-oxo-1,3-dihydro-2-benzofuran-5-yl)-8-[2-(1-oxo-1,3-dihydro-2-benzofuran-5-yl)ethyl]octahydropyrazino[2,1-c][1,4]oxazin-5-ium chloride; LC/MS: [(M + 1)]⁺ = 449 |
| 65 | 52B | 1 | 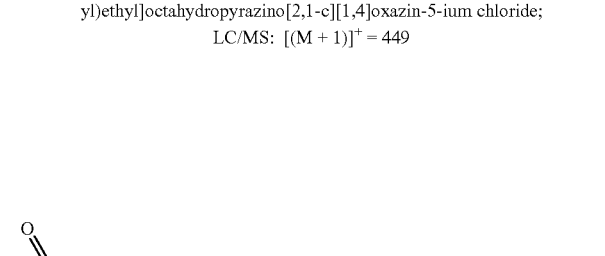<br>(3S,9aS)-3-(4-methyl-1-oxo-1,3-dihydro-2-benzofuran-5-yl)-8-[2-(1-oxo-1,3-dihydro-2-benzofuran-5-yl)ethyl]octahydropyrazino[2,1-c][1,4]oxazin-5-ium trifluoroacetate; LC/MS: [(M + 1)]⁺ = 449 |

TABLE 3-continued

| EXAMPLE | Amine Intermediate | Aldehyde Intermediate | Structure, name and characterization |
|---|---|---|---|
| 66 | 52B | 3 | (3S,9aS)-3-(4-methyl-1-oxo-1,3-dihydro-2-benzofuran-5-yl)-8-[2-(4-methyl-1-oxo-1,3-dihydro-2-benzofuran-5-yl)ethyl]octahydropyrazino[2,1-c][1,4]oxazin-5-ium trifluoroacetate; LC/MS: $[(M + 1)]^+ = 463$ |
| 67 | 52C | 3 | (3S,9aR)-3-(4-methyl-1-oxo-1,3-dihydro-2-benzofuran-5-yl)-8-[2-(4-methyl-1-oxo-1,3-dihydro-2-benzofuran-5-yl)ethyl]octahydropyrazino[2,1-c][1,4]oxazin-5-ium trifluoroacetate; LC/MS: $[(M + 1)]^+ = 463$ |
| 68 | 52D | 3 | (3R,9aR)-3-(4-methyl-1-oxo-1,3-dihydro-2-benzofuran-5-yl)-8-[2-(4-methyl-1-oxo-1,3-dihydro-2-benzofuran-5-yl)ethyl]octahydropyrazino[2,1-c][1,4]oxazin-5-ium trifluoroacetate; LC/MS: $[(M + 1)]^+ = 463$ |

TABLE 3-continued

| EXAMPLE | Amine Intermediate | Aldehyde Intermediate | Structure, name and characterization |
|---|---|---|---|
| 69 | 51A | 3 | 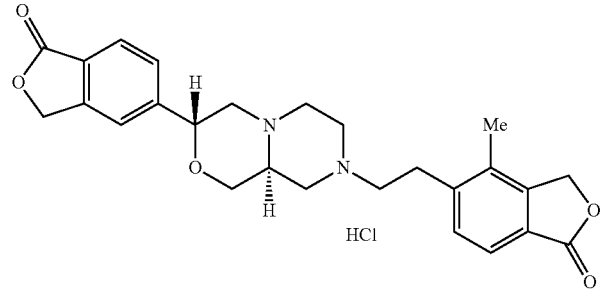<br>(3R,9aS)-8-[2-(4-methyl-1-oxo-1,3-dihydro-2-benzofuran-5-yl)ethyl]-3-(1-oxo-1,3-dihydro-2-benzofuran-5-yl)octahydropyrazino[2,1-c][1,4]oxazin-5-ium chloride; LC/MS: [(M + 1)]$^+$ = 449 |
| 70 | 51B | 3 | 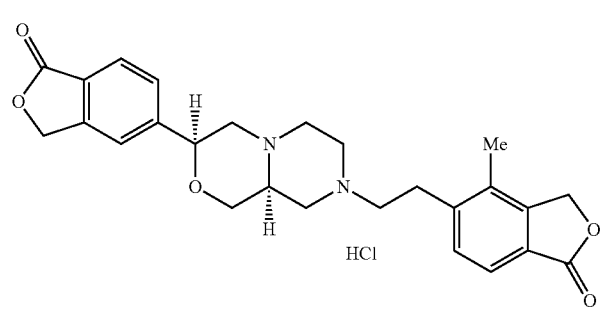<br>(3S,9aS)-8-[2-(4-methyl-1-oxo-1,3-dihydro-2-benzofuran-5-yl)ethyl]-3-(1-oxo-1,3-dihydro-2-benzofuran-5-yl)octahydropyrazino[2,1-c][1,4]oxazin-5-ium chloride; LC/MS: [(M + 1)]$^+$ = 449 |
| 71 | 50C | 3 | 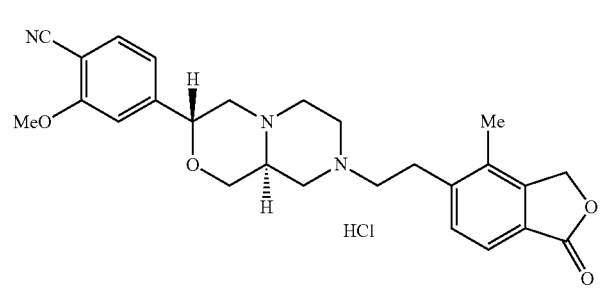<br>(3R,9aS)-3-(4-cyano-3-methoxyphenyl)-8-[2-(4-methyl-1-oxo-1,3-dihydro-2-benzofuran-5-yl)ethyl]octahydropyrazino[2,1-c][1,4]oxazin-8-ium chloride; LC/MS: [(M + 1)]$^+$ = 448 |

TABLE 3-continued

| EXAMPLE | Amine Intermediate | Aldehyde Intermediate | Structure, name and characterization |
|---|---|---|---|
| 72 | 55 | 3 | 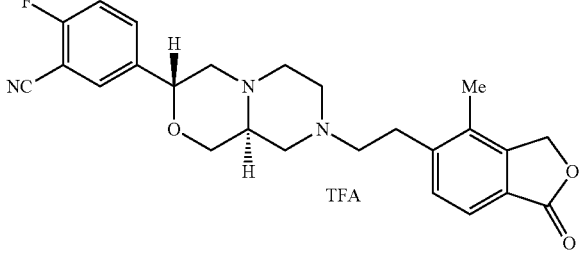 (3R,9aS)-3-(3-cyano-4-fluorophenyl)-8-[2-(4-methyl-1-oxo-1,3-dihydro-2-benzofuran-5-yl)ethyl]octahydropyrazino[2,1-c][1,4]oxazin-5-ium trifluoroacetate; LC/MS: [(M + 1)]$^+$ = 436 |
| 73 | 39 | 3 | 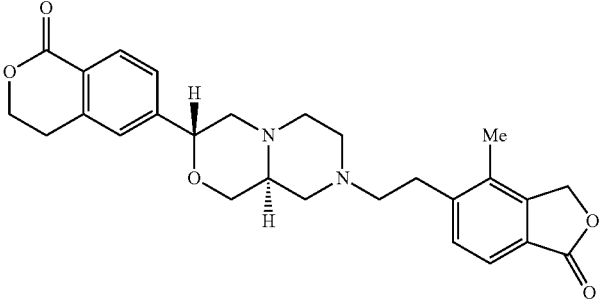 6-{(3R,9aS)-8-[2-(4-methyl-1-oxo-1,3-dihydro-2-benzofuran-5-yl)ethyl]octahydropyrazino[2,1-c][1,4]oxazin-3-yl}-3,4-dihydro-1H-isochromen-1-one; LC/MS: [(M + 1)]$^+$ = 463 |
| 74 | 50D | 3 | 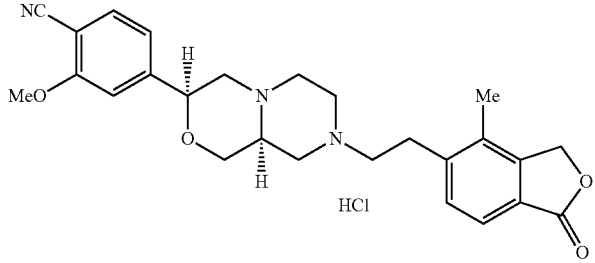 (3S,9aS)-3-(4-cyano-3-methoxyphenyl)-8-[2-(4-methyl-1-oxo-1,3-dihydro-2-benzofuran-5-yl)ethyl]octahydropyrazino[2,1-c][1,4]oxazin-8-ium chloride; LC/MS: [(M + 1)]$^+$ = 448 |
| 75 | 50A | 3 | 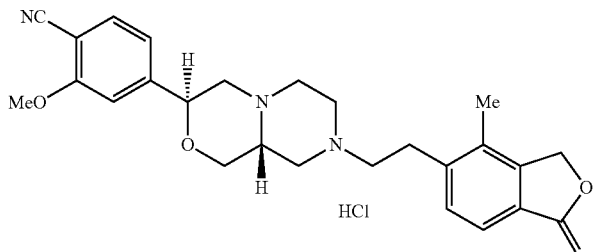 (3S,9aR)-3-(4-cyano-3-methoxyphenyl)-8-[2-(4-methyl-1-oxo-1,3-dihydro-2-benzofuran-5-yl)ethyl]octahydropyrazino[2,1-c][1,4]oxazin-8-ium chloride; LC/MS: [(M + 1)]$^+$ = 448 |

TABLE 3-continued

| EXAMPLE | Amine Intermediate | Aldehyde Intermediate | Structure, name and characterization |
|---|---|---|---|
| 76 | 50B | 3 | 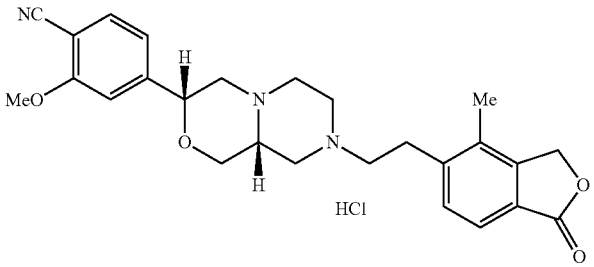<br>(3R,9aR)-3-(4-cyano-3-methoxyphenyl)-8-[2-(4-methyl-1-oxo-1,3-dihydro-2-benzofuran-5-yl)ethyl]octahydropyrazino[2,1-c][1,4]oxazin-8-ium chloride; LC/MS: [(M + 1)]$^+$ = 448 |
| 77 | 49C | 3 | 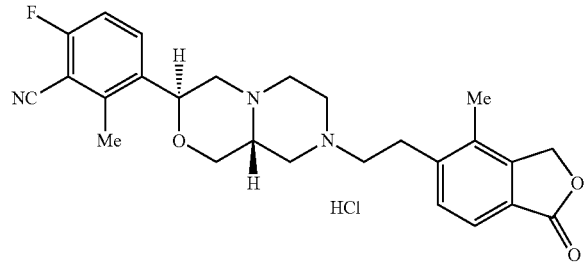<br>(3S,9aR)-3-(3-cyano-4-fluoro-2-methylphenyl)-8-[2-(4-methyl-1-oxo-1,3-dihydro-2-benzofuran-5-yl)ethyl]octahydropyrazino[2,1-c][1,4]oxazin-5-ium chloride; LC/MS: [(M + 1)]$^+$ = 450 |
| 78 | 49D | 3 | 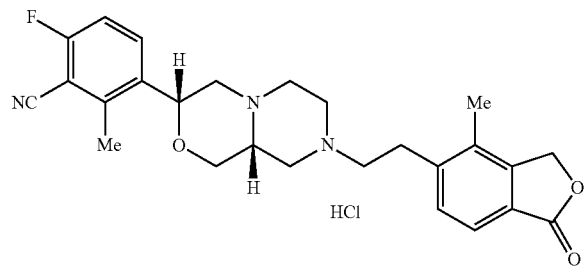<br>(3R,9aR)-3-(3-cyano-4-fluoro-2-methylphenyl)-8-[2-(4-methyl-1-oxo-1,3-dihydro-2-benzofuran-5-yl)ethyl]octahydropyrazino[2,1-c][1,4]oxazin-5-ium chloride; LC/MS: [(M + 1)]$^+$ = 450 |

TABLE 3-continued

| EXAMPLE | Amine Intermediate | Aldehyde Intermediate | Structure, name and characterization |
|---|---|---|---|
| 79 | 49B | 3 | 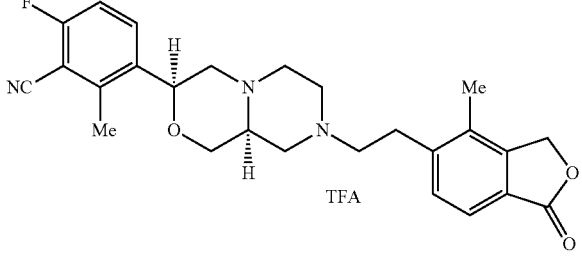<br>(3S,9aS)-3-(3-cyano-4-fluoro-2-methylphenyl)-8-[2-(4-methyl-1-oxo-1,3-dihydro-2-benzofuran-5-yl)ethyl]octahydropyrazino[2,1-c][1,4]oxazin-5-ium trifluoroacetate; LC/MS: [(M + 1)]$^+$ = 450 |
| 80 | 49A | 3 | 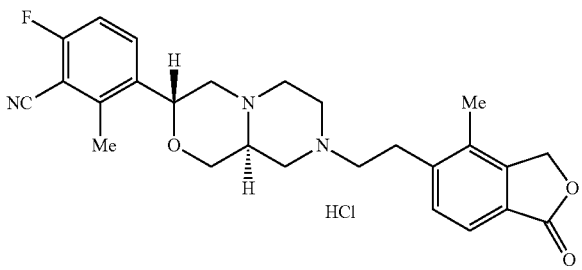<br>(3R,9aS)-3-(3-cyano-4-fluoro-2-methylphenyl)-8-[2-(4-methyl-1-oxo-1,3-dihydro-2-benzofuran-5-yl)ethyl]octahydropyrazino[2,1-c][1,4]oxazin-5-ium chloride; LC/MS: [(M + 1)]$^+$ = 450 |
| 81 | 52A | 9 | 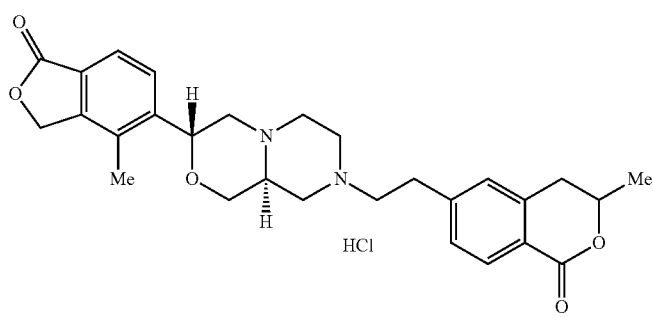<br>(3R,9aS)-3-(4-methyl-1-oxo-1,3-dihydro-2-benzofuran-5-yl)-8-[2-(3-methyl-1-oxo-3,4-dihydro-1H-isochromen-6-yl)ethyl]octahydropyrazino[2,1-c][1,4]oxazin-5-ium chloride; LC/MS: [(M + 1)]$^+$ = 477 |

TABLE 3-continued

| EXAMPLE | Amine Intermediate | Aldehyde Intermediate | Structure, name and characterization |
|---------|--------------------|-----------------------|--------------------------------------|
| 82 | 52A | 17 | 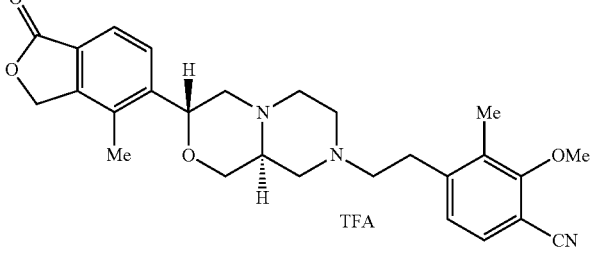<br>(3R,9aS)-8-[2-(4-cyano-3-methoxy-2-methylphenyl)ethyl]-3-(4-methyl-1-oxo-1,3-dihydro-2-benzofuran-5-yl)octahydropyrazino[2,1-c][1,4]oxazin-5-ium trifluoroacetate; LC/MS: [(M + 1)]$^+$ = 462 |
| 83 | 52A | 16 | 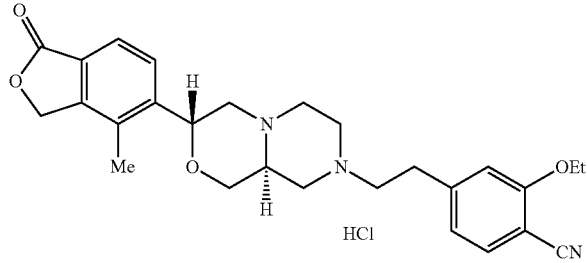<br>(3R,9aS)-8-[2-(4-cyano-3-ethoxyphenyl)ethyl]-3-(4-methyl-1-oxo-1,3-dihydro-2-benzofuran-5-yl)octahydropyrazino[2,1-c][1,4]oxazin-5-ium chloride; LC/MS: [(M + 1)]$^+$ = 462 |
| 84 | 52A | 18 | 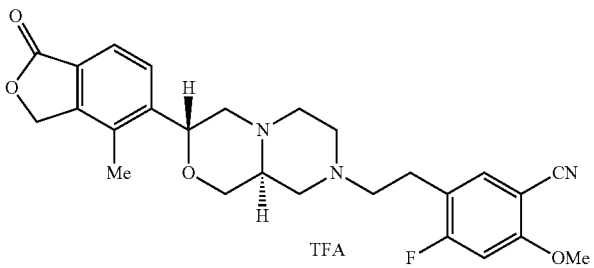<br>(3R,9aS)-8-[2-(5-cyano-2-fluoro-4-methoxyphenyl)ethyl]-3-(4-methyl-1-oxo-1,3-dihydro-2-benzofuran-5-yl)octahydropyrazino[2,1-c][1,4]oxazin-5-ium trifluoroacetate; LC/MS: [(M + 1)]$^+$ = 466 |

TABLE 3-continued

| EXAMPLE | Amine Intermediate | Aldehyde Intermediate | Structure, name and characterization |
|---|---|---|---|
| 85 | 53 | 11 | 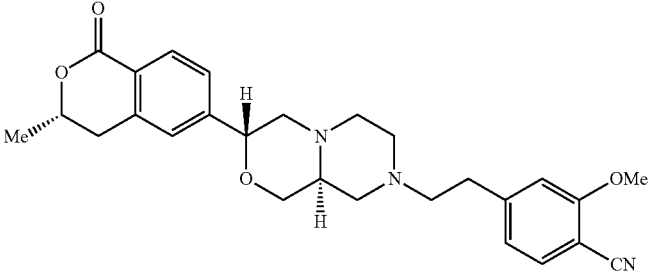 2-methoxy-4-{2-[(3R,9aS)-3-[(3S)-3-methyl-1-oxo-3,4-dihydro-1H-isochromen-6-yl]hexahydropyrazino[2,1-c][1,4]oxazin-8(1H)-yl]ethyl}benzonitrile; LC/MS: [(M + 1)]⁺ = 462 |
| 86 | 52A | 9A | 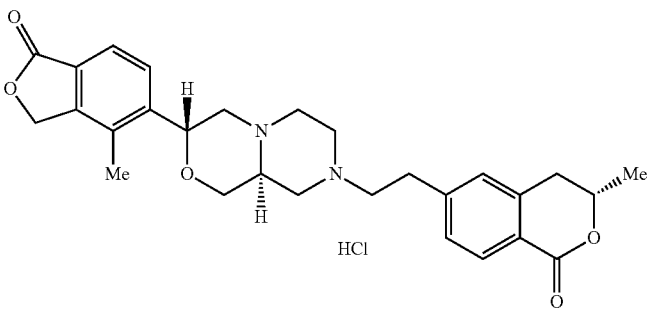 (3R,9aS)-3-(4-methyl-1-oxo-1,3-dihydro-2-benzofuran-5-yl)-8-{2-[(3S)-3-methyl-1-oxo-3,4-dihydro-1H-isochromen-6-yl]ethyl}octahydropyrazino[2,1-c][1,4]oxazin-5-ium chloride; LC/MS: [(M + 1)]⁺ = 477 |
| 87 | 52A | 9B | 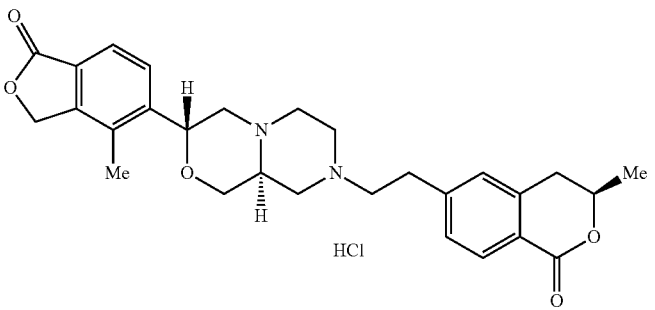 (3R,9aS)-3-(4-methyl-1-oxo-1,3-dihydro-2-benzofuran-5-yl)-8-{2-[(3R)-3-methyl-1-oxo-3,4-dihydro-1H-isochromen-6-yl]ethyl}octahydropyrazino[2,1-c][1,4]oxazin-5-ium trifluoroacetate; LC/MS: [(M + 1)]⁺ = 477 |

TABLE 3-continued

| EXAMPLE | Amine Intermediate | Aldehyde Intermediate | Structure, name and characterization |
|---|---|---|---|
| 88 | 49A | 9A | 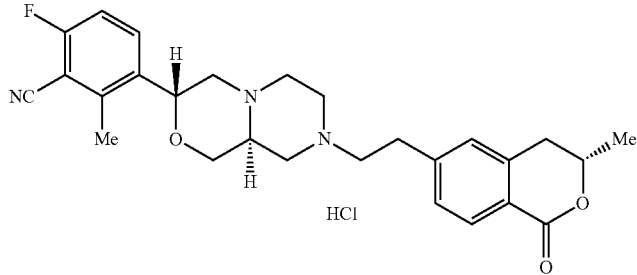<br>(3R,9aS)-3-(3-cyano-4-fluoro-2-methylphenyl)-8-{2-[(3S)-3-methyl-1-oxo-3,4-dihydro-1H-isochromen-6-yl]ethyl}octahydropyrazino[2,1-c][1,4]oxazin-5-ium chloride; LC/MS: $[(M + 1)]^+ = 464$ |
| 89 | 54 | 3 | 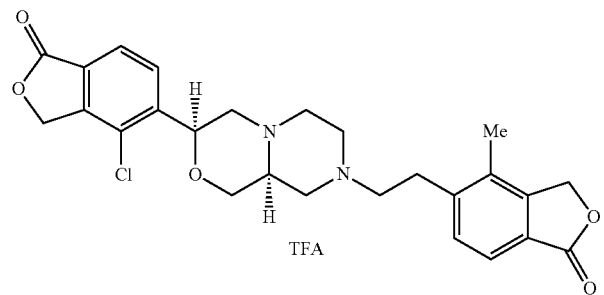<br>(3S,9aS)-3-(4-chloro-1-oxo-1,3-dihydro-2-benzofuran-5-yl)-8-[2-(4-methyl-1-oxo-1,3-dihydro-2-benzofuran-5-yl)ethyl]octahydropyrazino[2,1-c][1,4]oxazin-5-ium trifluoroacetate; LC/MS: $[(M + 1)]^+ = 483$ |
| 90 | 52A | 6 | 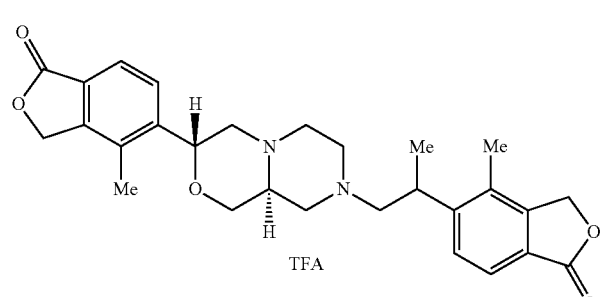<br>(3R,9aS)-3-(4-methyl-1-oxo-1,3-dihydro-2-benzofuran-5-yl)-8-[2-(4-methyl-1-oxo-1,3-dihydro-2-benzofuran-5-yl)propyl]octahydropyrazino[2,1-c][1,4]oxazin-5-ium trifluoroacetate; LC/MS: $[(M + 1)]^+ = 477$ |

TABLE 3-continued

| EXAMPLE | Amine Intermediate | Aldehyde Intermediate | Structure, name and characterization |
|---|---|---|---|
| 91 | 52A | 7 | (3R,9aS)-8-[2-(4-bromo-1-oxo-1,3-dihydro-2-benzofuran-5-yl)ethyl]-3-(4-methyl-1-oxo-1,3-dihydro-2-benzofuran-5-yl)octahydropyrazino[2,1-c][1,4]oxazin-5-ium trifluoroacetate; LC/MS: [(M + 1)]$^+$ = 527, 529 |
| 92 | 49A | 28 | (3R,9aS)-3-(3-cyano-4-fluoro-2-methylphenyl)-8-{2-[6-(1H-tetrazol-1-yl)pyridin-3-yl]ethyl}octahydropyrazino[2,1-c][1,4]oxazin-5-ium trifluoroacetate; LC/MS: [(M + 1)]$^+$ = 449 |
| 93 | 49B | 28 | (3S,9aS)-3-(3-cyano-4-fluoro-2-methylphenyl)-8-{2-[6-(1H-tetrazol-1-yl)pyridin-3-yl]ethyl}octahydropyrazino[2,1-c][1,4]oxazin-5-ium trifluoroacetate; LC/MS: [(M + 1)]$^+$ = 449 |

TABLE 3-continued

| EXAMPLE | Amine Intermediate | Aldehyde Intermediate | Structure, name and characterization |
|---|---|---|---|
| 94 | 52C | 22 | 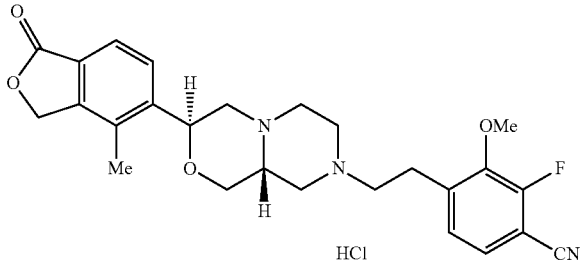<br>(3S,9aR)-8-[2-(4-cyano-3-fluoro-2-methoxyphenyl)ethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 466$ |
| 95 | 52A | 22 | 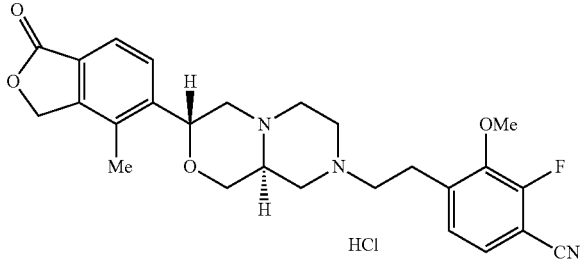<br>(3R,9aS)-8-[2-(4-cyano-3-fluoro-2-methoxyphenyl)ethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 466$ |
| 96 | 52B | 22 | 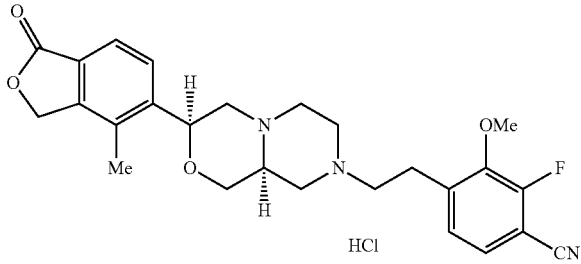<br>(3S,9aS)-8-[2-(4-cyano-3-fluoro-2-methoxyphenyl)ethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 466$ |

TABLE 3-continued

| EXAMPLE | Amine Intermediate | Aldehyde Intermediate | Structure, name and characterization |
|---|---|---|---|
| 97 | 52C | 14 | 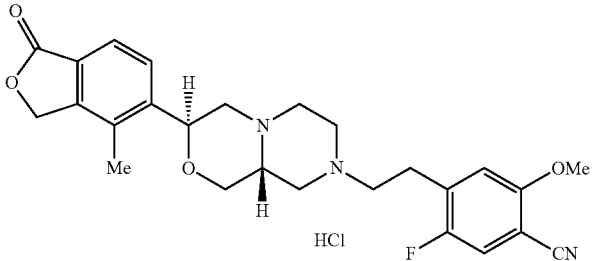<br>(3S,9aR)-8-[2-(4-cyano-2-fluoro-5-methoxyphenyl)ethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 466$ |
| 98 | 52A | 25 | 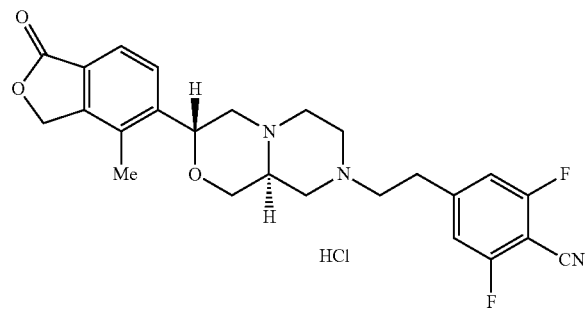<br>(3R,9aS)-8-[2-(4-cyano-3,5-difluorophenyl)ethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 454$ |
| 99 | 52A | 27 | 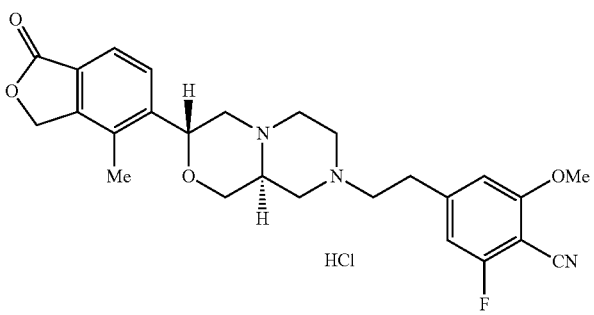<br>(3R,9aS)-8-[2-(4-cyano-3-fluoro-5-methoxyphenyl)ethyl]-3-(4-methyl-1-oxo-1,3-dihydro-2-benzofuran-5-yl)octahydropyrazino[2,1-c][1,4]oxazin-5-ium chloride; LC/MS: $[(M + 1)]^+ = 466$ |

Example 100

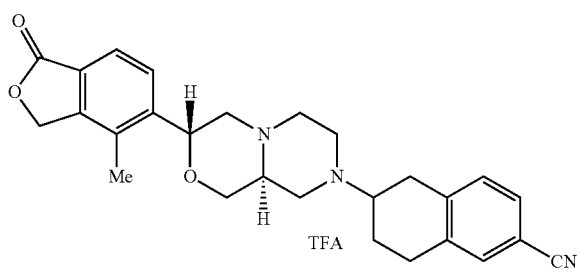 [SMILES: Cc1c([C@@H]2CN3CCN(C4CCc5cc(C#N)ccc5C4)C[C@H]3CO2)ccc2c1COC2=O]

(3R,9aS)-8-(6-cyano-1,2,3,4-tetrahydronaphthalen-2-yl)-3-(4-methyl-1-oxo-1,3-dihydro-2-benzofuran-5-yl)octahydropyrazino[2,1-c][1,4]oxazin-5-ium trifluoroacetate 4-Methyl-5-[(3R,9aS)-octahydropyrazino[2,1-c][1,4]oxazin-3-yl]-2-benzofuran-1(3H)-one (50 mg, 0.17 mmol) and 6-oxo-5,6,7,8-tetrahydronaphthalene-2-carbonitrile (29.7 mg, 0.173 mmol) were added to titanium(IV) isopropoxide (0.203 mL, 0.694 mmol) and the mixture was stirred for 1 hr. Then ethanol (2 mL) was added, followed by sodium cyanoborohydride (43.6 mg, 0.694 mmol). Shortly thereafter LC/MS showed product. The mixture was diluted with DCM and washed with brine and saturated NaHCO₃ solution. The organic layer was dried over Na₂SO₄, filtered and evaporated to dryness. The crude product was purified by preparative TLC using 5% of a 10% NH₄OH solution in methanol in chloroform. LC/MS: (M+1)⁺: 444.

Example 101

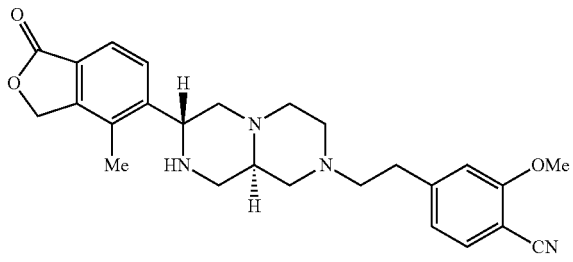 [SMILES: COc1cc(CCN2CCN3C[C@@H](c4ccc5c(c4C)COC5=O)NC[C@@H]3C2)ccc1C#N]

2-Methoxy-4-(2-((7R,9aR)-7-(4-methyl-1-oxo-1,3-dihydroisobenzofuran-5-yl)hexahydro-1H-pyrazino[1,2-a]pyrazin-2(6H)-yl)ethyl)benzonitrile Step A: (3R,9aS)-tert-butyl 8-(4-cyano-3-methoxyphenethyl)-3-(4-methyl-1-oxo-1,3-dihydroisobenzofuran-5-yl)hexahydro-1H-pyrazino[1,2-a]pyrazine-2(6H)-carboxylate To a solution of (3R,9aS)-tert-butyl 3-(4-methyl-1-oxo-1,3-dihydroisobenzofuran-5-yl)hexahydro-1H-pyrazino[1,2-a]pyrazine-2(6H)-carboxylate (23.8 mg, 0.061 mmol), 2-methoxy-4-(2-oxoethyl)benzonitrile (32.3 mg, 0.184 mmol) in methylene chloride (2 mL) was added sodium triacetoxyborohydride (39.1 mg, 0.184 mmol) and acetic acid (0.2 ml). The resulting solution was stirred at rt for 2 h. After removing the volatiles, the residue was purified on TLC (1500 MU) using 10% MeOH/DCM to give title compound. LC/MS: (M+1)⁺: 547.35.

Step B: 2-methoxy-4-(2-((7R,9aR)-7-(4-methyl-1-oxo-1,3-dihydroisobenzofuran-5-yl)hexahydro-1H-pyrazino[1,2-a]pyrazin-2(6H)-yl)ethyl)benzonitrile To the solution of (3R,9aS)-tert-butyl 8-(4-cyano-3-methoxyphenethyl)-3-(4-methyl-1-oxo-1,3-dihydroisobenzofuran-5-yl)hexahydro-1H-pyrazino[1,2-a]pyrazine-2(6H)-carboxylate (21 mg, 0.038 mmol) in methylene chloride (1 ml) was added trifluoroacetic acid (0.888 ml, 11.5 mmol), and the resulting solution was stirred at for 1 h. After removing the volatile, the residue was participated between methylene chloride and sat. sodium bicarbonate, the alkaline phase was extracted with methylene chloride, the combined organic phase was dried over sodium sulphate, concentrated and the residue was purified on TLC using 10% MeOH/DCM to give the title compound. LC/MS: (M+1)⁺: 447.25, ¹HNMR (500 MHz, CDCl₃) δ 7.831-7.815 (m, 1H), 7.759-7.744 (m, 1H), 7.749-7.464 (m, 1H), 6.898-6.863 (m, 2H), 5.247 (s, 2H), 4.332-4.313 (d, J=10.0 Hz, 1H), 3.939 (s, 3H), 3.083-3.061 (m, 1H), 2.937-2.772 (m, 7H), 2.662-2.630 (m, 2H), 2.417-2.333 (m, 6H), 2.200-2.157 (m, 1H), 2.029-1.987 (m, 1H).

Example 102

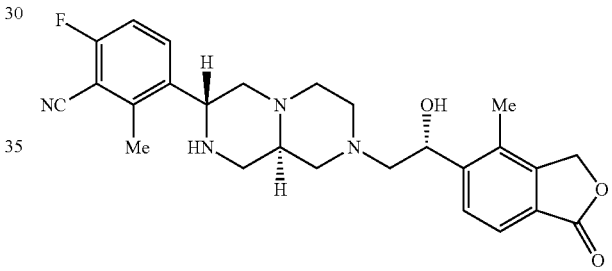

6-fluoro-3-((3R,9aR)-8-((R)-2-hydroxy-2-(4-methyl-1-oxo-1,3-dihydroisobenzofuran-5-yl)ethyl)octahydro-1H-pyrazino[1,2-a]pyrazin-3-yl)-2-methylbenzonitrile Step A: (3R,9aS)-tert-butyl 3-(3-cyano-4-fluoro-2-methylphenyl)-8-((R)-2-hydroxy-2-(4-methyl-1-oxo-1,3-dihydroisobenzofuran-5-yl)ethyl)hexahydro-1H-pyrazino[1,2-a]pyrazine-2(6H)-carboxylate A solution of (3R,9aS)-tert-butyl 3-(3-cyano-4-fluoro-2-methylphenyl)hexahydro-1H-pyrazino[1,2-a]pyrazine-2(6H)-carboxylate (25 mg, 0.067 mmol) and (R)-4-methyl-5-(oxiran-2-yl)isobenzofuran-1(3H)-one (16.51 mg, 0.087 mmol) in ethanol (2 ml) was heated by microwave at 140° C. for 2 h. After removing the volatiles, the residue was purified by preparative TLC (1500 MU) using 10% MeOH/DCM to give the title compound. LC/MS: (M+1)⁺: 565.38.

Step B: 6-fluoro-3-((3R,9aR)-8-((R)-2-hydroxy-2-(4-methyl-1-oxo-1,3-dihydroisobenzofuran-5-yl)ethyl)octahydro-1H-pyrazino[1,2-a]pyrazin-3-yl)-2-methylbenzonitrile To a solution of (3R,9aS)-tert-butyl 3-(3-cyano-4-fluoro-2-methylphenyl)-8-((R)-2-hydroxy-2-(4-methyl-1-oxo-1,3- dihydroisobenzofuran-5-yl)ethyl)hexahydro-1H-pyrazino[1,2-a]pyrazine-2(6H)-carboxylate (21 mg, 0.037 mmol) in methylene chloride (1 mL) was added trifluoroacetic acid (1.146 ml, 14.88 mmol) at rt for 1 h. After removing the volatiles, the residue was purified on TLC (1500 MU) using 10% MeOH/DCM/0.2M NH$_3$) to give the title compound. LC/MS: (M+1)$^+$:465.23, $^1$HNMR (500 MHz, CDCl$_3$) δ 7.909-7.879 (m, 1H), 7.816 (s, 2H), 7.085-7.051 (m, 1H), 5.273 (s, 2H), 5.138-5.122 (m, 1H), 4.218-4.198 (m, 1H), 3.175-3.160 (m, 1H), 3.057-3.034 (m, 1H), 2.839-2.742 (m, 4H), 2.625 (s, 3H), 2.596-2.568 (m, 1H), 2.476-2.430 (m, 4H), 2.309 (s, 3H), 2.289-2.268 (m, 1H), 2.145-2.102 (m, 1H).

The Examples in Table 4 were prepared in an analogous fashion to that described for Examples 101-102 above starting from amines and either aldehydes or epoxides, prepared as described above. The compounds were isolated as free bases, HCl salts, or TFA salts.

TABLE 4

| EXAMPLE | Amine Intermediate | Aldehyde or epoxide Intermediate | Structure, name and characterization |
|---|---|---|---|
| 103 | 43A | 1 | 6-fluoro-2-methyl-3-{(3R,9aR)-8-[2-(1-oxo-1,3-dihydro-2-benzofuran-5-yl)ethyl]octahydro-2H-pyrazino[1,2-a]pyrazin-3-yl}benzonitrile; LC/MS: [(M + 1)]$^+$ = 435 |
| 104 | 43B | 1 | 6-fluoro-2-methyl-3-{(3S,9aR)-8-[2-(1-oxo-1,3-dihydro-2-benzofuran-5-yl)ethyl]octahydro-2H-pyrazino[1,2-a]pyrazin-3-yl}benzonitrile; LC/MS: [(M + 1)]$^+$ = 435 |
| 105 | 43D | 1 | 6-fluoro-2-methyl-3-{(3R,9aS)-8-[2-(1-oxo-1,3-dihydro-2-benzofuran-5-yl)ethyl]octahydro-2H-pyrazino[1,2-a]pyrazin-3-yl}benzonitrile; LC/MS: [(M + 1)]$^+$ = 435 |

TABLE 4-continued

| EXAMPLE | Amine Intermediate | Aldehyde or epoxide Intermediate | Structure, name and characterization |
|---|---|---|---|
| 106 | 43C | 1 | 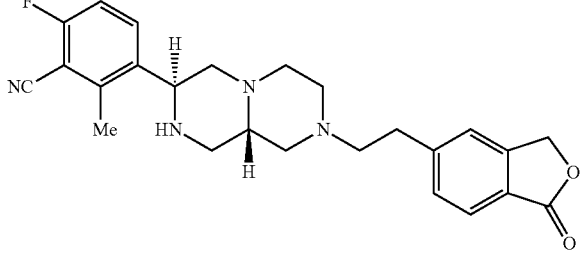 6-fluoro-2-methyl-3-{(3S,9aS)-8-[2-(1-oxo-1,3-dihydro-2-benzofuran-5-yl)ethyl]octahydro-2H-pyrazino[1,2-a]pyrazin-3-yl}benzonitrile; LC/MS: [(M + 1)]$^+$ = 435 |
| 107 | 43D | 4B | 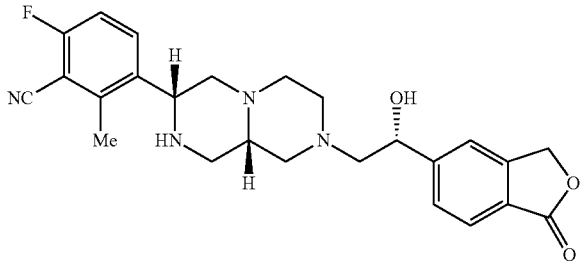 [SMILES: Cc1c([C@@H]2CN3CCN(C[C@H](O)c4ccc5c(c4C)COC5=O)C[C@H]3CN2)ccc(F)c1C#N] 6-fluoro-3-{(3R,9aS)-8-[(2R)-2-hydroxy-2-(4-methyl-1-oxo-1,3-dihydro-2-benzofuran-5-yl)ethyl]octahydro-2H-pyrazino[1,2-a]pyrazin-3-yl}-2-methylbenzonitrile; LC/MS: [(M + 1)]$^+$ = 451 |
| 108 | 43C | 4B | 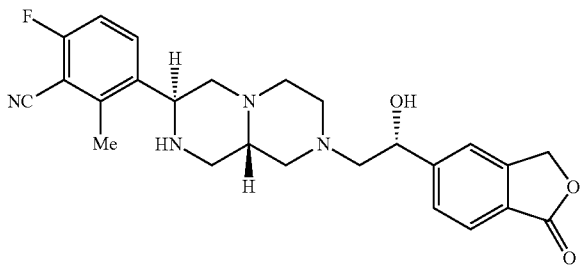 6-fluoro-3-{(3S,9aS)-8-[(2R)-2-hydroxy-2-(4-methyl-1-oxo-1,3-dihydro-2-benzofuran-5-yl)ethyl]octahydro-2H-pyrazino[1,2-a]pyrazin-3-yl}-2-methylbenzonitrile; LC/MS: [(M + 1)]$^+$ = 451 |

Example 109

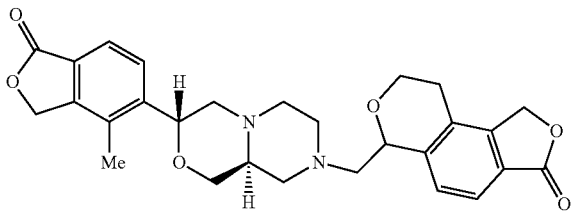 [SMILES: Cc1c([C@@H]2CN3CCN(CC4OCCc5c4ccc4c5COC4=O)C[C@H]3CO2)ccc2c1COC2=O]

6-{[(3R,9aS)-3-(4-methyl-1-oxo-1,3-dihydro-2-benzofuran-5-yl)hexahydropyrazino[2,1-c][1,4]oxazin-8(1H)-yl]methyl}-8,9-dihydro-1H-furo[3,4-f]isochromen-3(6H)-one 3-Oxo-3,6,8,9-tetrahydro-1H-furo[3,4-f]isochromen-6-yl)methyl 4-methylbenzenesulfonate (0.05 g, 0.13 mmol), and 4-methyl-5-((3R,9aS)-octahydropyrazino[2,1-c][1,4]oxazin-3-yl)isobenzofuran-1(3H)-one (0.04 g, 0.2 mmol) were added into a 5 ml microwave tube; to the 10 tube was added acetonitrile (2.5 mL), the tube was degassed and purged with $N_2$, followed by heating in a microwave reactor at 120° C. for 1 hr.; LC indicated completion of the reaction and formation of the desired product. The solution was concentrated to dryness, re-dissolved in methanol, and purified by mass-directed preparative HPLC to afford the title compound. LC/MS: $[(M+1)]^+=491$.

The following Thallium Flux Assay and/or the Electrophysiology Assay were performed on each of the final product compounds in the Examples unless otherwise noted.

Thallium Flux Assay

Cell Culture Conditions—

HEK293 cells stably expressing hROMK ($hK_{ir}1.1$) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
 FluxOR™ Reagent (Component A)
 FluxOR™ Assay Buffer (Component B)—10× Concentrate
 PowerLoad™ Concentrate (Component C)—100× Concentrate
 Probenecid (Component D)—Lyophilized sample is kept at −20° C. Water soluble, 100× after solubilization in 1 mL water. Store at 4° C.
 FluxOR™ Chloride-free Buffer (Component E)—5× Concentrate
 Potassium sulfate ($K_2SO_4$) Concentrate (Component F)—125 mM in water. Store at 4° C.
 Thallium sulfate ($Tl_2SO_4$) Concentrate (Component G)—50 mM in water. Store at 4° C.
 DMSO (dimethyl sulfoxide, Component H)—1 mL (100%)

Reagent Preparation: FluxOR Working Solutions
 1000× FluxOR™ Reagent: Reconstitute a vial of component A in 100 µl DMSO; Mix well; Store 10 µl aliquots at −20° C.
 1× FluxOR™ Assay Buffer: Dilute Component B 10-fold with water; Adjust pH to 7.4 with Hepes/NaOH; Filter and store at 4° C.
 Probenecid/Assay Buffer: 100 mL of 1× FluxOR™ Assay Buffer; 1 mL of reconstituted component D; Store at 4° C.
 Loading Buffer (per microplate): 10 µl 1000× FluxOR™ Reagent; 100 µl component C; 10 mL Probenecid/Assay Buffer
 Compound Buffer (per microplate): 20 mL Probenecid/Assay Buffer; 0.3 mM ouabain (10 mM ouabain in water can be stored in amber bottle/aluminum foil at room temperature); Test compound
 1× FluxOR™ Chloride-Free Buffer: Prepare 1× working solution in water. Can be stored at room temperature
 Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066) for approximately 6 min at 37° C. and suspended in 10 mL of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/mL amphotericin B for 4 min. Amphotericin B (Sigma A-4888) was prepared as a 40 mg/mL solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formulas I-V of the present invention, preferably with an $IC_{50}$ potency of less than 1 µM in this assay. Alternatively, the control could be another compound (outside the scope of Formulas I-V) that has an $IC_{50}$ potency in this assay of less than 1 µM.

Data collected for compounds in the Examples of the present invention using the Thallium Flux Assay and the Electrophysiology Assay are shown in Table 5 below. All of the tested final product compounds in the Examples (diastereomeric mixtures and individual diastereomers) had $IC_{50}$ potencies less than 1 µM in one or both of the Thallium Flux Assay and the Electrophysiology Assay.

TABLE 5

| Example No. | Thallium Flux $IC_{50}$ (µM) | Electrophysiology $IC_{50}$ (µM) |
| --- | --- | --- |
| 1 | 0.22 | 0.11 |
| 2 | 0.23 | 0.08 |
| 3 | 0.12 | 0.05 |
| 4 | 0.43 | 0.08 |
| 5 | 0.28 | 0.10 |
| 6 | 0.19 | 0.12 |
| 7 | 0.29 | 0.11 |
| 8 | 0.34 | 0.12 |
| 9 | 0.43 | 0.31 |
| 10 | 0.55 | 0.13 |
| 11 | 0.36 | 0.06 |
| 12 | 0.19 | 0.03 |
| 13 | 0.27 | 0.22 |
| 14 | 0.58 | 0.27 |
| 15 | 0.67 | 0.29 |
| 16 | 0.56 | 0.08 |
| 17 | 0.85 | 0.15 |
| 18 | 0.29 | 0.10 |
| 19 | 0.44 | 0.26 |
| 20 | 0.30 | 0.24 |
| 21 | 0.26 | 0.21 |
| 22 | 0.31 | 0.44 |
| 23 | 0.32 | 0.12 |
| 24 | 0.45 | 0.24 |
| 25 | 0.34 | 0.19 |
| 26 | 0.25 | 0.22 |
| 27 | 0.31 | 0.24 |
| 28 | 0.19 | 0.09 |
| 29 | 0.49 | 0.08 |
| 30 | 0.23 | 0.14 |
| 31 | 0.65 | 0.14 |
| 32 | 0.28 | 0.18 |
| 33 | 0.60 | 0.17 |
| 34 | 0.31 | 0.15 |
| 35 | 0.27 | 0.13 |
| 36 | 0.39 | 0.12 |
| 37 | 0.47 | 0.11 |
| 38 | 0.44 | 0.12 |
| 39 | 0.30 | 0.15 |
| 40 | 0.26 | 0.11 |
| 41 | 0.23 | 0.14 |
| 42 | 0.22 | 0.08 |
| 43 | 0.21 | 0.13 |
| 44 | 0.27 | 0.13 |
| 45 | 0.47 | 0.12 |
| 46 | 0.28 | 0.11 |
| 47 | 0.25 | 0.19 |
| 48 | 0.22 | 0.21 |
| 49 | 0.25 | 0.05 |
| 50 | 0.44 | 0.25 |
| 51 | 0.40 | 0.23 |
| 52 | 0.41 | 0.10 |
| 53 | 0.24 | 0.08 |
| 54 | 0.34 | 0.17 |
| 55 | 0.33 | 0.09 |
| 56 | 0.04 | 0.07 |
| 57 | 0.03 | 0.09 |
| 58 |  | 0.12 |
| 59 |  | 0.04 |
| 60 |  | 0.18 |
| 61 | 0.33 | 0.12 |
| 62 |  | 0.04 |
| 63 | 0.23 | 0.04 |
| 64 | 0.04 | 0.04 |
| 65 | 0.17 | 0.11 |
| 66 | 0.17 | 0.14 |
| 67 |  | 0.07 |
| 68 |  | 0.14 |
| 69 | 0.06 | 0.02 |
| 70 | 0.12 | 0.03 |
| 71 | 0.11 | 0.20 |
| 72 | 0.15 | 0.16 |
| 73 | 0.57 | 0.30 |
| 74 |  | 0.08 |
| 75 | 0.11 | 0.07 |
| 76 | 0.44 | 0.09 |
| 77 |  | 0.07 |

TABLE 5-continued

| Example No. | Thallium Flux IC$_{50}$ (μM) | Electrophysiology IC$_{50}$ (μM) |
|---|---|---|
| 78 |  | 0.07 |
| 79 | 0.27 | 0.07 |
| 80 | 0.06 | 0.05 |
| 81 | 0.09 | 0.12 |
| 82 | 0.06 | 0.08 |
| 83 | 0.12 | 0.09 |
| 84 |  | 0.05 |
| 85 |  | 0.09 |
| 86 | 0.08 | 0.08 |
| 87 | 0.11 | 0.05 |
| 88 | 0.19 | 0.05 |
| 89 | 0.20 | 0.10 |
| 90 | 0.11 | 0.23 |
| 91 | 0.09 | 0.21 |
| 92 | 0.27 | 0.08 |
| 93 | 0.08 | 0.08 |
| 94 | 0.24 | 0.14 |
| 95 | 0.12 | 0.11 |
| 96 | 0.21 | 0.08 |
| 97 | 0.35 | 0.28 |
| 98 | 0.17 | 0.09 |
| 99 | 0.26 | 0.21 |
| 100 | 0.03 | 0.21 |
| 101 | 0.21 | 0.10 |
| 102 | 0.21 | 0.12 |
| 103 | 0.14 | 0.06 |
| 104 | 0.11 | 0.40 |
| 105 | 0.29 | 0.15 |
| 106 | 0.13 | 0.05 |
| 107 | 0.16 | 0.20 |
| 108 | 0.10 | 0.10 |
| 109 |  | 0.05 |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR):

Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. The compound of Example 1 was evaluated at PO, QD doses at one or more doses within the range of 3 to 10 mg/kg and resulted in typical reductions in daily (24 h) mean systolic blood pressure ranging from 9.5 mmHg to 21 mmHg at the doses used by the last day of the studies.

The Spontaneously Hypertensive Rat Assay is well known and often used in the art as an experimental model simulating human hypertension (see, e.g., Lerman, L. O., et al., *J Lab Clin Med,* 2005; 146:160-173).

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I

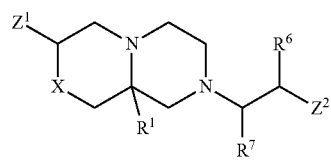

or a pharmaceutically acceptable salt thereof wherein:
$R^1$ is —H or —$C_{1-4}$alkyl;
X is O, NH or S;
$Z^1$ is

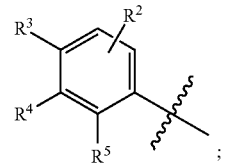

$R^2$ is H, halo, —$C_{1-6}$alkyl, —$C_{3-6}$cycloalkyl or —$OC_{1-6}$alkyl;
$R^3$ is —H, halo, —CN, —$C_{1-6}$ alkyl, —$C_{3-6}$cycloalkyl, —$OC_{1-6}$alkyl or N-tetrazolyl optionally substituted with —$CH_3$;
$R^4$ is —H, halo, —CN, —$C_{1-6}$ alkyl, —$C_{3-6}$cycloalkyl, —$OC_{1-6}$alkyl or N-tetrazolyl optionally substituted with —$CH_3$;
or $R^3$ and $R^4$ are joined together, and with the phenyl ring to which they are attached together represent:

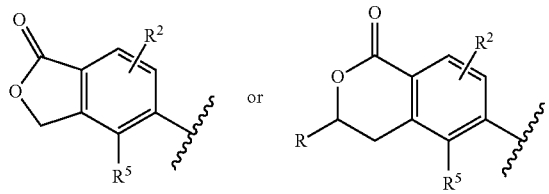

wherein R is —H or —$C_{1-4}$alkyl;
$R^5$ is —H, halo, —CN, —$C_{1-4}$alkyl, —$OC_{1-4}$alkyl or —$C_{3-6}$cycloalkyl;
provided that when $R^3$ and $R^4$ are not joined together, then
(a) one and only one of $R^3$, $R^4$ or $R^5$ is —CN, or
(b) one of $R^3$ or $R^4$ is N-tetrazolyl optionally substituted with —$CH_3$ and the other is not N-tetrazolyl optionally substituted with —$CH_3$;
$Z^2$ is

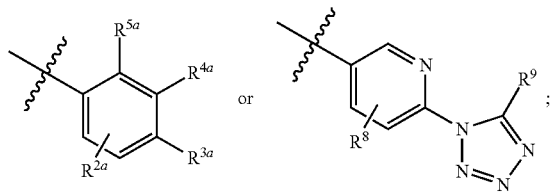

$R^{2a}$ is —H, halo, —$C_{1-6}$alkyl, —$C_{3-6}$cycloalkyl or —$OC_{1-6}$alkyl;
$R^{3a}$ is —H, halo, —CN, —$C_{1-6}$alkyl, —$C_{3-6}$cycloalkyl, —$OC_{1-6}$alkyl or N-tetrazolyl optionally substituted with —$CH_3$;
$R^{4a}$ is —H, halo, —CN, —$C_{1-6}$alkyl, —$C_{3-6}$cycloalkyl, —$OC_{1-6}$alkyl or N-tetrazolyl optionally substituted with —$CH_3$;
or $R^{3a}$ and $R^{4a}$ are joined together, and with the phenyl ring to which they are attached together represent:

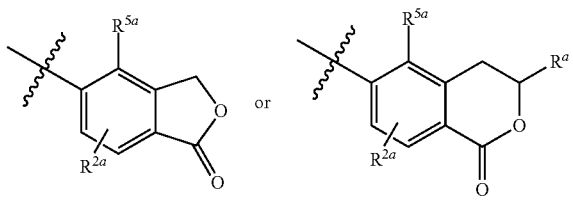

wherein $R^a$ is —H or —$C_{1-4}$alkyl;
$R^{5a}$ is —H, halo, —CN, —$C_{1-4}$alkyl, —$OC_{1-4}$alkyl or —$C_{3-6}$cycloalkyl;
provided that when $R^{3a}$ and $R^{4a}$ are not joined together, then
(a) one of $R^{3a}$, $R^{4a}$ or $R^{5a}$ is —CN and the others are not —CN, or
(b) one of $R^{3a}$ or $R^{4a}$ is N-tetrazolyl optionally substituted with —$CH_3$ and the other is not N-tetrazolyl optionally substituted with —$CH_3$;
$R^6$ is —H, —OH or —$C_{1-3}$alkyl; or $R^6$ is —O— and is joined together with $Z^2$ to represent:

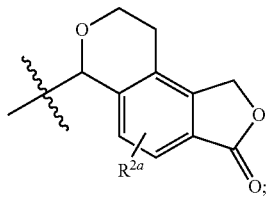

$R^7$ is —H: or $R^7$ together with —$CHR^6$— and $Z^2$ represents

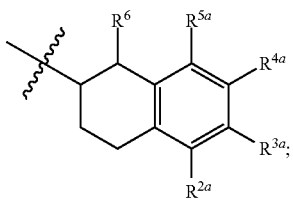

$R^8$ is —H or —$C_{1-3}$alkyl; and
$R^9$ is —H or —$CH_3$.

2. The compound of claim 1 having structural Formula II or a pharmaceutically acceptable salt thereof:

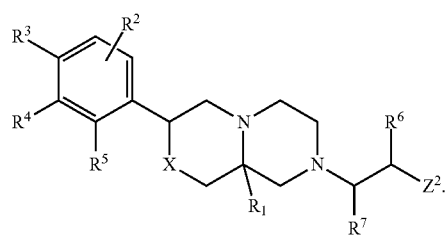

II

3. The compound of claim 2 or a pharmaceutically acceptable salt thereof wherein: $R^2$ is —H, halo, —$C_{1-3}$alkyl or —$OC_{1-3}$alkyl; $R^3$ is halo, —CN or —$OC_{1-3}$ alkyl; $R^4$ is —H, halo, —CN or —$OC_{1-3}$alkyl; and $R^5$ is —H, halo, —$C_{1-3}$alkyl, —$OC_{1-3}$alkyl or —$C_{3-4}$cycloalkyl;
provided that one of $R^3$ or $R^4$ is —CN and the other is not —CN.

4. The compound of claim 1 having structural Formula III or a pharmaceutically acceptable salt thereof:

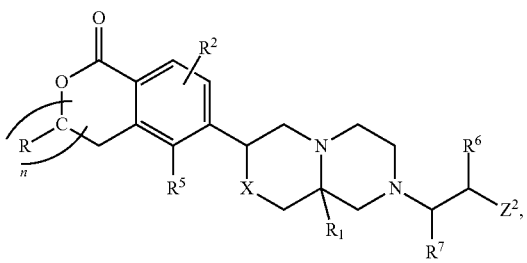

III wherein n is the integer zero or 1.

5. The compound of claim 4 or a pharmaceutically acceptable salt thereof wherein: $R^2$ is —H, halo, —$C_{1-3}$alkyl or —$OC_{1-3}$alkyl; and $R^5$ is —H, halo, —$C_{1-3}$alkyl, —$OC_{1-3}$alkyl or —$C_{3-4}$cycloalkyl.

6. The compound of claim 1 or a pharmaceutically acceptable salt thereof wherein:
(i) $Z^2$ is

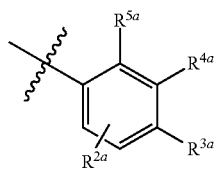

or
(ii) $R^7$ together with —CHR$^6$— and $Z^2$ represents:

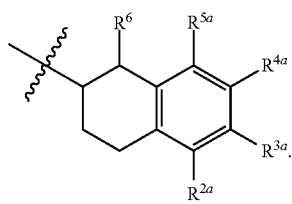

7. The compound of claim 6 or a pharmaceutically acceptable salt thereof wherein: $R^{2a}$ is —H, halo, —C$_{1-3}$alkyl or —OC$_{1-3}$alkyl; $R^{3a}$ is halo, —CN, —OC$_{1-3}$alkyl or N-tetrazolyl; $R^{4a}$ is —H, halo, —CN, —OC$_{1-3}$ alkyl or N-tetrazolyl; and $R^{5a}$ is —H, halo, —C$_{1-3}$alkyl, —OC$_{1-3}$ alkyl or —C$_{3-4}$cycloalkyl; provided that:
(a) one of $R^{3a}$ or $R^{4a}$ is —CN and the other is not —CN, or
(b) one of $R^{3a}$ or $R^{4a}$ is N-tetrazolyl and the other is not N-tetrazolyl.

8. The compound of claim 1 or a pharmaceutically acceptable salt thereof wherein $Z^2$ is

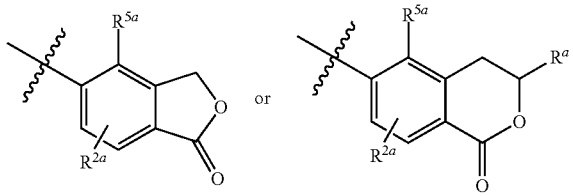

or wherein $R^6$ is —O— and is joined together with $Z^2$ to represent

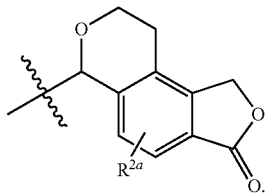

9. The compound of claim 8 or a pharmaceutically acceptable salt thereof wherein $R^{2a}$ is —H, halo, —C$_{1-3}$alkyl or —OC$_{1-3}$ alkyl; and $R^{5a}$, when present, is —H, halo, —C$_{1-3}$alkyl, —OC$_{1-3}$alkyl or —C$_{3-4}$cycloalkyl.

10. The compound of claim 1 or a pharmaceutically acceptable salt thereof wherein $Z^2$ is

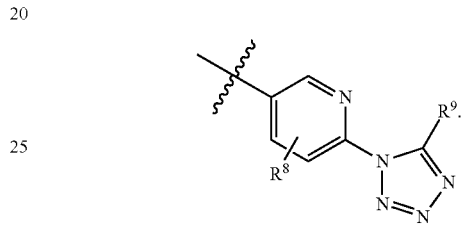

11. The compound of claim 10 or a pharmaceutically acceptable salt thereof wherein $R^8$ is —H or —C$_{1-3}$alkyl; and $R^9$ is —H.

12. The compound of claim 1 or a pharmaceutically acceptable salt thereof wherein X is O or N.

13. A pharmaceutical composition comprised of a compound of claim 1 or a pharmaceutically acceptable salt thereof and a pharmaceutically acceptable carrier.

14. The pharmaceutical composition of claim 13 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pro-drug thereof, or a pharmaceutically acceptable salt of any of the foregoing.

* * * * *